United States Patent
De et al.

(10) Patent No.: US 11,872,236 B2
(45) Date of Patent: Jan. 16, 2024

(54) PHARMACOLOGICAL AGENTS FOR TREATING OCULAR DISEASES

(71) Applicant: CALASIA PHARMACEUTICALS, INC., San Diego, CA (US)

(72) Inventors: Surya Kanta De, San Diego, CA (US); Sridhar G. Prasad, San Diego, CA (US); Marshall Clarke Peterman, Oceanside, CA (US); Bernard Collins, Cardiff, CA (US)

(73) Assignee: CALASIA PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 17/045,430

(22) PCT Filed: Apr. 5, 2019

(86) PCT No.: PCT/US2019/026112
§ 371 (c)(1),
(2) Date: Oct. 5, 2020

(87) PCT Pub. No.: WO2019/195761
PCT Pub. Date: Oct. 10, 2019

(65) Prior Publication Data
US 2021/0154213 A1 May 27, 2021

Related U.S. Application Data

(60) Provisional application No. 62/653,249, filed on Apr. 5, 2018, provisional application No. 62/694,729, filed on Jul. 6, 2018.

(51) Int. Cl.
| | | |
|---|---|---|
| A61K 31/6615 | (2006.01) | |
| A61K 31/12 | (2006.01) | |
| A61P 27/10 | (2006.01) | |
| A61P 25/16 | (2006.01) | |
| A61P 43/00 | (2006.01) | |

(52) U.S. Cl.
CPC .......... *A61K 31/6615* (2013.01); *A61K 31/12* (2013.01); *A61P 25/16* (2018.01); *A61P 27/10* (2018.01); *A61P 43/00* (2018.01)

(58) Field of Classification Search
CPC ............... A61K 31/12; A61K 31/4353; A61K 31/437; A61K 31/4741; A61K 31/6615; A61P 27/10; A61P 27/12; A61P 25/16; A61P 43/00
See application file for complete search history.

(56) References Cited

U.S. PATENT DOCUMENTS

| | | |
|---|---|---|
| 5,476,875 A | 12/1995 | Bernauer et al. |
| 5,877,353 A | 3/1999 | Bruhin |
| 2011/0152274 A1 | 6/2011 | Kaufman |
| 2015/0246963 A1 | 9/2015 | Cho et al. |
| 2016/0317474 A1 | 11/2016 | Aung et al. |
| 2016/0374961 A1 | 12/2016 | Graef et al. |

FOREIGN PATENT DOCUMENTS

| | | | |
|---|---|---|---|
| CN | 1188755 A | 7/1998 | |
| CN | 106163548 A | 11/2016 | |
| CN | 107206009 A | 9/2017 | |
| JP | S62240649 A | 10/1987 | |
| WO | WO-2011047412 A1 * | 4/2011 | .......... A61K 31/198 |
| WO | 2014147464 A1 | 9/2014 | |
| WO | 2014147464 A2 | 9/2014 | |
| WO | WO-2015095257 A2 * | 6/2015 | .......... A61K 31/137 |
| WO | 2016029199 A1 | 2/2016 | |
| WO | 2017039525 A1 | 3/2017 | |
| WO | 2022104383 A1 | 5/2022 | |
| WO | 2023278464 A1 | 1/2023 | |

OTHER PUBLICATIONS

International Search Report issued in PCT/US2019/026112, dated Aug. 2, 2019, 6 pages.
Makley L. et al., "Pharmacological restoration of transparency in cataract", ACTA Ophthalmologica Oct. 1, 2016, Blackwell Publishing Ltd NLD, vol. 94, No. Supplement 256, Oct. 1, 2016. DOI: 10.1111/j.1755-3768.2016.0145.
Ricardo Sant'Anna et al. "Repositioning tolcapone as a potent inhibitor of transthyretin amyloidogenesis and associated cellular toxicity," Nature Communications, Feb. 23, 2016, DOI 10.1038/ncomms10787, pp. 1-13.
Nakazawa et al., "Administration of antioxidant compounds affect the lens chaperone activity and prevents the onset of cataracts," Biomedicine & Pharmaotherapy, 2017, vol. 95, pp. 137-143.
Bertolini et al., "Novel Screening Assay for Antioxidant Protection against Peroxyl Radical-Induced Loss of Protein Function," 2007, vol. 96, No. 11, pp. 2931-2944.
Fleisher et al., "Improved oral drug delivery: solubility limitations overcome by the use of prodrugs," Advanced Drug Delivery Reviews, 19 (1996), pp. 115-130.

* cited by examiner

*Primary Examiner* — Sarah Pihonak
(74) *Attorney, Agent, or Firm* — ArentFox Schiff LLP

(57) ABSTRACT

Methods of treating presbyopia or cataract in a subject in need thereof are provided. The methods require administering to the subject an effective amount of a composition comprising a compound that inhibits the formation of high molecular weight aggregates of human α-A-crystallin. Compositions containing certain compounds are believed to be also effective in the treatment of transthyretin (TTR)-associated amyloidosis and Parkinson's disease.

19 Claims, 12 Drawing Sheets

7A

7B

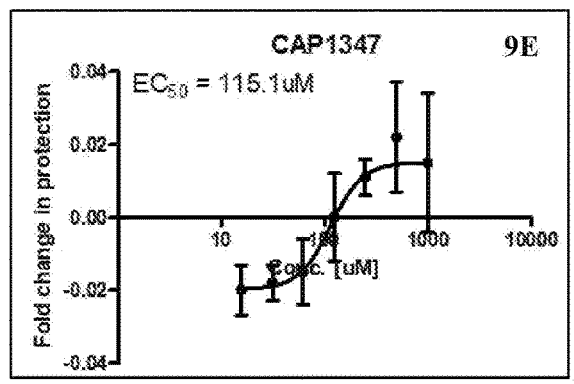
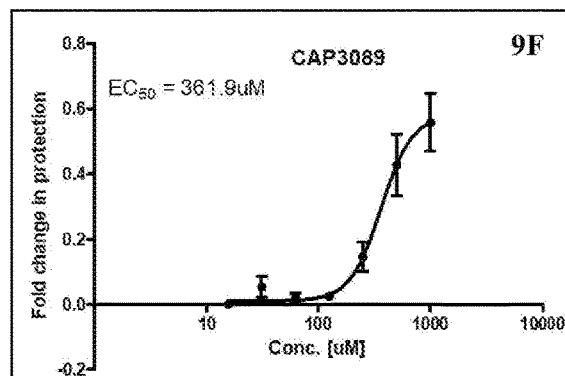
FIGS. 9E-9F
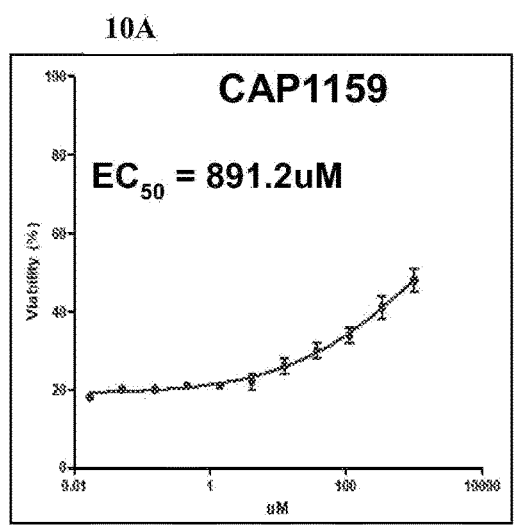
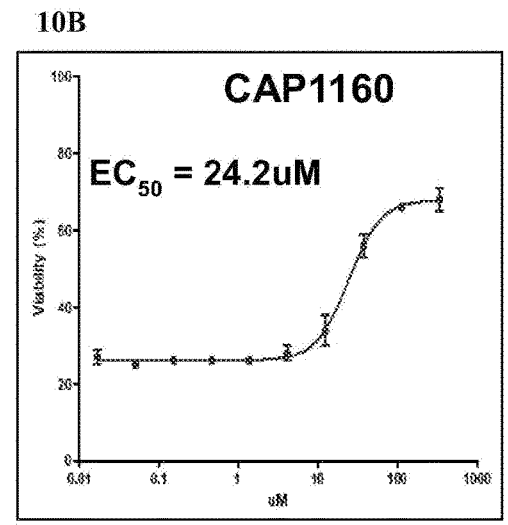
FIGS. 10A-10B

10C

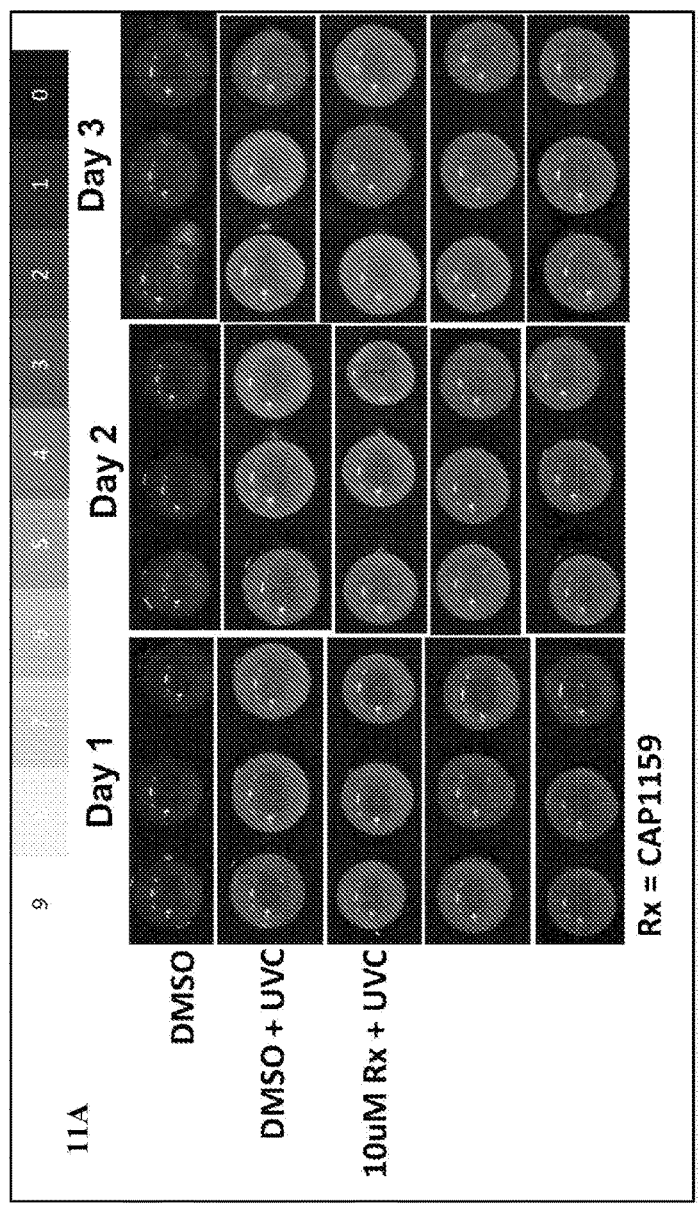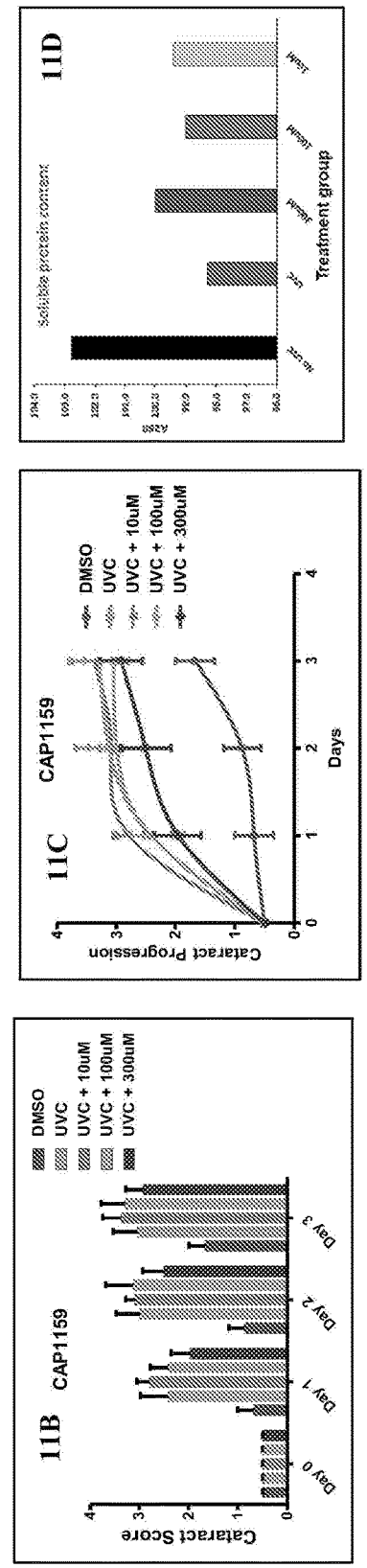
FIGS. 11A-11D

PHARMACOLOGICAL AGENTS FOR TREATING OCULAR DISEASES

CROSS-REFERENCE TO RELATED APPLICATIONS

This application is a National Stage Entry of PCT/US2019/026112, filed Apr. 5, 2019, which claims priority to U.S. provisional application Nos. 62/653,249 filed Apr. 5, 2018 and 62/694,729, filed Jul. 6, 2018, the disclosures of each of which are hereby incorporated by reference in their entireties.

CROSS REFERENCES TO RELATED APPLICATIONS

This application claims the benefit of U.S. Provisional Application No. 62/653,249 filed Apr. 5, 2018, and U.S. Provisional Application No. 62/694,729 filed Jul. 6, 2018, which are both hereby incorporated by reference in their entireties.

BACKGROUND

Presbyopia is the loss of accommodative ability of the eye resulting in the inability to focus on near objects. Presbyopia affects everyone over the age of 45 and has significant negative impacts on the quality of life. Current treatments for presbyopia include: (i) non-invasive approaches that utilize devices to help improve near and distance vision but do nothing to restore the natural process of accommodation and require constant use of the devices, and (ii) invasive surgical procedures which are associated with major complications including decrease in vision quality, regression effects, anisometropia, corneal ectasia, and haze. Most importantly, none of these methods can reverse presbyopia. Moreover, no treatment option exists that can either prevent or delay the onset of presbyopia.

Stiffening of eye lens, and changes in the elasticity of the lens capsule, dimension of eye lens, dimension of the zonular attachment, and ciliary muscle (CM) contractions, have all been proposed as contributing factors for presbyopia. However, human and non-human primate studies suggest that CM function is normal well beyond the onset of presbyopia. By contrast, the human lens increases in stiffness with age in a manner that directly correlates with a loss in accommodative power (FIG. 1). The loss in accommodative power can be restored by implanting intraocular lenses made from a flexible polymer suggesting that restoration of lens flexibility is sufficient to restore accommodation. Therefore, a pharmacological agent that could prevent or reverse the hardening of the crystalline lens would provide a promising avenue for a novel non-invasive treatment for presbyopia.

At the molecular level, proteins known as crystallins play a major role in the stiffening of the eye lens. The lens crystallins comprise three isoforms, α, β, and γ and make up 90% of the eye lens protein content. α crystalline (AC), an ATP-independent chaperone and member of the small heat shock protein (sHsp) family, constitutes 40% of the crystallin protein content. It exists as a hetero-oligomer of two subunits, αA-crystallin (AAC) and αB-crystallin (ABC) and its expression is primarily restricted to the eye lens. It recognizes exposed conformational features in partially unfolded lens proteins and sequesters them from one another, thereby reducing the population of aggregation-prone species that would otherwise lead to various age-related vision impairment.

Multiple studies have established a link between stiffening of the human lens and AC function. Dynamic mechanical analysis measurements have shown that there is a significant increase in the stiffness of the lens with age, particularly in the lens nucleus where a 500- to 1000-fold decrease in elasticity is observed (FIG. 1A). This increase in lens stiffness correlates with the age-related decline in free AC chaperone concentration as most AC becomes incorporated into high molecular weight (HMW) aggregates by the age of 40-50 (FIG. 2). This conversion of soluble AC into HMW aggregates is accompanied by a large increase in lens stiffness (FIG. 1A), presumably because the low level of soluble AC present is not sufficient to chaperone denatured proteins. That age-related decrease in free AC chaperone is responsible for lens stiffness is supported by experiments where human lenses were subjected to heating to mimic the age-related conversion of soluble AC into HMW aggregates and an increase in lens stiffness was observed. Similarly, purified soluble AC forms HMW aggregates when exposed to UV radiation with a loss in chaperone like activity. The HMW aggregate is formed due to the intermolecular cross-linking, particularly S—S bonds, resulting from the oxidation of cysteine sulfhydryl groups (—SH). The formation of this disulfide cross-linked HMW aggregate is thought to be a major contributor in increasing the stiffness and loss of accommodation amplitude of the lens.

It has been suggested that presbyopia is the earliest observable symptom of age-related nuclear (ARN) cataract, a major cause of blindness in the world.

Given the need for noninvasive treatment that can protect and restore the accommodative ability of the eye lost in presbyopia and given that formation of HMW AC aggregates is a major causative factor underlying presbyopia, there is a need for the development of pharmacological agents that can selectively delay and/or reverse the HMW AC aggregate formation.

SUMMARY OF THE INVENTION

Provided herein is a rational structure activity relation-based approach for identifying small molecule disaggregases (SMDs) that can inhibit formation of HMW aggregates human ACC (hAAC). Several SMDs were identified based on this approach. It is believed that these SMDs are useful for the treatment of presbyopia, and for the treatment of cataract. The cataract can be age-related (nuclear sclerotic, cortical, and posterior subcapsular), congenital, secondary, traumatic and radiation cataracts.

In one aspect, provided herein is a method for treating presbyopia or cataract in a subject in need thereof. The method comprises administering to the subject an effective amount of a composition comprising a compound having the formula (VII)

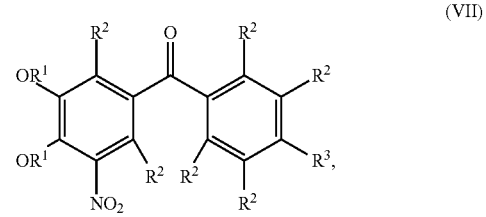

(VII)

or a solvate or a pharmaceutically acceptable salt thereof, wherein $R^1$ is independently selected from the group consisting of hydrogen; $(C_1-C_3)$alkyl; halo$(C_1-C_3)$alkyl; $(C_3-C_6)$cycloalkyl; halo$(C_3-C_6)$cycloalkyl; $(C_1-C_3)$alkyloxy; and $R^4C=O$; wherein $R^4$ is selected from the $(C_1-C_6)$alkyl; halo$(C_1-C_6)$alkyl; $(C_3-C_6)$cycloalkyl; halo$(C_3-C_6)$cycloalkyl; aryl; haloaryl; and

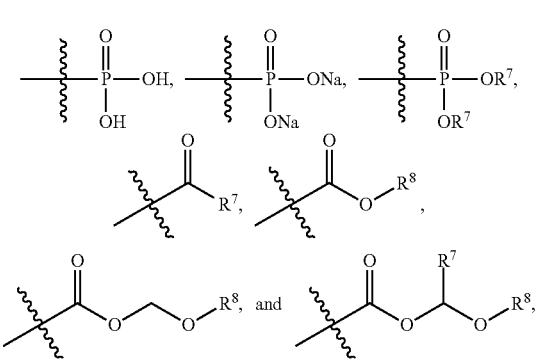

wherein $R^7$ is $(C_1-C_6)$alkyl and $R^8$ is $(C_1-C_6)$alkyl, aryl, or a polyethylene glycol group;

$R^2$ is independently selected from the group consisting of hydrogen, $R^5$, $OR^5$, $N(R^5)(R^6)$, halide, CN, $NO_2$, $C(O)OR^5$, $CON(R^5)(R^6)$, $S(O)NR^5_2$, $SO_3H$, $SO_2CH_3$, phenyl, biphenyl, phenoxy-phenyl, and polyethyleneglycol groups, wherein $R^5$ and $R^6$ are independently selected from hydrogen atom, $(C_1-C_6)$alkyl, halo$(C_1-C_6)$alkyl, $(C_3-C_6)$cycloalkyl, halo$(C_3-C_6)$cycloalkyl, $(C_3-C_6)$cycloalkyl$(C_1-C_6)$alkyl, halo$(C_3-C_6)$cycloalkyl$(C_1-C_6)$alkyl, and $(C_3-C_6)$cycloalkyl-halo$(C_1-C_6)$alkyl groups; wherein $R^2$ can occupy 0-2 positions in the ring of its occurrence; and wherein, in the event any two adjacent $R^3$ is selected from the group consisting of hydrogen, $(C_1-C_6)$alkyl, halo$(C_1-C_6)$alkyl, $(C_3-C_6)$cycloalkyl, halo$(C_3-C_6)$cycloalkyl, $(C_2-C_6)$alkenyl, halo$(C_2-C_6)$alkenyl, and hydroxy$(C_2-C_6)$alkenyl.

In one embodiment of the method requiring the compound having formula (VII), the compound is

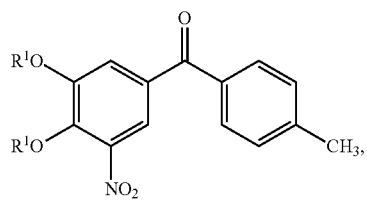

wherein $R^1$ is selected from the group consisting of

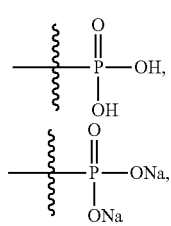

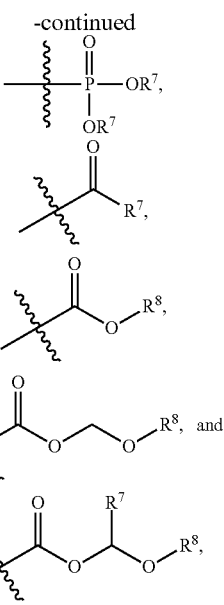

wherein $R^7$ is $(C_1-C_6)$alkyl and $R^8$ is $(C_1-C_6)$alkyl, aryl, or a polyethylene glycol group.

In one embodiment of the method requiring the compound having formula (VII), each $R^1$ is a hydrogen atom. In another embodiment, each $R^1$ is an alkyl. In yet another embodiment, one $R^1$ is a hydrogen or an alkyl, and the other $R^1$ is a carboxyl, benzoxyl, or a methoxyl. In one embodiment, the compound is

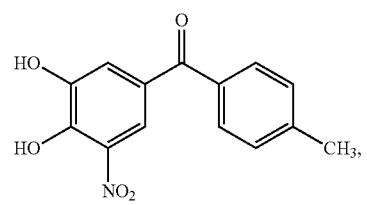

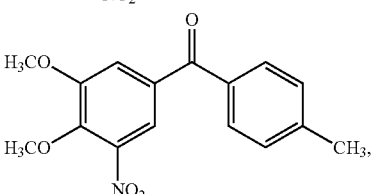

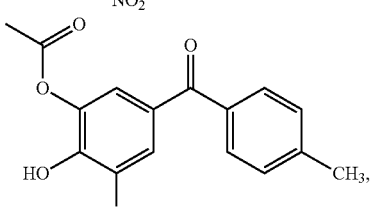

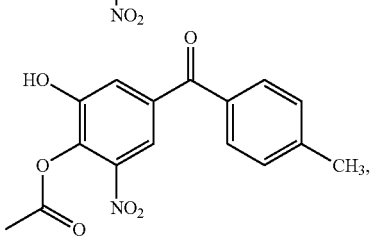

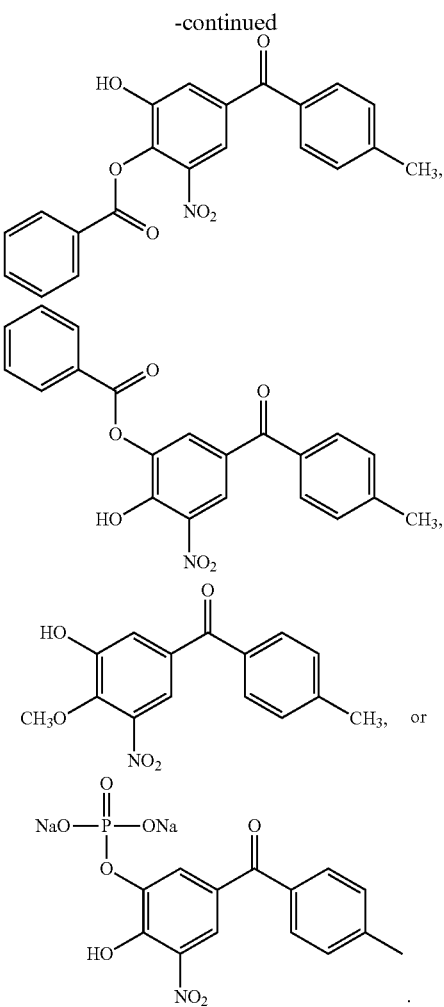

In another aspect, provided herein is a method for treating presbyopia or cataract in a subject in need thereof. The method comprises administering to the subject an effective amount of a composition comprising a compound having the formula (I)

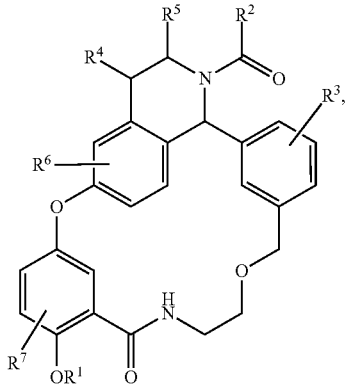

or a solvate or a pharmaceutically acceptable salt thereof, wherein $R^1$ is $R^8$ or $R^8C=O$, wherein $R^8$ is selected from hydrogen, $(C_1-C_6)$alkyl and $(C_3-C_6)$cycloalkyl groups, wherein the alkyl and the cycloalkyl groups are optionally substituted with one or more fluorine atoms;

$R^2$ is aryl, $(C_1-C_3)$alkylaryl, heteroaryl, $(C_1-C_3)$alkylheteroarylalkyl, $(C_1-C_3)$alkylheterocyclyl, each of which is optionally substituted with up to 3 groups independently selected from $R^{11}$;

$R^3$, $R^4$, $R^5$, $R^6$, and $R^7$, are independently selected from hydrogen, $R^9$, $OR^9$, $N(R^9)(R^{10})$, halogen, CN, $NO_2$, $C(O)OR^9$, $CON(R^9)(R^{10})$, $S(O)NR^9{}_2$, $SO_3H$, $SO_2CH_3$, phenyl, biphenyl, phenoxy-phenyl, and polyethyleneglycol groups, wherein $R^9$ and $R^{10}$ are independently selected from hydrogen atom, $(C_1-C_6)$alkyl, halo$(C_1-C_6)$alkyl, $(C_3-C_6)$cycloalkyl, halo$(C_3-C_6)$cycloalkyl, $(C_3-C_6)$cycloalkyl$(C_1-C_6)$alkyl, halo$(C_3-C_6)$cycloalkyl$(C_1-C_6)$alkyl, and $(C_3-C_6)$cycloalkylhalo$(C_1-C_6)$alkyl groups; wherein $R^3$, $R^6$, and $R^7$ can occupy 0-2 positions in their respective rings; and wherein, in the event any two adjacent groups selected from $R^3$, $R^4$, $R^5$, $R^6$, and $R^7$ are $OR^9$ groups, the two $OR^9$ groups may optionally be cross-linked via their $R^9$ functionalities to form an additional ring; and $R^{11}$ is selected from the group consisting of oxo, halo, cyano, nitro, amino, hydroxy, carboxy, $(C_1-C_6)$alkyl, halo$(C_1-C_6)$alkyl, hydroxy$(C_1-C_6)$alkyl, $(C_3-C_6)$cycloalkyl, halo$(C_3-C_6)$cycloalkyl, hydroxy$(C_3-C_6)$cycloalkyl, heterocyclyl, aryl, arylalkyl, heteroaryl, $(C_1-C_6)$alkylheteroaryl, halo$(C_1-C_6)$alkylheteroaryl, hydroxy$(C_1-C_6)$alkylheteroaryl, $(C_3-C_6)$cycloalkylheteroaryl, halo$(C_3-C_6)$cycloalkylheteroaryl, hydroxy$(C_3-C_6)$cycloalkylheteroaryl, heterocyclylheteroaryl, $(C_1-C_6)$alkyl heterocyclylheteroaryl, halo$(C_1-C_6)$alkyl heterocyclylheteroaryl, hydroxy$(C_1-C_6)$alkyl heterocyclylheteroaryl, heteroalkyl, heterocyclylalkyl, $(CH_2)_{1-3}$COOH, $(C_1-C_3)$alkylcarbonyloxy, $(C_3-C_6)$cycloalkyl$(C_1-C_6)$alkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_3-C_6)$cycloalkyl$(C_1-C_6)$alkyl, $(C_1-C_6)$alkoxy, $(C_3-C_6)$cycloalkoxy, $(C_3-C_6)$cycloalkyl$(C_1-C_6)$alkoxy, halo$(C_1-C_6)$alkoxy, halo$(C_3-C_6)$cycloalkoxy, halo$(C_3-C_6)$cycloalkyl$(C_1-C_6)$alkoxy, $(C_1-C_6)$alkylthio, $(C_3-C_6)$cycloalkylthio, $(C_3-C_6)$cycloalkyl$(C_1-C_6)$alkylthio, halo$(C_1-C_6)$alkylthio, halo$(C_3-C_6)$cycloalkythio, halo$(C_3-C_6)$cycloalkyl$(C_1-C_6)$alkylthio, $(C_1-C_6)$alkylsulfinyl, $(C_3-C_6)$cycloalkylsulfinyl, $(C_3-C_6)$cycloalkyl$(C_1-C_6)$alkylsulfinyl, halo$(C_1-C_6)$alkylsulfinyl, halo$(C_3-C_6)$cycloalkylsulfinyl, halo$(C_3-C_6)$cycloalkyl$(C_1-C_6)$alkylsulfinyl, $(C_1-C_6)$alkylsulfonyl, $(C_3-C_6)$cycloalkylsulfonyl, $(C_3-C_6)$cycloalkyl$(C_1-C_6)$alkylsulfonyl, halo$(C_1-C_6)$alkylsulfonyl, halo$(C_3-C_6)$cycloalkylsulfonyl, halo$(C_3-C_6)$cycloalkyl$(C_1-C_6)$alkylsulfonyl, $(C_1-C_6)$alkylamino, di$(C_1-C_6)$alkylamino, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, and $(C_1-C_3)$alkoxy$(C_1-C_3)$alkylaminocarbonyl.

In one embodiment of the method requiring the compound having formula (I), $R^7$ is hydrogen. In another embodiment $R^6$ is hydrogen. In yet another embodiment, $R^3$ is hydrogen.

In one embodiment, $R^5$ is hydrogen. In one embodiment, $R^4$ is hydrogen. In one embodiment, $R^2$ is a heteroaryl having one ring nitrogen. In one embodiment, $R^2$ is a heteroaryl having two ring nitrogen atoms. In one embodiment, $R^2$ is a heteroaryl having one or two ring nitrogen, the ring optionally substituted with up to two $(C_1-C_6)$alkyl groups. In one embodiment, $R^2$ is a heteroaryl having one or two ring nitrogen, the ring optionally substituted with up to two $(C_1-C_6)$alkyl groups and an oxo group. In one embodiment, the compound is one of

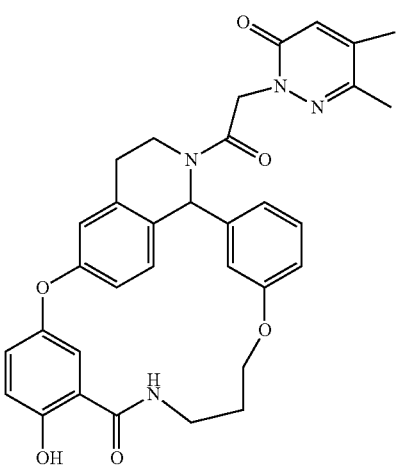

and

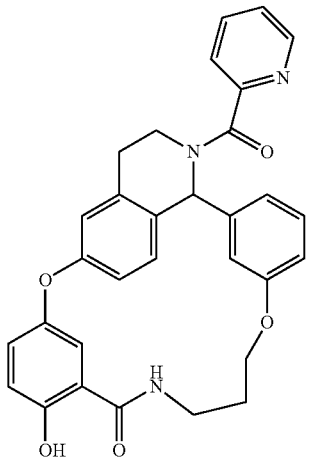

In yet another aspect, provided herein is a method for treating presbyopia or cataract in a subject in need thereof. The method comprises administering to the subject an effective amount of a composition comprising a compound having the formula (II)

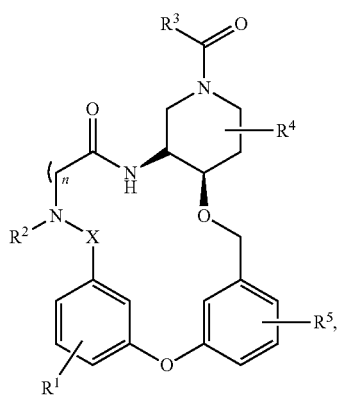

(II)

or a solvate or a pharmaceutically acceptable salt thereof, wherein

X is $CH_2$ or $C=O$ n is 1 or 2

$R^1$, $R^4$, and $R^5$ are independently selected from hydrogen, $R^6$, $OR^6$, $N(R^6)(R^7)$, halide, CN, $NO_2$, $C(O)OR^6$, $CON(R^6)$ ($R^7$), $S(O)NR^6{}_2$, $SO_3H$, $SO_2CH_3$, phenyl, biphenyl, phenoxy-phenyl, and polyethyleneglycol groups, wherein $R^6$ and $R^7$ are independently selected from hydrogen, $(C_1-C_6)$ alkyl, halo$(C_1-C_6)$alkyl, $(C_3-C_6)$cycloalkyl, halo$(C_3-C_6)$cycloalkyl, $(C_3-C_6)$cycloalkyl$(C_1-C_6)$alkyl, halo$(C_3-C_6)$cycloalkyl$(C_1-C_6)$alkyl, and $(C_3-C_6)$cycloalkylhalo$(C_1-C_6)$ alkyl groups; wherein $R^1$, $R^4$, and $R^5$ can occupy 0-2 positions in their respective ring; and wherein, in the event any two adjacent groups selected from $R^1$, $R^4$, and $R^5$, are $OR^6$ groups, the two $OR^6$ groups may optionally be cross-linked via their $R^6$ functionalities to form an additional ring; and $R^2$ is selected from the group consisting of hydrogen, $(C_1-C_6)$alkyl, halo$(C_1-C_6)$alkyl, hydroxy$(C_1-C_6)$alkyl, $(C_3-C_6)$cycloalkyl, halo$(C_3-C_6)$cycloalkyl, hydroxy$(C_3-C_6)$cycloalkyl, and $(C_1-C_6)$alkoxy$(C_1-C_6)$alkyl group;

$R^3$ is aryl, heteroaryl or heterocyclyl, each of which is optionally substituted with up to 3 groups independently selected from $R^8$; and $R^8$ is selected from the group consisting of oxo, halo, cyano, nitro, amino, hydroxy, carboxy, $(C_1-C_6)$alkyl, halo $(C_1-C_6)$alkyl, hydroxy$(C_1-C_6)$alkyl, $(C_3-C_6)$cycloalkyl, halo $(C_3-C_6)$cycloalkyl, hydroxy$(C_3-C_6)$cycloalkyl, heterocyclyl, aryl, arylalkyl, heteroaryl, $(C_1-C_6)$alkylheteroaryl, halo$(C_1-C_6)$alkylheteroaryl, hydroxy$(C_1-C_6)$alkylheteroaryl, $(C_3-C_6)$ cycloalkylheteroaryl, halo$(C_3-C_6)$cycloalkylheteroaryl, hydroxy$(C_3-C_6)$cycloalkylheteroaryl, heterocyclylheteroaryl, $(C_1-C_6)$alkyl heterocyclylheteroaryl, halo$(C_1-C_6)$ alkyl heterocyclylheteroaryl, hydroxy$(C_1-C_6)$alkyl heterocyclylheteroaryl, heteroalkyl, heterocyclylalkyl, $(CH_2)_{1-3}$ COOH, $(C_1-C_3)$alkylcarbonyloxy, $(C_3-C_6)$cycloalkyl$(C_1-C_6)$alkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_3-C_6)$cycloalkyl$(C_1-C_6)$alkyl, $(C_1-C_6)$alkoxy, $(C_3-C_6)$cycloalkoxy, $(C_3-C_6)$cycloalkyl$(C_1-C_6)$alkoxy, halo $(C_1-C_6)$alkoxy, halo$(C_3-C_6)$cycloalkoxy, halo$(C_3-C_6)$cycloalkyl$(C_1-C_6)$alkoxy, $(C_1-C_6)$alkylthio, $(C_3-C_6)$cycloalkylthio, $(C_3-C_6)$cycloalkyl$(C_1-C_6)$alkylthio, halo$(C_1-C_6)$ alkylthio, halo$(C_3-C_6)$cycloalkythio, halo$(C_3-C_6)$cycloalkyl $(C_1-C_6)$alkylthio, $(C_1-C_6)$alkylsulfinyl, $(C_3-C_6)$ cycloalkylsulfinyl, $(C_3-C_6)$cycloalkyl$(C_1-C_6)$alkylsulfinyl, halo$(C_1-C_6)$alkylsulfinyl, halo$(C_3-C_6)$cycloalkylsulfinyl, halo$(C_3-C_6)$cycloalkyl$(C_1-C_6)$alkylsulfinyl, $(C_1-C_6)$alkylsulfonyl, $(C_3-C_6)$cycloalkylsulfonyl, $(C_3-C_6)$cycloalkyl $(C_1-C_6)$alkylsulfonyl, halo$(C_1-C_6)$alkylsulfonyl, halo$(C_3-C_6)$cycloalkylsulfonyl, halo$(C_3-C_6)$cycloalkyl$(C_1-C_6)$ alkylsulfonyl, $(C_1-C_6)$alkylamino, di$(C_1-C_6)$alkylamino, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, and $(C_1-C_3)$ alkoxy$(C_1-C_3)$alkylaminocarbonyl.

In one embodiment of the method requiring the compound having formula (II), $R^1$ is a $(C_3-C_6)$cycloalkyl, and substitutes one or two ring hydrogen atoms. In one embodiment, $R^1$ is a cyclopropyl, and substitutes one ring hydrogen atom. In one embodiment, $R^1$ is a $(C_3-C_6)$cycloalkyl$(C_1-C_6)$ alkyl. In one embodiment, $R^1$ is cyclopropylmethyl. In one embodiment, $R^5$ is hydrogen. In one embodiment, $R^5$ is hydrogen, and $R^1$ is a $(C_3-C_6)$cycloalkyl, and substitutes one or two ring hydrogen atoms. In one embodiment, $R^5$ is hydrogen and $R^1$ is a $(C_3-C_6)$cycloalkyl$(C_1-C_6)$alkyl. In one embodiment, X is $CH_2$ and $R^2$ is $(C_1-C_6)$alkoxy$(C_1-C_6)$alkyl group. In one embodiment, $R^3$ is an aryl. In one embodiment, $R^3$ is a heteroaryl. In one embodiment, the compound is one of

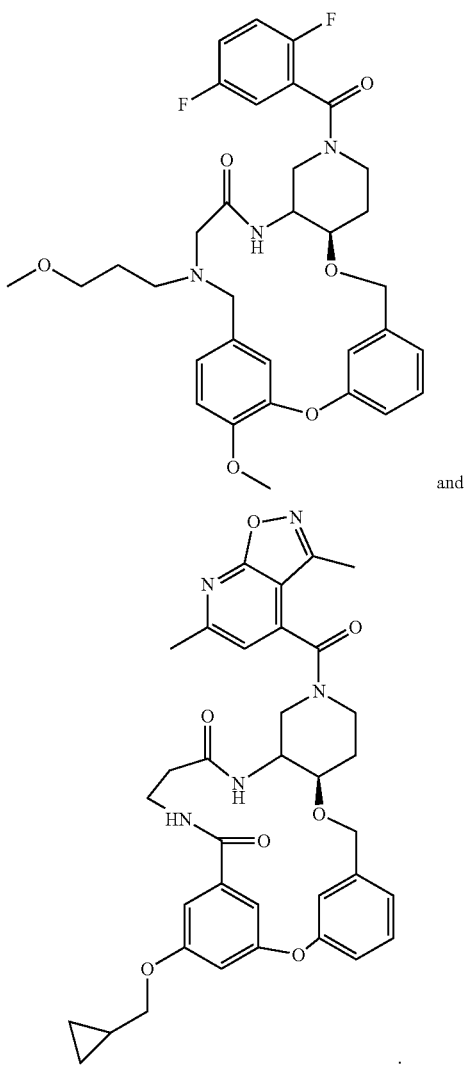

and

In another aspect, provided herein is a method for treating presbyopia or cataract in a subject in need thereof. The method comprises administering to the subject an effective amount of a composition comprising a compound having the formula (III)

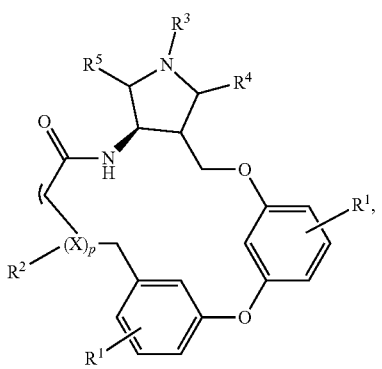

or a solvate or a pharmaceutically acceptable salt thereof, wherein

X is N;
p is 0 or 1;
n is 0, 1, or 2;

$R^1$, $R^4$, and $R^5$ are independently selected from hydrogen $R^6$, $OR^6$, $N(R^6)(R^7)$, halide, CN, $NO_2$, $C(O)OR^6$, $CON(R^6)(R^7)$, $S(O)NR^6{}_2$, $SO_3H$, $SO_2CH_3$, phenyl, biphenyl, phenoxy-phenyl, and polyethyleneglycol groups, wherein $R^6$ and $R^7$ are independently selected from hydrogen atom, $(C_1-C_6)$alkyl, halo$(C_1-C_6)$alkyl, $(C_3-C_6)$cycloalkyl, halo$(C_3-C_6)$cycloalkyl, $(C_3-C_6)$cycloalkyl$(C_1-C_6)$alkyl, halo$(C_3-C_6)$cycloalkyl$(C_1-C_6)$alkyl, and $(C_3-C_6)$cycloalkylhalo$(C_1-C_6)$alkyl groups; wherein $R^1$, $R^4$, and $R^5$ can occupy 0-2 positions in their respective ring; and wherein, in the event any two adjacent groups selected from $R^1$, $R^4$, and $R^5$, are $OR^6$ groups, the two $OR^6$ groups may optionally be cross-linked via their $R^6$ functionalities to form an additional ring;

$R^2$ is selected from the group consisting of hydrogen, $(C_1-C_6)$alkyl, halo$(C_1-C_6)$alkyl, hydroxy$(C_1-C_6)$alkyl, $(C_3-C_6)$cycloalkyl, halo$(C_3-C_6)$cycloalkyl, hydroxy$(C_3-C_6)$cycloalkyl, and $(C_1-C_6)$alkoxy$(C_1-C_6)$alkyl;

$R^3$ is one of hydrogen, $R^8$ and $SO_2R^8$, wherein $R^8$ is selected from the group consisting of aryl, heteroaryl or heterocyclyl, each of which is optionally substituted with up to 3 groups independently selected from $R^9$;

$R^9$ is selected from the group consisting of oxo, halo, cyano, nitro, amino, hydroxy, carboxy, $(C_1-C_6)$alkyl, halo$(C_1-C_6)$alkyl, hydroxy$(C_1-C_6)$alkyl, $(C_3-C_6)$cycloalkyl, halo$(C_3-C_6)$cycloalkyl, hydroxy$(C_3-C_6)$cycloalkyl, heterocyclyl, aryl, arylalkyl, heteroaryl, $(C_1-C_6)$alkylheteroaryl, halo$(C_1-C_6)$alkylheteroaryl, hydroxy$(C_1-C_6)$alkylheteroaryl, $(C_3-C_6)$cycloalkylheteroaryl, halo$(C_3-C_6)$cycloalkylheteroaryl, hydroxy$(C_3-C_6)$cycloalkylheteroaryl, heterocyclylheteroaryl, $(C_1-C_6)$alkyl heterocyclylheteroaryl, halo$(C_1-C_6)$alkyl heterocyclylheteroaryl, hydroxy$(C_1-C_6)$alkyl heterocyclylheteroaryl, heteroalkyl, heterocyclylalkyl, $(CH_2)_{1-3}$COOH, $(C_1-C_3)$alkylcarbonyloxy, $(C_3-C_6)$cycloalkyl$(C_1-C_6)$alkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_3-C_6)$cycloalkyl$(C_1-C_6)$alkyl, $(C_1-C_6)$alkoxy, $(C_3-C_6)$cycloalkoxy, $(C_3-C_6)$cycloalkyl$(C_1-C_6)$alkoxy, halo$(C_1-C_6)$alkoxy, halo$(C_3-C_6)$cycloalkoxy, halo$(C_3-C_6)$cycloalkyl$(C_1-C_6)$alkoxy, $(C_1-C_6)$alkylthio, $(C_3-C_6)$cycloalkylthio, $(C_3-C_6)$cycloalkyl$(C_1-C_6)$alkylthio, halo$(C_1-C_6)$alkylthio, halo$(C_3-C_6)$cycloalkythio, halo$(C_3-C_6)$cycloalkyl$(C_1-C_6)$alkylthio, $(C_1-C_6)$alkylsulfinyl, $(C_3-C_6)$cycloalkylsulfinyl, $(C_3-C_6)$cycloalkyl$(C_1-C_6)$alkylsulfinyl, halo$(C_1-C_6)$alkylsulfinyl, halo$(C_3-C_6)$cycloalkylsulfinyl, halo$(C_3-C_6)$cycloalkyl$(C_1-C_6)$alkylsulfinyl, $(C_1-C_6)$alkylsulfonyl, $(C_3-C_6)$cycloalkylsulfonyl, $(C_3-C_6)$cycloalkyl$(C_1-C_6)$alkylsulfonyl, halo$(C_1-C_6)$alkylsulfonyl, halo$(C_3-C_6)$cycloalkylsulfonyl, halo$(C_3-C_6)$cycloalkyl$(C_1-C_6)$alkylsulfonyl, $(C_1-C_6)$alkylamino, di$(C_1-C_6)$alkylamino, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, and $(C_1-C_3)$alkoxy$(C_1-C_3)$alkylaminocarbonyl.

In one embodiment of the method requiring the compound having formula (III), $R^1$ is hydrogen. In one embodiment, $R^1$ is hydrogen and each of p and n is zero. In one embodiment, X is N. In one embodiment, X is N and $R^2$ is a cyclopropyl. In one embodiment, each of $R^1$, $R^4$ and $R^5$ are hydrogen. In one embodiment, $R^3$ is a heteroaryl group. In one embodiment, $R^3$ is a heteroaryl substituted with a heterocyclyl group. In one embodiment, $R^3$ is $SO_2R^8$, wherein $R^8$ is a heteroaryl. In one embodiment, the compound is one of

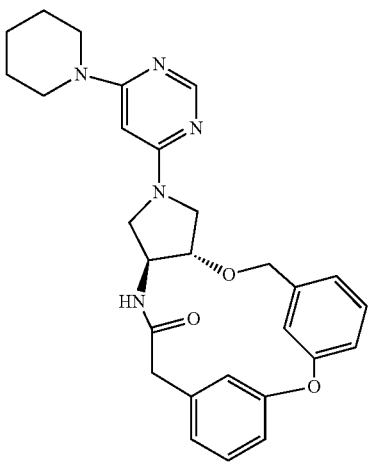

and

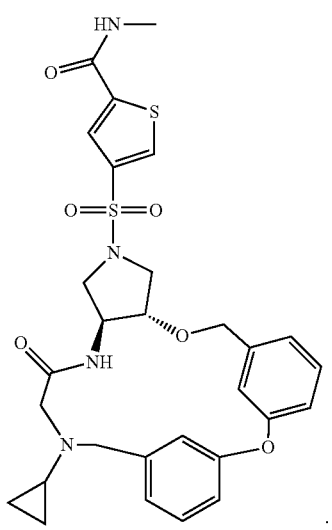

In another aspect, provided herein is a method for treating presbyopia or cataract in a subject in need thereof. The method comprises administering to the subject an effective amount of a composition comprising a compound having the formula (IV)

(IV)

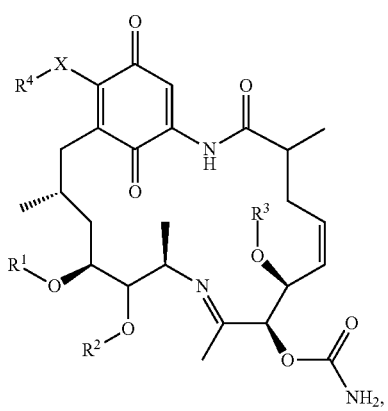

or a solvate or a pharmaceutically acceptable salt thereof, wherein $R^1$ and $R^3$ are independently hydrogen, $(C_1$-$C_3)$alkyl, halo$(C_1$-$C_3)$alkyl, $(C_3$-$C_6)$cycloalkyl, and halo$(C_3$-$C_6)$cycloalkyl;

$R^2$ is selected from the group consisting of hydrogen, $(C_1$-$C_3)$alkyl, halo$(C_1$-$C_3)$alkyl, $(C_3$-$C_6)$cycloalkyl, halo $(C_3$-$C_6)$cycloalkyl, and $R^5C$=O, wherein $R^5$ is selected from the $(C_1$-$C_6)$alkyl, halo$(C_1$-$C_6)$alkyl, $(C_3$-$C_6)$cycloalkyl, halo$(C_3$-$C_6)$cycloalkyl, aryl, and haloaryl;

X is O, S, or NH; and $R^4$ is selected from the group consisting of hydrogen, $(C_1$-$C_6)$alkyl, halo$(C_1$-$C_6)$alkyl, $(C_3$-$C_6)$cycloalkyl, halo $(C_3$-$C_6)$cycloalkyl, $(C_2$-$C_6)$alkenyl, halo$(C_2$-$C_6)$alkenyl, and hydroxy$(C_2$-$C_6)$alkenyl.

In one embodiment of the method requiring the compound having formula (IV), X is O. In one embodiment, X is NH. In one embodiment, X is NH and $R^4$ is $(C_2$-$C_6)$ alkenyl. In one embodiment, $R^1$ is a methyl. In one embodiment, $R^2$ is hydrogen. In one embodiment, $R^3$ is methyl. In one embodiment, the compound is one of

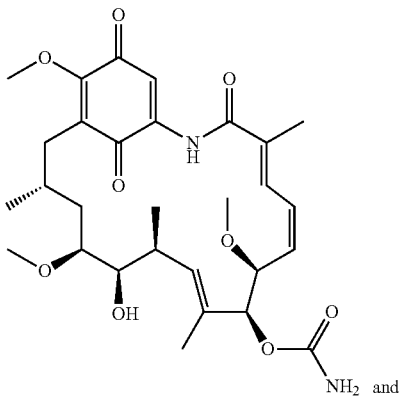

and

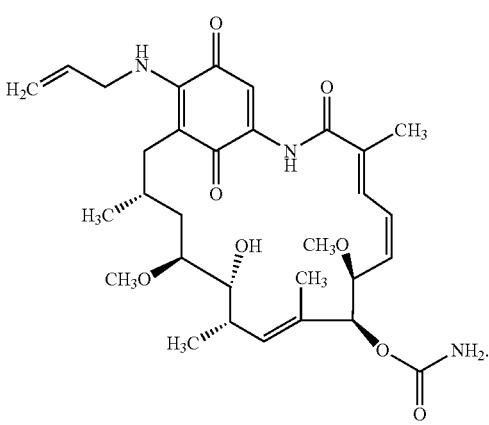

In another aspect, provided herein is a method for treating presbyopia or cataract in a subject in need thereof. The method comprises administering to the subject an effective amount of a composition comprising a compound having the formula (V)

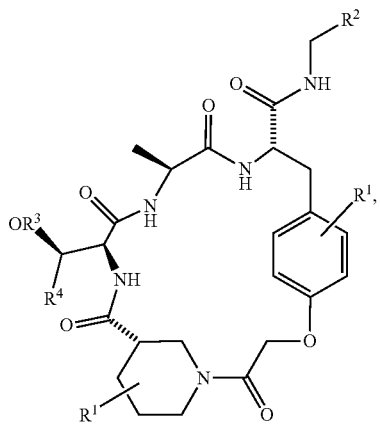

(V)

or a solvate or a pharmaceutically acceptable salt thereof, wherein $R^1$ is independently selected from hydrogen, $R^5$, $OR^5$, $N(R^5)(R^6)$, halide, CN, $NO_2$, $C(O)OR^5$, $CON(R^5)(R^6)$, $S(O)NR^6{}_2$, $SO_3H$, $SO_2CH_3$, phenyl, biphenyl, phenoxy-phenyl, and polyethyleneglycol groups, wherein $R^5$ and $R^6$ are independently selected from hydrogen, $(C_1-C_6)$alkyl, halo$(C_1-C_6)$alkyl, $(C_3-C_6)$cycloalkyl, halo$(C_3-C_6)$cycloalkyl, $(C_3-C_6)$cycloalkyl$(C_1-C_6)$alkyl, halo$(C_3-C_6)$cycloalkyl$(C_1-C_6)$alkyl, and $(C_3-C_6)$cycloalkylhalo$(C_1-C_6)$alkyl groups; wherein $R^1$ can occupy 0-2 positions in the ring of its occurrence; and wherein, in the event any two adjacent groups selected are $OR^5$ groups, the two $OR^5$ groups may optionally be cross-linked via their $R^5$ functionalities to form an additional ring;

$R^2$ is aryl, heteroaryl or heterocyclyl, each of which is optionally substituted with up to 3 groups independently selected from $R^7$;

$R^7$ is selected from the group consisting of oxo, halo, cyano, nitro, amino, hydroxy, carboxy, $(C_1-C_6)$alkyl, halo$(C_1-C_6)$alkyl, hydroxy$(C_1-C_6)$alkyl, $(C_3-C_6)$cycloalkyl, halo$(C_3-C_6)$cycloalkyl, hydroxy$(C_3-C_6)$cycloalkyl, heterocyclyl, aryl, arylalkyl, heteroaryl, $(C_1-C_6)$alkylheteroaryl, halo$(C_1-C_6)$alkylheteroaryl, hydroxy$(C_1-C_6)$alkylheteroaryl, $(C_3-C_6)$cycloalkylheteroaryl, halo$(C_3-C_6)$cycloalkylheteroaryl, hydroxy$(C_3-C_6)$cycloalkylheteroaryl, heterocyclylheteroaryl, $(C_1-C_6)$alkyl heterocyclylheteroaryl, halo$(C_1-C_6)$alkyl heterocyclylheteroaryl, hydroxy$(C_1-C_6)$alkyl heterocyclylheteroaryl, heteroalkyl, heterocyclylalkyl, $(CH_2)_{1-3}$COOH, $(C_1-C_3)$alkylcarbonyloxy, $(C_3-C_6)$cycloalkyl$(C_1-C_6)$alkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_3-C_6)$cycloalkyl$(C_1-C_6)$alkyl, $(C_1-C_6)$alkoxy, $(C_3-C_6)$cycloalkoxy, $(C_3-C_6)$cycloalkyl$(C_1-C_6)$alkoxy, halo$(C_1-C_6)$alkoxy, halo$(C_3-C_6)$cycloalkoxy, halo$(C_3-C_6)$cycloalkyl$(C_1-C_6)$alkoxy, $(C_1-C_6)$alkylthio, $(C_3-C_6)$cycloalkythio, $(C_3-C_6)$cycloalkyl$(C_1-C_6)$alkylthio, halo$(C_1-C_6)$alkylthio, halo$(C_3-C_6)$cycloalkythio, halo$(C_3-C_6)$cycloalkyl$(C_1-C_6)$alkylthio, $(C_1-C_6)$alkylsulfinyl, $(C_3-C_6)$cycloalkylsulfinyl, $(C_3-C_6)$cycloalkyl$(C_1-C_6)$alkylsulfinyl, halo$(C_1-C_6)$alkylsulfinyl, halo$(C_3-C_6)$cycloalkylsulfinyl, halo$(C_3-C_6)$cycloalkyl$(C_1-C_6)$alkylsulfinyl, $(C_1-C_6)$alkylsulfonyl, $(C_3-C_6)$cycloalkylsulfonyl, $(C_3-C_6)$cycloalkyl$(C_1-C_6)$alkylsulfonyl, halo$(C_1-C_6)$alkylsulfonyl, halo$(C_3-C_6)$cycloalkylsulfonyl, halo$(C_3-C_6)$cycloalkyl$(C_1-C_6)$alkylsulfonyl, $(C_1-C_6)$alkylamino, di$(C_1-C_6)$alkylamino, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, and $(C_1-C_3)$alkoxy$(C_1-C_3)$alkylaminocarbonyl;

$R^3$ is selected from the group consisting of hydrogen, $(C_1-C_3)$alkyl, halo$(C_1-C_3)$alkyl, $(C_3-C_6)$cycloalkyl, halo$(C_3-C_6)$cycloalkyl, and $R^8C{=}O$, wherein $R^8$ is selected from $(C_1-C_6)$alkyl, halo$(C_1-C_6)$alkyl, $(C_3-C_6)$cycloalkyl, halo$(C_3-C_6)$cycloalkyl, aryl, and haloaryl groups; and $R^4$ is selected from the group consisting of $(C_1-C_6)$alkyl, halo$(C_1-C_6)$alkyl, $(C_3-C_6)$cycloalkyl, halo$(C_3-C_6)$cycloalkyl, $(C_2-C_6)$alkenyl, halo$(C_2-C_6)$alkenyl, and hydroxy$(C_2-C_6)$alkenyl.

In one embodiment of the method requiring the compound having formula (V), $R^1$ is hydrogen. In one embodiment, $R^2$ is aryl. In one embodiment, $R^2$ is heteroaryl. In one embodiment, $R^4$ is $(C_1-C_6)$alkyl. In one embodiment, $R^3$ is hydrogen. In one embodiment, the compound is

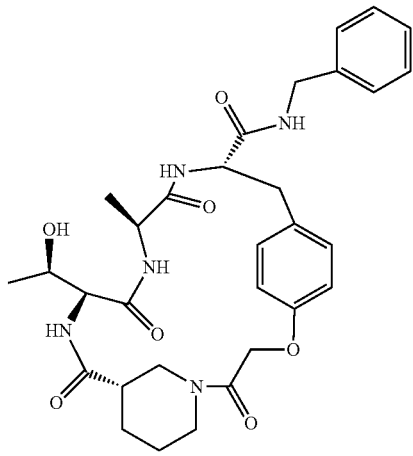

or

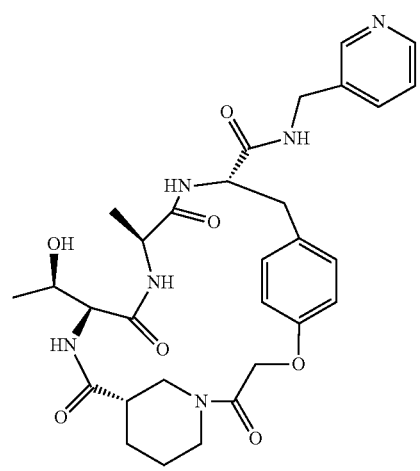

In another aspect, provided herein is a method for treating presbyopia or cataract in a subject in need thereof. The method comprises administering to the subject an effective amount of a composition comprising a compound having the formula (VI)

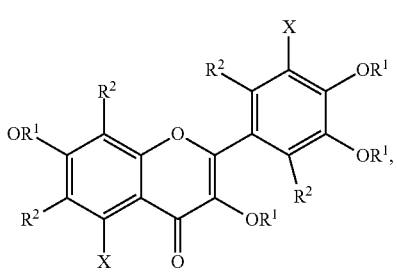
(VI)

or a solvate or a pharmaceutically acceptable salt thereof, wherein

X is H or $OR^1$;

$R^1$ is independently selected from the group consisting of hydrogen, $(C_1-C_3)$alkyl, halo$(C_1-C_3)$alkyl, $(C_3-C_6)$cycloalkyl, halo$(C_3-C_6)$cycloalkyl, and $R^3C{=}O$, wherein $R^3$ is selected from $(C_1-C_6)$alkyl, halo$(C_1-C_6)$alkyl, $(C_3-C_6)$cycloalkyl, halo$(C_3-C_6)$cycloalkyl, aryl, and haloaryl groups; and $R^2$ is independently selected from hydrogen, $R^4$, $OR^4$, $N(R^4)(R^5)$, halide, CN, $NO_2$, $C(O)OR^4$, $CON(R^4)(R^4)$, $S(O)NR^4{}_2$, $SO_3H$, $SO_2CH_3$, phenyl, biphenyl, phenoxy-phenyl, and polyethyleneglycol groups, wherein $R^4$ and $R^5$ are independently selected from hydrogen, $(C_1-C_6)$alkyl, halo$(C_1-C_6)$alkyl, $(C_3-C_6)$cycloalkyl, halo$(C_3-C_6)$cycloalkyl, $(C_3-C_6)$cycloalkyl$(C_1-C_6)$alkyl, halo$(C_3-C_6)$cycloalkyl$(C_1-C_6)$alkyl, and $(C_3-C_6)$cycloalkylhalo$(C_1-C_6)$alkyl groups; wherein $R^2$ can occupy 0-2 positions in the ring of its occurrence.

In one embodiment of the method requiring the compound having formula (VI), in the unfused benzene ring, X is a hydrogen. In one embodiment, in the unfused benzene ring, X is a hydroxyl. In one embodiment, $R^1$ is hydrogen. In one embodiment, $R^2$ is hydrogen. In one embodiment, the compound is one of

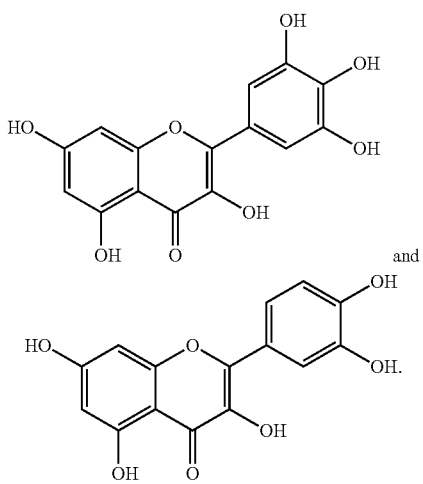

In another aspect, provided herein is a method for treating presbyopia or cataract in a subject in need thereof. The method comprises administering to the subject an effective amount of a composition comprising a compound having the formula (VIII)

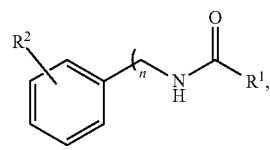
(VIII)

or a solvate or a pharmaceutically acceptable salt thereof, wherein $R^1$ is selected from hydrogen, halogen, hydroxyl, $(C_1-C_6)$alkyl, halo$(C_1-C_6)$alkyl, $(C_3-C_6)$cycloalkyl, halo$(C_3-C_6)$cycloalkyl, $(C_2-C_6)$alkenyl, and halo$(C_2-C_6)$alkenyl;

$R^2$ is selected from hydrogen, $R^3$, $OR^3$, $N(R^3)(R^4)$, halide, CN, $NO_2$, $C(O)OR^3$, $CON(R^3)(R^4)$, $S(O)NR^3{}_2$, $SO_3H$, $SO_2CH_3$, phenyl, biphenyl, phenoxy-phenyl, and polyethyleneglycol groups, wherein $R^3$ and $R^4$ are independently selected from hydrogen atom, $(C_1-C_6)$alkyl, halo$(C_1-C_6)$alkyl, $(C_3-C_6)$cycloalkyl, halo$(C_3-C_6)$cycloalkyl, $(C_3-C_6)$cycloalkyl$(C_1-C_6)$alkyl, halo$(C_3-C_6)$cycloalkyl$(C_1-C_6)$alkyl, and $(C_3-C_6)$cycloalkylhalo$(C_1-C_6)$alkyl groups; wherein $R^2$ can occupy 0-2 positions in the ring; and wherein, in the event any two adjacent groups selected are $OR^3$ groups, the two $OR^3$ groups may optionally be cross-linked via their $R^3$ functionalities to form an additional ring; and n is an integer between 0 and 4.

In one embodiment of the method requiring the compound having formula (VIII), $R^1$ is a halogen atom. In one embodiment, $R^1$ is a $(C_2-C_6)$alkenyl. In one embodiment, $R^2$ is a halogen atom. In one embodiment, each of $R^1$ and $R^2$ is a halogen atom. In one embodiment, the compound is one of

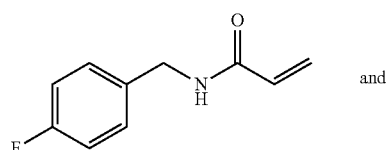

and

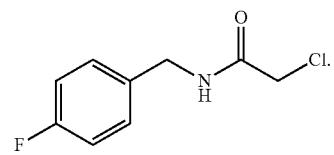

In another aspect, provided herein is a method for treating presbyopia or cataract in a subject in need thereof. The method comprises administering to the subject an effective amount of a composition comprising a compound having the formula (IX)

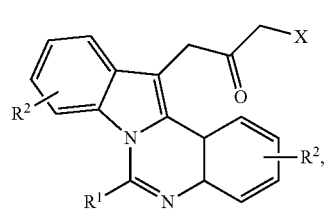
(IX)

or a solvate or a pharmaceutically acceptable salt thereof, wherein

R¹ is selected from the group consisting of hydrogen, $(C_1-C_6)$alkyl, halo$(C_1-C_6)$alkyl, $(C_3-C_6)$cycloalkyl, halo $(C_3-C_6)$cycloalkyl, $(C_2-C_6)$alkenyl, halo$(C_2-C_6)$alkenyl, and hydroxy$(C_2-C_6)$alkenyl;

X is a hydrogen, halogen, hydroxy or, $(C_1-C_6)$alkyl; and

R² is selected from hydrogen, R³, OR⁴, N(R³)(R⁴), halide, CN, NO₂, C(O)OR³, CON(R³)(R⁴), S(O)NR³₂, SO₃H, SO₂CH₃, phenyl, biphenyl, phenoxy-phenyl, and polyethyleneglycol groups, wherein R³ and R⁴ are independently selected from hydrogen atom, $(C_1-C_6)$alkyl, halo$(C_1-C_6)$alkyl, $(C_3-C_6)$cycloalkyl, halo$(C_3-C_6)$cycloalkyl, $(C_3-C_6)$cycloalkyl$(C_1-C_6)$alkyl, halo$(C_3-C_6)$cycloalkyl$(C_1-C_6)$alkyl, and $(C_3-C_6)$cycloalkylhalo$(C_1-C_6)$alkyl groups; wherein R² can occupy 0-2 positions in the ring of its occurrence; and wherein, in the event any two adjacent groups selected are OR³ groups, the two OR³ groups may optionally be cross-linked via their R³ functionalities to form an additional ring.

In one embodiment of the method requiring the compound having formula (IX), X is a halogen. In one embodiment, R¹ is an alkyl. In one embodiment, R² is hydrogen. In one embodiment, the compound is

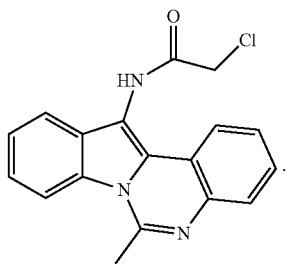 [SMILES: Cc1nc2ccccc2c2c(NC(=O)CCl)c3ccccc3n12]

In another aspect, provided herein is a method for treating presbyopia or cataract in a subject in need thereof. The method comprises administering to the subject an effective amount of a composition comprising a compound having the formula (X)

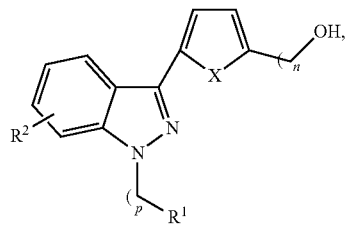

(X)

or a solvate or a pharmaceutically acceptable salt thereof, wherein,

X is O, S, or N;

each of n and p is an integer between 1 and 3;

R¹ is aryl, heteroaryl, cyclyl, or heterocycyl, each of which is optionally substituted with up to 3 groups independently selected from R³;

R² is selected from a group consisting of hydrogen R⁴, OR⁴, N(R⁴)(R⁵), halide, CN, NO₂, C(O)OR⁴, CON(R⁴)(R⁵), S(O)NR⁴₂, SO₃H, SO₂CH₃, phenyl, biphenyl, phenoxy-phenyl, and polyethyleneglycol groups, wherein R⁴ and R⁵ are independently selected from a group consisting of hydrogen, $(C_1-C_6)$alkyl, halo$(C_1-C_6)$alkyl, $(C_3-C_6)$cycloalkyl, halo$(C_3-C_6)$cycloalkyl, $(C_3-C_6)$cycloalkyl$(C_1-C_6)$alkyl, halo$(C_3-C_6)$cycloalkyl$(C_1-C_6)$alkyl, and $(C_3-C_6)$cycloalkyl-halo$(C_1-C_6)$alkyl groups; wherein R² can occupy 0-2 positions in the ring; and wherein, in the event any two adjacent groups selected are OR⁴ groups, the two OR⁴ groups may optionally be cross-linked via their R⁴ functionalities to form an additional ring; and R³ is selected from the group consisting of $(C_1-C_3)$alkyl, halo$(C_1-C_3)$alkyl, $(C_3-C_6)$cycloalkyl, halo$(C_3-C_6)$cycloalkyl, and R⁶C=O, wherein R⁶ is selected from the $(C_1-C_6)$ alkyl, halo$(C_1-C_6)$alkyl, $(C_3-C_6)$cycloalkyl, halo$(C_3-C_6)$cycloalkyl, aryl, and haloaryl.

In one embodiment of the method requiring the compound having formula (X), X is an oxygen atom. In one embodiment, X is an oxygen atom and each of n and p is 1. In one embodiment, R¹ is an aryl. In one embodiment, R is hydrogen. In one embodiment, the compound is

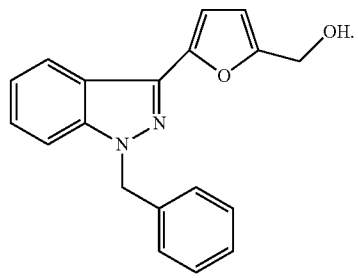 [SMILES: OCc1ccc(-c2nn(Cc3ccccc3)c3ccccc23)o1]

In another aspect, provided herein is a method for treating presbyopia or cataract in a subject in need thereof. The method comprises administering to the subject an effective amount of a composition comprising a compound having the formula (XI)

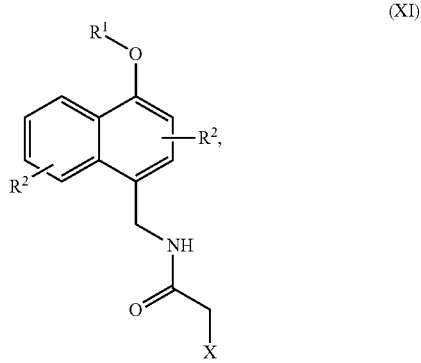

(XI)

or a solvate or a pharmaceutically acceptable salt thereof wherein

R¹ is selected from the group consisting of hydrogen $(C_1-C_3)$alkyl, halo$(C_1-C_3)$alkyl, $(C_3-C_6)$cycloalkyl, halo $(C_3-C_6)$cycloalkyl, and R³C=O, wherein R³ is selected from the $(C_1-C_6)$alkyl, halo$(C_1-C_6)$alkyl, $(C_3-C_6)$cycloalkyl, halo$(C_3-C_6)$cycloalkyl, aryl, and haloaryl;

X is a hydrogen, halogen, hydroxy or, $(C_1-C_6)$alkyl; and

R² is selected from the group consisting of hydrogen, R⁴, OR⁴, N(R⁴)(R⁵), halide, CN, NO₂, C(O)OR⁴, CON(R⁴)(R⁵), S(O)NR⁴₂, SO₃H, SO₂CH₃, phenyl, biphenyl, phenoxy-phenyl, and polyethyleneglycol groups, wherein R⁴ and R⁵ are independently selected from hydrogen atom, $(C_1-C_6)$ alkyl, halo($C_1$-$C_6$)alkyl, ($C_3$-$C_6$)cycloalkyl, halo($C_3$-$C_6$)cycloalkyl, ($C_3$-$C_6$)cycloalkyl($C_1$-$C_6$)alkyl, halo($C_3$-$C_6$)cycloalkyl($C_1$-$C_6$)alkyl, and ($C_3$-$C_6$)cycloalkylhalo($C_1$-$C_6$) alkyl groups; wherein $R^2$ can occupy 0-2 positions in the ring; and wherein, in the event any two adjacent groups selected are $OR^4$ groups, the two $OR^4$ groups may optionally be cross-linked via their $R^4$ functionalities to form an additional ring.

In one embodiment of the method requiring the compound having formula (XI), $R^1$ is a ($C_1$-$C_3$)alkyl. In one embodiment, $R^2$ is hydrogen. In one embodiment, X is a halogen. In one embodiment, the compound is

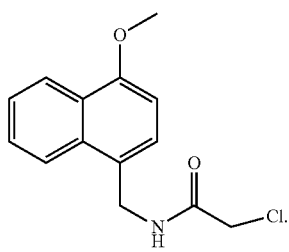 [SMILES: COc1ccc(CNC(=O)CCl)c2ccccc12]

In another aspect, provided herein is a method of treating presbyopia or cataract in a subject in need thereof. The method comprises administering to the subject an effective amount of a composition comprising a compound having the formula (XVII) or (XVIII)

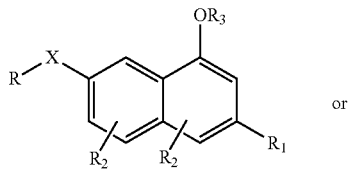

(XVII)

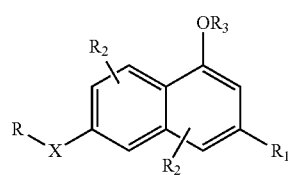

(XVIII)

or a solvate or a pharmaceutically acceptable salt thereof, wherein
R is

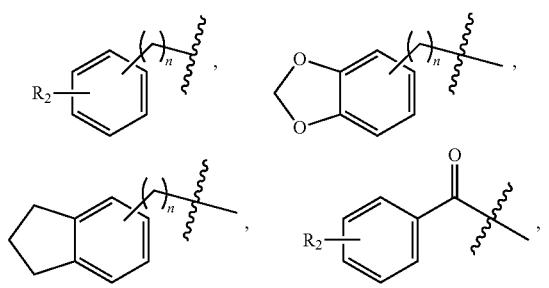

-continued

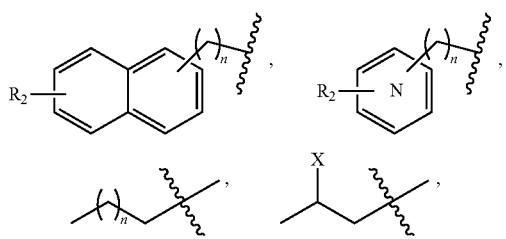

or OH;

$R_1$ is

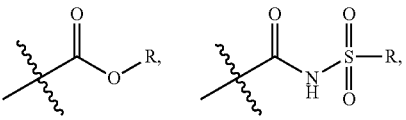

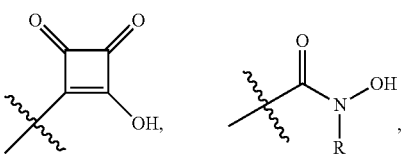

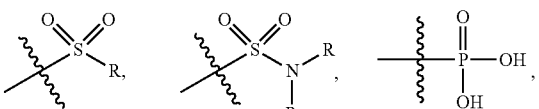

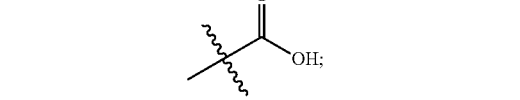

or $SO_3H$ $R_2$ is H, X—R, $CH_3$, lower alkyl, $OCH_3$, OH, F, Cl, Br, NR, —CN, $CO_2R$, $CH_2OH$, or $CF_3$.

R is OH,

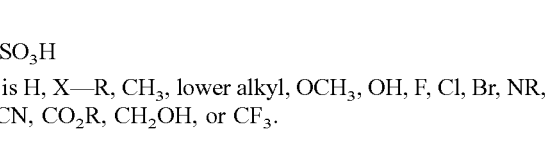

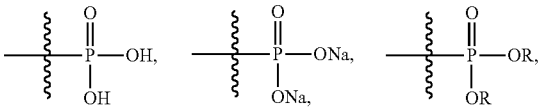

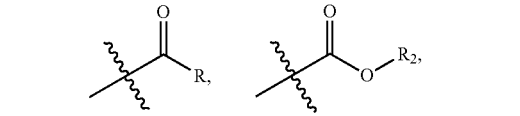

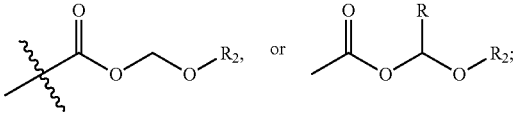

and

X is NH, O, S, $SO_2$, or N($C_1$-$C_6$)alkyl.

In one embodiment of the method requiring the compound having formula (XVII) or (XVIII), the compound is

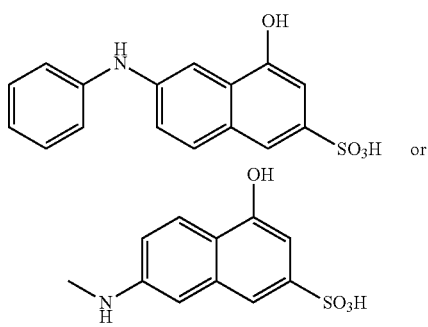

In another aspect, provided herein is a method of treating presbyopia or cataract in a subject in need thereof. The method comprises administering to the subject an effective amount of a composition comprising a compound having the formula (XII)

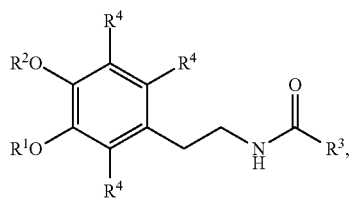

(XII)

or a solvate or a pharmaceutically acceptable salt thereof, wherein $R^1$ and $R^2$ are independently selected from the group consisting of hydrogen, $(C_1-C_3)$alkyl; halo$(C_1-C_3)$alkyl; $(C_3-C_7)$cycloalkyl; halo$(C_3-C_7)$cycloalkyl; and phenyl$(C_1-C_3)$alkyl, aminopheny$(C_1-C_3)$alkyl, and indanyl, wherein the phenyl or indanyl is optionally substituted with a halogen and the amino is optionally substituted with one or two $(C_1-C_3)$alkyl;

$R^3$ is selected from the group consisting of hydrogen, $(C_3-C_{10})$cycloalkyl; halo$(C_3-C_{10})$cycloalkyl; $(C_3-C_{10})$cycloalkyl$(C_1-C_6)$alkyl; halo$(C_3-C_{10})$cycloalkyl$(C_1-C_6)$alkyl; $(C_1-C_{20})$alkyl; halo$(C_1-C_{20})$alkyl; aryl; haloaryl; aryl$(C_1-C_6)$alkyl; haloaryl$(C_1-C_6)$alkyl; and $(C_3-C_{10})$heterocyclyl and halo$(C_3-C_{10})$heterocyclyl, each optionally substituted at the heteroatom with $R^7CO$, wherein $R^7$ is selected from the group consisting of $(C_1-C_6)$alkyl, halo$(C_1-C_6)$alkyl, $(C_3-C_{10})$cycloalkyl, halo$(C_3-C_{10})$cycloalkyl, aryl, haloaryl, aryl $(C_1-C_6)$alkyl, haloaryl$(C_1-C_6)$alkyl, $(C_1-C_6)$alkylaryl, and halo$(C_1-C_6)$alkylaryl; and $R^4$, at each position where it occurs, is independently selected from the group consisting of hydrogen; halogen; $(C_1-C_3)$alkyl; halo$(C_1-C_3)$alkyl; $(C_1-C_3)$alkoxy; halo$(C_1-C_3)$alkoxy; OH, thiol, amino, and nitro.

In one embodiment of the method requiring the compound having formula (XII), $R^4$ is hydrogen and each of $R^1$ and $R^2$ is a methyl group or a hydrogen. In a related embodiment, $R^4$ is hydrogen and $R^3$ is a six-member nitrogen containing a heterocyclyl group. Further, the nitrogen can be substituted with a phenylcarbonyl or benzylcarbonyl group, and the phenyl group can be optionally substituted with one or more fluorine atoms.

In one embodiment, $R^4$ is hydrogen and $R^3$ is a $(C_3-C_{10})$ cycloalkyl or a $(C_3-C_{10})$cycloalkyl$(C_1-C_3)$alkyl group. In a related embodiment, either $R^1$ or $R^2$ or both are hydrogen.

In one embodiment, the compound is selected from the group consisting of

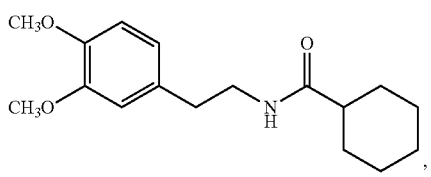

(CAP1222)

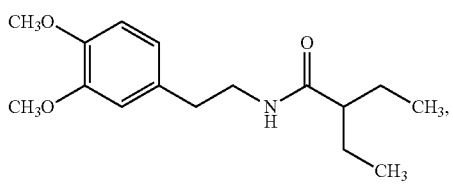

(CAP1223)

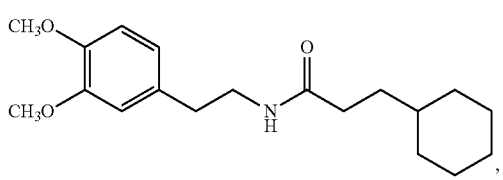

(CAP1224)

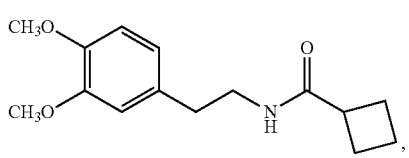

(CAP1226)

-continued
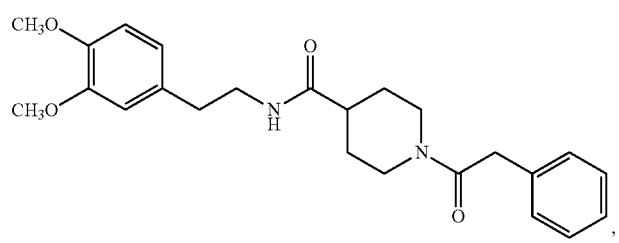
(CAP1227)
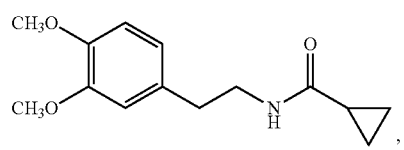
(CAP2130)
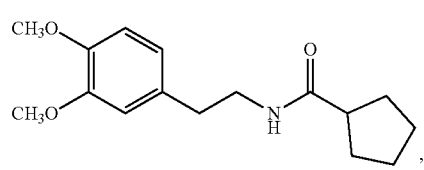
(CAP1231)
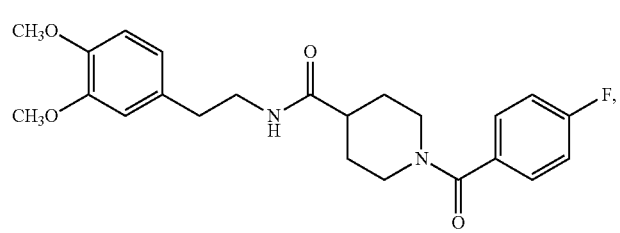
(CAP1232)
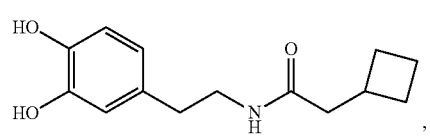
(CAP1239)
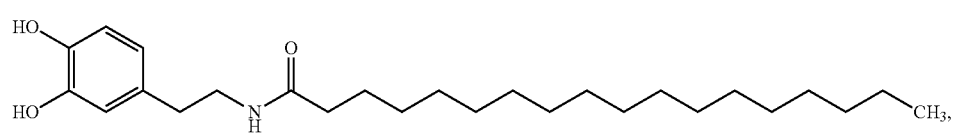
(CAP1241)
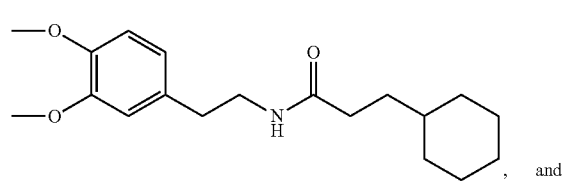
, and
(CAP1274)
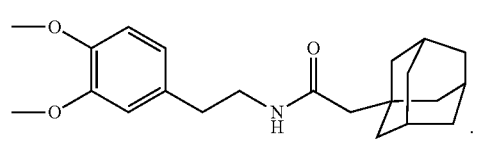
.
(CAP1281)

In another aspect, provided herein is a method of treating presbyopia or cataract in a subject in need thereof, the In one embodiment, the compound is selected from the group consisting of

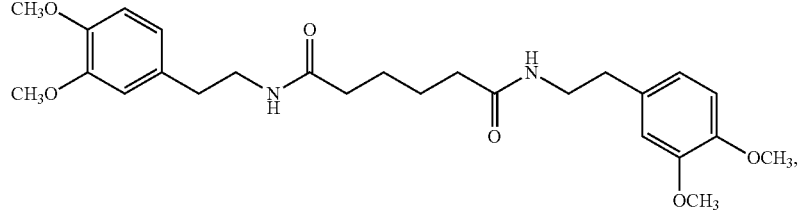
(CAP 1225)

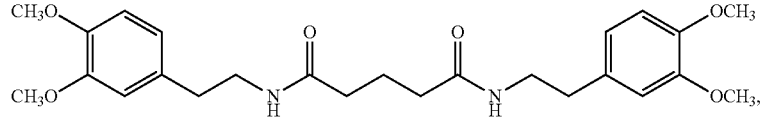
(CAP1228)

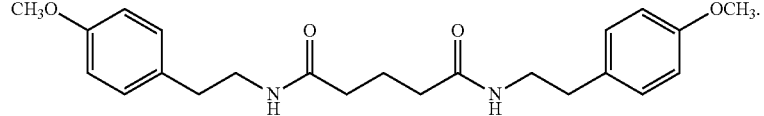
(CAP1129)

method comprising administering to the subject an effective amount of a composition comprising a compound having the formula (XIII)

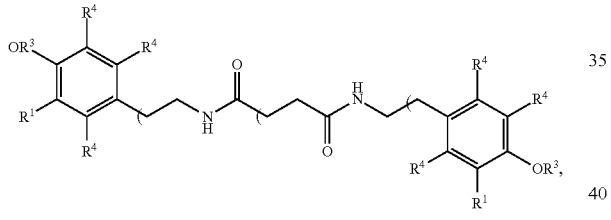
(XIII)

In another aspect, provided herein is a method of treating presbyopia or cataract in a subject in need thereof, the method comprising administering to the subject an effective amount of a composition comprising a compound having the formula (XIV)

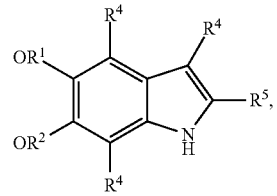
(XIV)

or a solvate or a pharmaceutically acceptable salt thereof, wherein $R^1$, at each position it occurs, is independently hydrogen or $OR^2$, wherein $R^2$ is selected from the group consisting of hydrogen, $(C_1-C_3)$alkyl; halo$(C_1-C_3)$alkyl; $(C_3-C_7)$cycloalkyl; halo$(C_3-C_7)$cycloalkyl; phenyl$(C_1-C_3)$alkyl, aminophenyl$(C_1-C_3)$alkyl, and indanyl, wherein the phenyl or indanyl is optionally substituted with a halogen and the amino is optionally substituted with one or two $(C_1-C_3)$alkyl;

$R^3$ is selected from the group consisting of hydrogen, $(C_1-C_3)$alkyl; halo$(C_1-C_3)$alkyl; $(C_3-C_7)$cycloalkyl; halo$(C_3-C_7)$cycloalkyl; phenyl$(C_1-C_3)$alkyl, aminophenyl$(C_1-C_3)$alkyl, and indanyl, wherein the phenyl or indanyl is optionally substituted with a halogen and the amino is optionally substituted with one or two $(C_1-C_3)$alkyl;

$R^4$, at each position it occurs, is independently selected from the group consisting of hydrogen; halogen; $(C_1-C_3)$alkyl; halo$(C_1-C_3)$alkyl; $(C_1-C_3)$alkoxy; halo$(C_1-C_3)$alkoxy; OH, thiol, amino, and nitro;

n is an integer between 0 and 5; and m is an integer between 0 and 3.

In one embodiment of the method requiring the compound having formula (XIII), one or both of $R^2$ and $R^3$ are methyl groups and n is 2 or 3. In a related embodiment, $R^4$ is hydrogen.

or a solvate or a pharmaceutically acceptable salt thereof, wherein $R^1$ and $R^2$ are independently selected from the group consisting of hydrogen, $(C_1-C_3)$alkyl; halo$(C_1-C_3)$alkyl; $(C_3-C_7)$cycloalkyl; halo$(C_3-C_7)$cycloalkyl; phenyl$(C_1-C_3)$alkyl, aminophenyl$(C_1-C_3)$alkyl, and indanyl, wherein the phenyl or indanyl is optionally substituted with a halogen and the amino is optionally substituted with one or two $(C_1-C_3)$alkyl; and $R^3CO$, wherein $R^3$ is selected from the group consisting of hydrogen, $(C_1-C_6)$alkyl, halo$(C_1-C_6)$alkyl, $(C_3-C_{10})$cycloalkyl, and halo$(C_3-C_{10})$cycloalkyl;

$R^4$, at each position that it occurs, is independently be selected from the group consisting of hydrogen; halogen; $(C_1-C_3)$alkyl; halo$(C_1-C_3)$alkyl; $(C_1-C_3)$alkoxy; halo$(C_1-C_3)$alkoxy; OH, thiol, amino, and nitro; and $R^5$ is selected from the group consisting of hydrogen, $(C_3-C_{10})$cycloalkyl; halo$(C_3-C_{10})$cycloalkyl; $(C_3-C_{10})$cycloalkyl$(C_1-C_6)$alkyl; halo$(C_3-C_{10})$cycloalkyl$(C_1-C_6)$alkyl; $(C_1-C_{20})$alkyl; halo$(C_1-C_{20})$alkyl; $(C_3-C_{10})$heterocyclyl and halo$(C_3-C_{10})$heterocyclyl, each optionally substituted at the heteroatom with $R^6CO$, wherein $R^6$ is selected from the group consisting of $(C_1-C_6)$alkyl, halo$(C_1-C_6)$alkyl, $(C_3-C_{10})$cycloalkyl, halo$(C_3-C_{10})$cycloalkyl, aryl, haloaryl, aryl$(C_1-C_6)$alkyl, haloaryl$(C_1-C_6)$alkyl, $(C_1-C_6)$alkylaryl, and halo$(C_1-C_6)$alkylaryl.

In one embodiment of the method requiring the compound having formula (XIV), each of $R^1$ and $R^2$ is a hydrogen, methyl or a $CH_3CO$ group and $R^4$ is hydrogen. In a related embodiment, each of $R^1$ and $R^2$ is a $CH_3CO$ group. In another related embodiment, each of $R^1$ and $R^2$ is a $CH_3$ group. In another related embodiment, each of $R^1$ and $R^2$ is a hydrogen. In another related embodiment, $R^5$ is a hydrogen or a carboxyl group.

In one embodiment, the compound is selected from the group consisting of

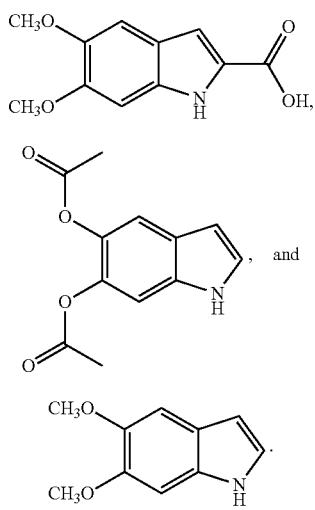

(CAP1447)

(CAP1517)

(CAP1519)

In another aspect, provided herein is a method of treating presbyopia or cataract in a subject in need thereof, the method comprising administering to the subject an effective amount of a composition comprising a compound having the formula (XV)

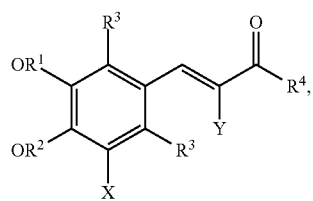

(XV)

or a solvate or a pharmaceutically acceptable salt thereof, wherein $R^1$ and $R^2$ are independently selected from the group consisting of hydrogen, $(C_1-C_3)$alkyl; halo$(C_1-C_3)$alkyl; $(C_3-C_7)$cycloalkyl; halo$(C_3-C_7)$cycloalkyl; phenyl$(C_1-C_3)$alkyl, aminophenyl$(C_1-C_3)$alkyl, and indanyl, wherein the phenyl or indanyl is optionally substituted with a halogen and the amino is optionally substituted with one or two $(C_1-C_3)$alkyl;

$R^3$, at each position it occurs, is independently selected from the group consisting of hydrogen; halogen; $(C_1-C_3)$ alkyl; halo$(C_1-C_3)$alkyl; $(C_1-C_3)$alkoxy; halo$(C_1-C_3)$alkoxy; OH, thiol, amino, and nitro;

$R^4$ is selected from the group consisting of $(C_1-C_3)$alkyl, OH, $NR^5R^6$, wherein each of $R^5$ and $R^6$ is independently selected from the group consisting of $(C_1-C_3)$alkyl; halo$(C_1-C_3)$alkyl, $(C_3-C_7)$cycloalkyl; halo$(C_3-C_7)$cycloalkyl; and phenyl$(C_1-C_3)$alkyl, wherein the phenyl is optionally substituted with halogen, $(C_1-C_3)$alkyl, or hydroxyl;

X is hydrogen or nitro; and

Y is H or CN.

In one embodiment of the method requiring the compound having formula (XV), $R^1$ and $R^2$ are hydrogen. Further, X can be a nitro group. Further, Y can be a cyano group. Further, $R^4$ can be $NR^5R^6$, $R^5$ being hydrogen. Further, $R^4$ can be an alkyl, a dialkylamine, or a hydroxyl.

In one embodiment, the compound is one of

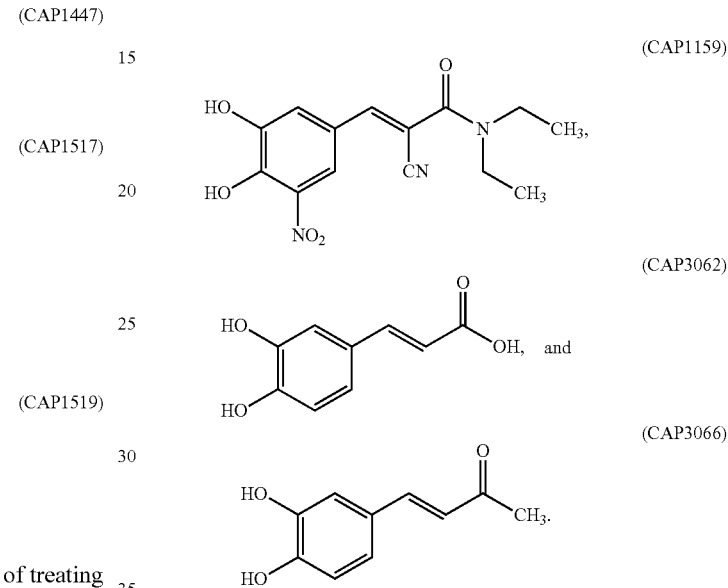

(CAP1159)

(CAP3062)

(CAP3066)

In another aspect, provided herein is a method of treating presbyopia or cataract in a subject in need thereof, the method comprising administering to the subject an effective amount of a composition comprising a compound having the formula (XVI)

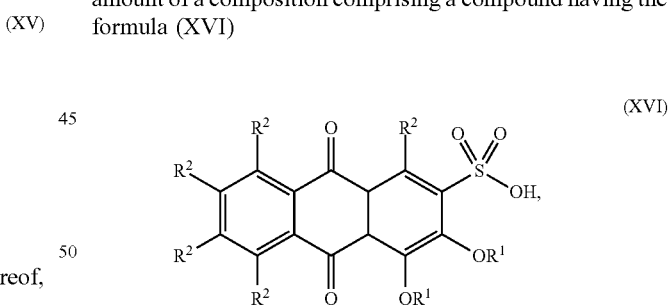

(XVI)

or a solvate or a pharmaceutically acceptable salt thereof, wherein $R^1$ is hydrogen or $OR^3$, wherein $R^3$ is selected from the group consisting of hydrogen, $(C_1-C_3)$alkyl; halo$(C_1-C_3)$ alkyl; $(C_3-C_7)$cycloalkyl; halo$(C_3-C_7)$cycloalkyl; phenyl $(C_1-C_3)$alkyl, aminophenyl$(C_1-C_3)$alkyl, and indanyl, wherein the phenyl or indanyl is optionally substituted with a halogen and the amino is optionally substituted with one or two $(C_1-C_3)$alkyl; and $R^2$, at each position it occurs, is independently selected from the group consisting of hydrogen; halogen; $(C_1-C_3)$ alkyl; halo$(C_1-C_3)$alkyl; $(C_1-C_3)$alkoxy; halo$(C_1-C_3)$alkoxy; OH, sulfonyl, thiol, amino, and nitro.

In one embodiment of the method requiring the compound having formula (XVI), $R^1$ is hydrogen. In one embodiment, $R^2$ is hydrogen. In one embodiment, the compound is one of

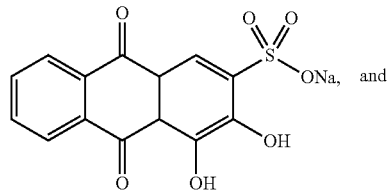
(CAP1072)

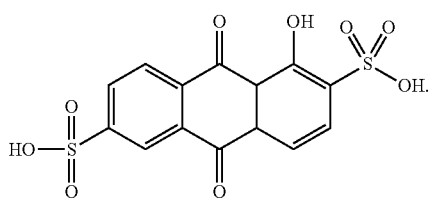
(CAP1219)

In another aspect, provided herein is a method of treating presbyopia or cataract in a subject in need thereof, the method comprising administering to the subject an effective amount of a composition comprising a compound selected from the group consisting of

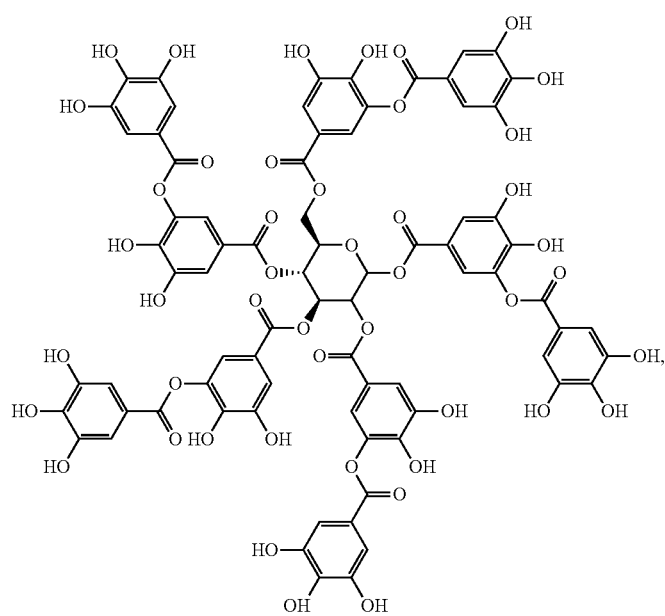
(CAP1176)

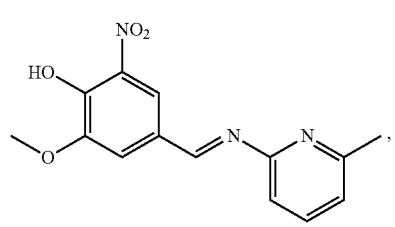
(CAP1110)

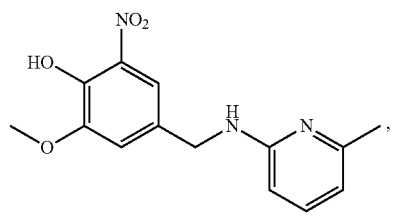
(CAP1112)

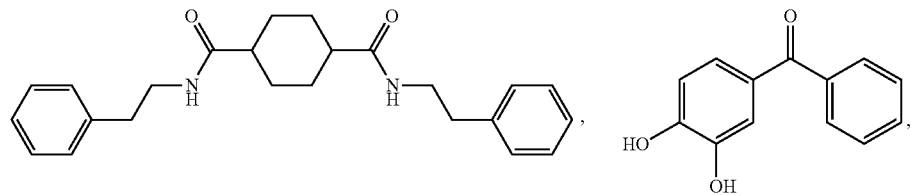
(CAP1280)

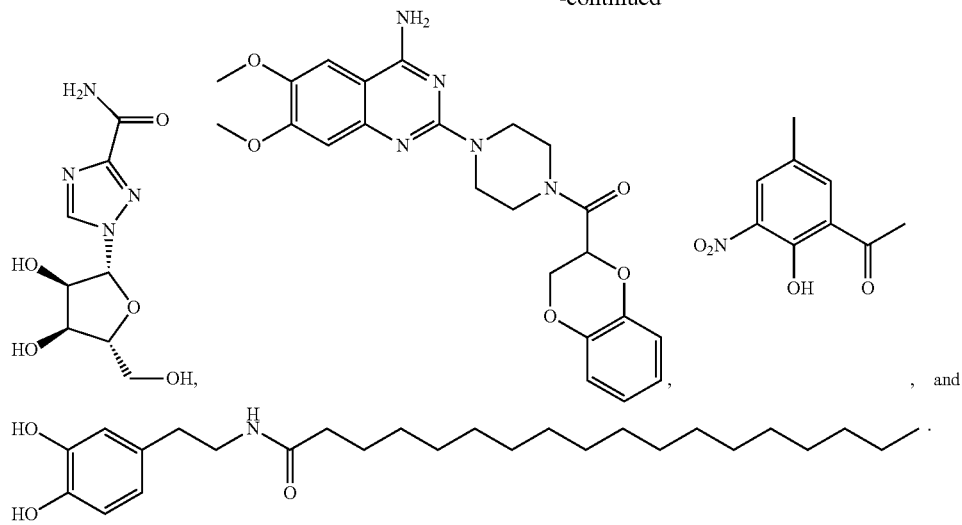

, and

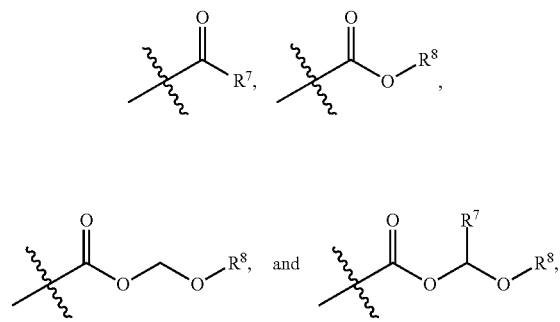

In another aspect, provided herein is a method of preventing and/or treating transthyretin (TTR)-associated amyloidosis in a subject in need thereof. The method comprises administering to the subject an effective amount of a composition comprising a compound having the formula

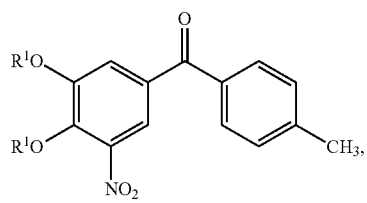

or a pharmaceutically acceptable salt thereof, wherein $R^1$ is selected from the group consisting of

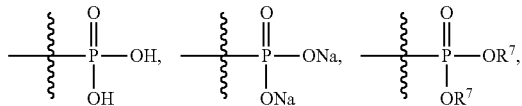

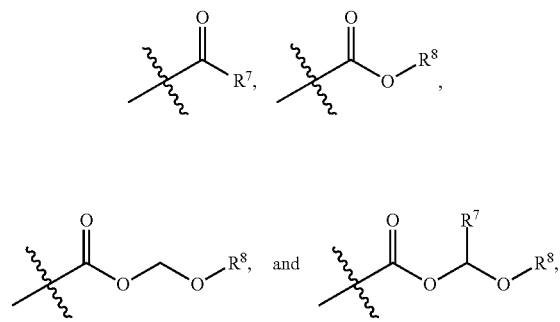

wherein $R^7$ is ($C_1$-$C_6$)alkyl and $R^8$ is ($C_1$-$C_6$)alkyl, aryl, or a polyethylene glycol group.

In one embodiment, the compound is

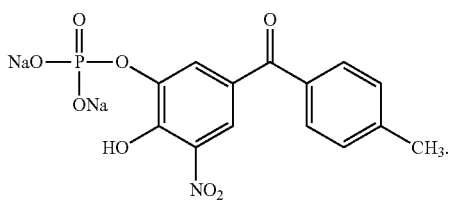

In another aspect, provided herein is a method of treating Parkinson's disease in a subject in need thereof. The method comprises administering to the subject an effective amount of a composition comprising a compound having the formula

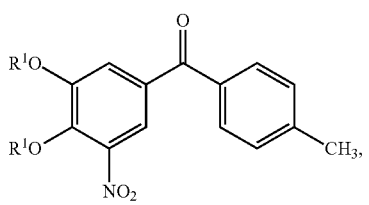

wherein $R^1$ is selected from the group consisting of

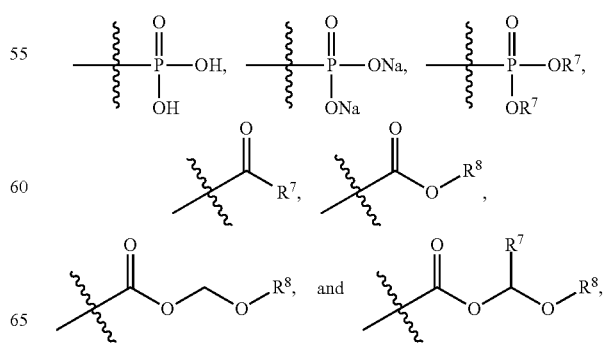

wherein $R^7$ is $(C_1-C_6)$alkyl and $R^8$ is $(C_1-C_6)$alkyl, aryl, or a polyethylene glycol group.

In one embodiment, the compound is

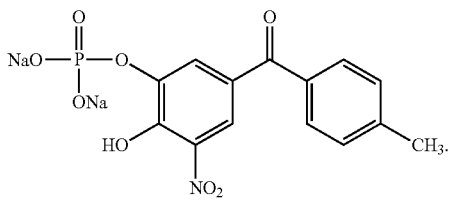

BRIEF DESCRIPTION OF THE DRAWINGS

FIGS. 1A and 1B depict graphs for stiffness of lens cortex and nucleus (1A), and loss in accommodative power (diopters) (1B) as a function of age. Graphs represent a summary of four separate studies on human accommodation. FIG. 1C depicts mass distribution in the water-soluble fraction in young (19 years) (solid line and filled circle) and aged (83 years) (broken line and open circle) human lenses using SEC-MALS (multiangle light scattering). FIG. 1D shows changes in the content of soluble AC (open circle) and high molecular weight protein (closed circle) in the lens nucleus as a function of age.

FIGS. 4A, 4C, and 4E show $EC_{50}$ curves for one compound, respectively, from the macrocyclic, covalent, and the catechol series. FIGS. 4B, 4D, and 4F show percent protection from aggregation at 200 µM of compounds, respectively, from the macrocyclic, covalent, and the catechol series. Measurements for assessing protection were performed in triplicate.

FIGS. 9A-9F show $EC_{50}$ curves of select compounds depicting the fold change in protection of hAAC against UVC and $Ca^{+2}$ induced aggregation.

FIGS. 10A-10C are graphs showing dose-dependent protection of human lens epithelial cells (HLE) from UV-irradiation induced cell death. SRA 01/04 HLE cells were pre-incubated for 3 hours with varying concentrations of compounds and exposed to UV light (9600 mJ/cm², 254 nm). Percent viability was assessed by Alamar blue compared to non-irradiated controls after 24 hours. Mean±SD and linear regression curve fit produced with Graphpad software, and calculated EC50s (µM) are provided.

FIGS. 11A-11D show the effect of CAP1159 on exposure of eye lens to UVC radiation.

FIG. 11A shows representative dark field digital images of porcine eye lens (from a set of n=12 lens experiment), when exposed to 2 hours of 480 mJ/cm² per minute of UVC radiation in presence or absence of varying concentrations of CAP1159. The top row of the figure corresponds to lenses that were not exposed to UVC but contained same percent of DMSO as those that were exposed to UVC. The lenses were monitored and imaged for three days following the exposure to UVC. No drug was added to the lenses post UVC exposure.

FIG. 11B shows results of scoring of lenses (n=12) for cataract on days 1, 2, and 3 after exposure to UVC radiation in the study shown in FIG. 11 A. The scale (0-9) for grading is shown in FIG. 11A.

FIG. 11C shows progression of cataract following UVC exposure over a period of three days.

FIG. 11D is a bar graph showing soluble protein content from treatment (CAP1159) and control groups as measured at 280 nm at the end of the three-day period. Lenses from each group were lysed and the supernatant pooled to measure the total soluble protein content from each group.

FIG. 12A shows representative dark field digital images of porcine eye lens (from a set of n=12 lens experiment), when exposed to 2 hours of 480 mJ/cm² per minute of UVC radiation in presence or absence of varying concentrations of CAP1160. The top row of the figure corresponds to lenses that were not exposed to UVC but contained same percent of DMSO as those that were exposed to UVC. The lenses were monitored and imaged for three days following the exposure to UVC. No drug was added to the lenses post UVC exposure.

FIG. 12B. shows results of scoring of lenses (n=12) for cataract on days 1, 2, and 3 after exposure to UVC radiation in the study shown in FIG. 12A. The scale (0-9) for grading is shown in FIG. 12A FIG. 12C progression of cataracts following post UVC exposure as monitored over a period of three days.

FIG. 12D is a bar graph showing soluble protein content from treatment (CAP1160) and control groups as measured at 280 nm at the end of the three-day period. Lenses from each group were lysed and the supernatant pooled to measure the total soluble protein content from each group.

DETAILED DESCRIPTION

Compounds and Definitions

Figures 1A, 1B, 1C, 1D:
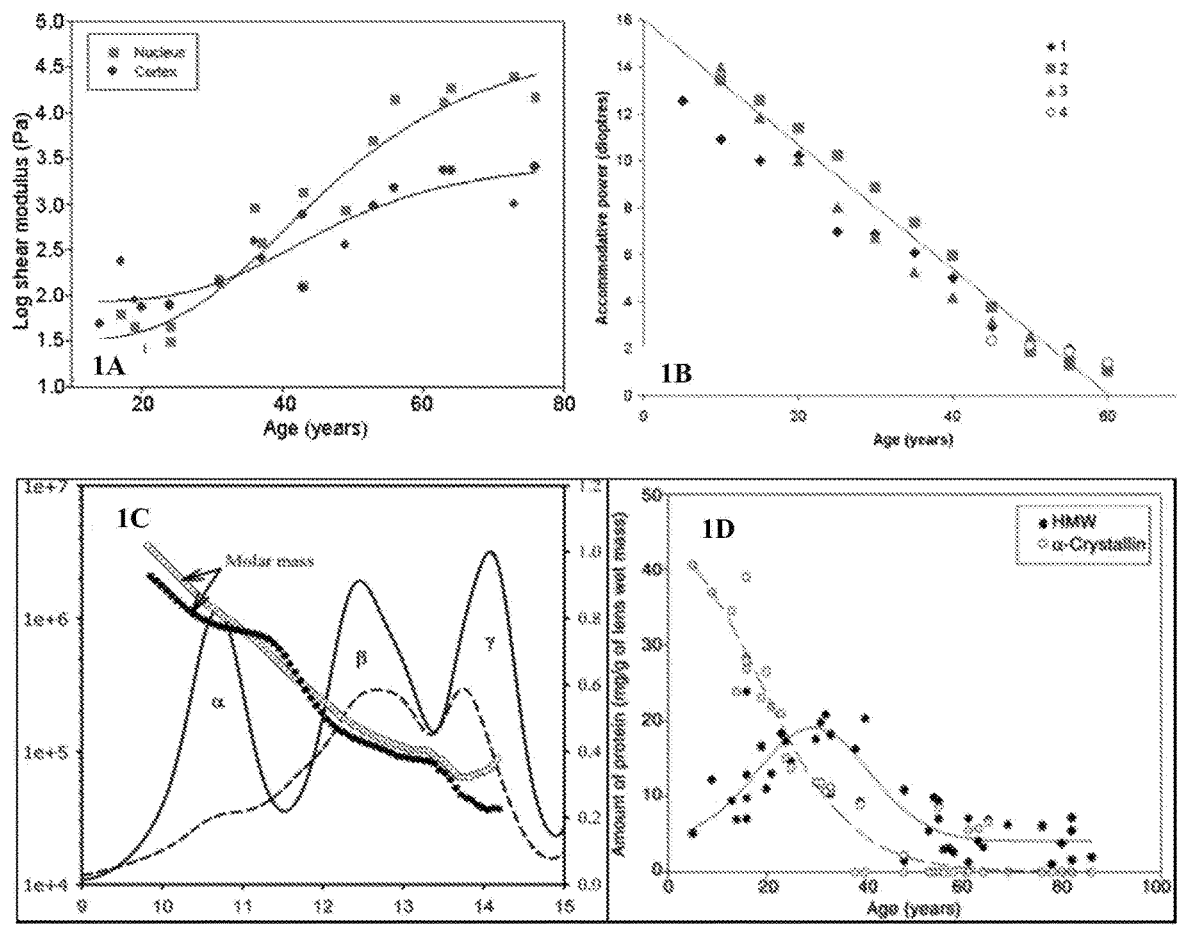
FIGS. 1A-1D show experimental results described in prior art.

The terms "halo" and "halogen" as used herein refer to an atom selected from fluorine (fluoro, —F), chlorine (chloro, —Cl), bromine (bromo, —Br), and iodine (iodo, —I).

The term "alkyl", used alone or as a part of a larger moiety such as e.g., "haloalkyl", means a saturated monovalent straight or branched hydrocarbon radical having, unless otherwise specified, 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like. "Monovalent" means attached to the rest of the molecule at one point.

The terms "cycloalkyl" used alone or as part of a larger moiety, refers to a saturated cyclic aliphatic monocyclic, bicyclic or tricyclic ring system, as described herein, having from, unless otherwise specified, 3 to 10 carbon ring atoms. Monocyclic cycloalkyl groups include, without limitation, cyclopropyl, cyclobutyl, cyclopentyl, cyclopentenyl, cyclohexyl, cyclohexenyl, cycloheptyl, cycloheptenyl, and cyclooctyl. Bicyclic cycloalkyl groups include e.g., cycloalkyl group fused to another cycloalkyl group, such as decalin or a cycloalkyl group fused to an aryl group (e.g., phenyl) or heteroaryl group, such as tetrahydronaphthalenyl, indanyl, 5,6,7,8-tetrahydroquinoline, and 5,6,7,8-tetrahydroisoquinoline. An example of a tricyclic ring system is adamantane. It will be understood that the point of attachment for bicyclic cycloalkyl groups can be either on the cycloalkyl portion or on the aryl group (e.g., phenyl) or heteroaryl group that results in a stable structure. It will be further understood that when specified, optional substituents on a cycloalkyl may be present on any substitutable position and, include, e.g., the position at which the cycloalkyl is attached.

The term "heterocyclyl" means a 4-, 5-, 6- and 7-membered saturated or partially unsaturated heterocyclic ring containing 1 to 4 heteroatoms independently selected from N, O, and S. The terms "heterocycle", "heterocyclyl", "heterocyclyl ring", "heterocyclic group", "heterocyclic moiety", and "heterocyclic radical", may be used interchangeably. A heterocyclyl ring can be attached to its pendant group at any heteroatom or carbon atom that results in a stable structure. Examples of such saturated or partially unsaturated heterocyclic radicals include, without limitation, tetrahydrofuranyl, tetrahydrothienyl, terahydropyranyl, pyrrolidinyl, pyrrolidonyl, piperidinyl, oxetanyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, and tetrahydropyrimidinyl. A heterocyclyl group may be mono- or bicyclic. Unless otherwise specified, bicyclic heterocyclyl groups include, e.g., unsaturated or saturated heterocyclic radicals fused to another unsaturated heterocyclic radical or aromatic or heteroaryl ring, such as for example, chromanyl, 2,3-dihydrobenzo[b][1,4]dioxinyl, tetrahydronaphthyridinyl, indolinonyl, dihydropyrrolotriazolyl, imidazopynmidinyl, quinolinonyl, dioxaspirodecanyl. It will be understood that the point of attachment for bicyclic heterocyclyl groups can be on the heterocyclyl group or aromatic ring that results in a stable structure. It will also be understood that when specified, optional substituents on a heterocyclyl group may be present on any substitutable position and, include, e.g., the position at which the heterocyclyl is attached.

The term "heteroaryl" used alone or as part of a larger moiety as in "heteroarylalkyl", "heteroarylalkoxy", or "heteroarylaminoalkyl", refers to a 5-10-membered aromatic radical containing 1-4 heteroatoms selected from N, O, and S and includes, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The term "heteroaryl" may be used interchangeably with the terms "heteroaryl ring", "heteroaryl group", or "heteroaromatic". The terms "heteroaryl" and "heteroar-", as used herein, also include groups in which a heteroaromatic ring is fused to one or more aryl rings, where the radical or point of attachment is on the heteroaromatic ring. Nonlimiting examples include indolyl, indazolyl, benzimidazolyl, benzthiazolyl, quinolyl, quinazolinyl, and quinoxalinyl. A heteroaryl group may be mono- or bicyclic. It will be understood that when specified, optional substituents on a heteroaryl group may be present on any substitutable position and, include, e.g., the position at which the heteroaryl is attached. As used herein, the term "aryl", used alone or in conjunction with other terms, refers to a 6-14 membered aromatic ring containing only ring carbon atoms. The aryl ring may be monocyclic, bicyclic or tricyclic. Non-limiting examples include phenyl, naphthyl or anthracenyl, and the like. It will also be understood that when specified, optional substituents on an aryl group may be present on any substitutable position. In an embodiment, the aryl group is unsubstituted or mono- or di-substituted.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

Pharmaceutically acceptable acidic/anionic salts include, e.g., the acetate, benzenesulfonate, benzoate, bicarbonate, bitartrate, carbonate, citrate, dihydrochloride, gluconate, glutamate, glycollylarsanilate, hexylresorcinate, hydrobromide, hydrochloride, malate, maleate, malonate, mesylate, nitrate, salicylate, stearate, succinate, sulfate, tartrate, and tosylate.

Route of Delivery

Methods used to deliver compounds described herein to the eye include topical, subconjunctival, intravitreal, and systemic.

Topical: Topical ocular drug administration is typically accomplished by eye drops. Contact time on the eye surface is short, but can be prolonged using specific formulations, e.g., gels, gelifying formulations, ointments, and inserts. Typically, the basic nature of the solution containing the drug composition is aqueous and as such, agents designed to increase the viscosity of the solution may be employed. Such agents include, for example, hydroxypropyl methylcellulose, carbopol, polyvinyl alcohol, and the like.

Subconjunctival administration: Traditionally subconjunctival injections have been used to deliver drugs at increased levels to the uvea. This mode of administration can be used to deliver drugs in controlled release formulations to the posterior segment and to guide the healing process after surgery.

Intravitreal administration: Direct drug administration into the vitreous offers the advantage of more straightforward access to the vitreous and retina. Delivery from the vitreous to the choroid is more complicated, however, due to the hindrance by the RPE (Retinal Pigment Epithelium) barrier. Small molecules are able to diffuse rapidly in the vitreous but the mobility of large molecules, particularly positively charged, is restricted. An injectable composition suitable for intraocular injection typically comprises a solution of the drug or a fine particle suspension, which may enable sustained delivery to the eye. Formulations are usually aqueous and may commonly include solubilization enhancers such as, but not limited to, polyvinyl alcohol, Tween 80, solutol, cremophore, and cyclodextrin. These solubilization enhancers may be used in combination. The formulation is typically in the pH range of 3-8, which is be regarded as acceptable for intravitreal formulations. To achieve an acceptable pH, buffering systems are sometimes used. These include but are not limited to citrate and phosphate based buffering systems. The tonicity of the intravitreal formulation may be adjusted to remain within a desirable range which typically would be 250-360 mOsm/kg. Adjustment of tonicity may be achieved for example by addition of sodium chloride. Typically, intravitreal formulations are produced by sterile manufacture for single use. Preserved formulations can be used, for example formulations containing a preservative such as benzoyl alcohol. The dose of the active agent in the compositions of the invention will depend on the nature and degree of the condition, the age and condition of the patient and other factors known to those skilled in the art. Administration can be either as a single injection with no further dosing or multiple injections.

Systemic: Systemic medication is required for posterior segment therapy and to complement topical therapy for the anterior segment. The posterior segment always requires systemic therapy, because most topical medications do not penetrate to the posterior segment. Retrobulbar and orbital tissues are treated systemically.

Prodrug Formulations and Permeability Enhancers

In some embodiments, the present technology provides a method of treating presbyopia or cataract, the method requiring administration of an effective amount of a composition comprising a compound described herein, the compound being present in a prodrug form, or being converted to a prodrug form. Prodrug formulations use pharmacologically inactive derivatives of drug molecules that are better able to penetrate the cornea (e.g., they are more lipophilic) than the standard formulation of the drug. See review by Brian G. Short, *Toxicologic Pathology*, 36:49-62, 2008. As described in the review and the references cited therein, within the cornea or after corneal penetration, the prodrug is either chemically or enzymatically metabolized to the active parent compound. Enzyme systems identified in ocular tissues include esterases, ketone reductase, and steroid 6β-hydroxylase.

Most prodrugs are delivered conventionally by topical application such as antiviral prodrugs ganciclovir and acyclovir, although ganciclovir has also been delivered intravitreally by injection or as a nonbiodegradable reservoir (see below). Delivery of a drug with a nonnatural enzyme system in the cornea has been achieved with topical 5-flurocytosine, a prodrug of 5-fluorouracil, administered after subconjunctival transplantation of cells containing the converting enzyme cytosine deaminase. Increased corneal penetration into the anterior segments can be achieved with the addition of permeability enhancers to the drug formulation. Surfactants, bile acids, chelating agents, and preservatives have all been used. Cyclodextrins, cylindrical oligonucleotides with a hydrophilic outer surface and a lipophilic inner surface that form complexes with lipophilic drugs, are among the more popular permeability enhancers. They increase chemical stability and bioavailability and decrease local irritation, and they have been used with corticosteroids, choloramphenicol, diclofenac, cyclosporine, and sulfonamide carbonic anhydrase inhibitors. The present invention includes small molecule disaggregases (SMDs) that are synthesized as prodrugs such that they have a better ability to permeate the cornea.

EXAMPLES

Example 1: Recombinant hAAC Forms HMW Aggregates Upon Exposure of UV and Heat

Figures 2A, 2B, 2C, 2D:
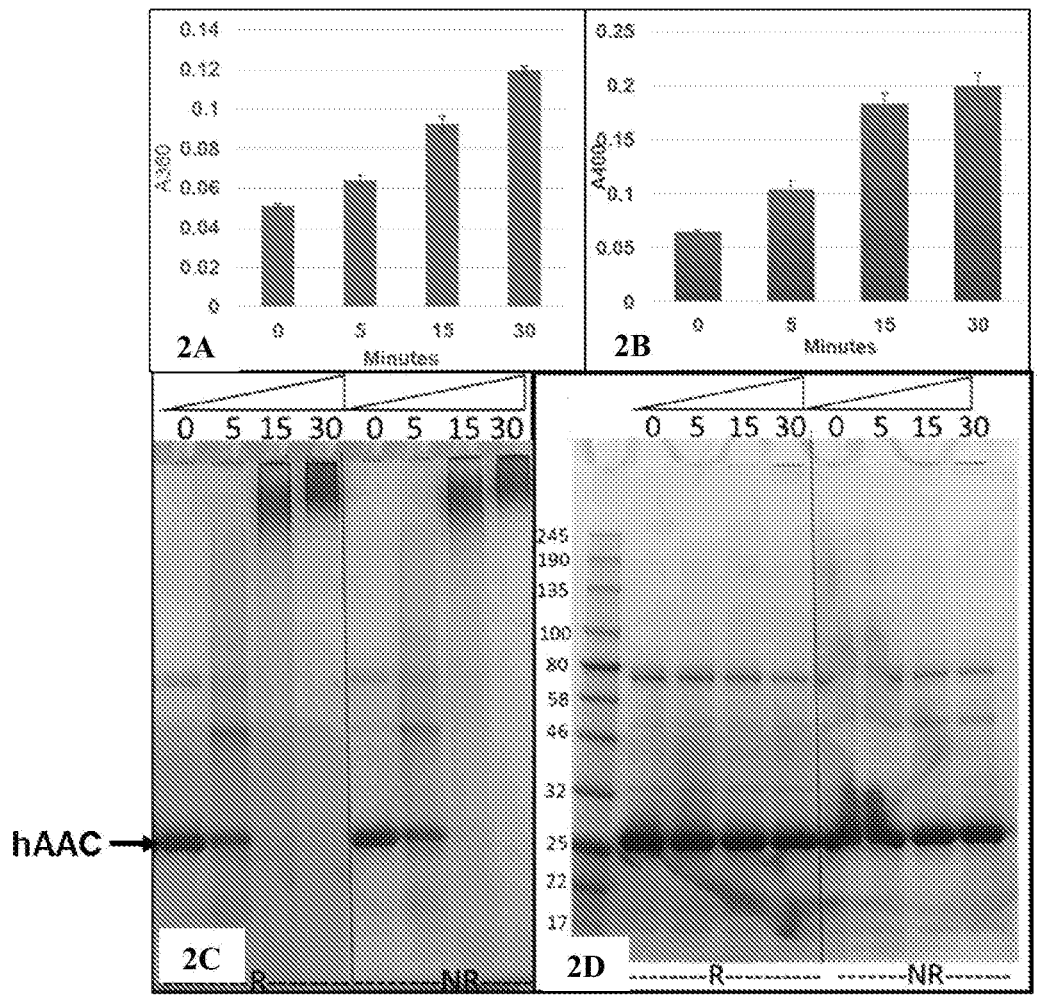
FIG. 2A shows the effect of exposing hAAC at 500 ug/ml to UVC.
FIG. 2B shows the effect of subjecting hAAC to $Ca^{+2}$/heat for 0, 5, 15 and 30 mins. Absorbance at 360/400 nm was measured at each time point. Mean±SEM of the measurements are shown.

The factors that contribute to the age-related loss of soluble functional AAC includes post translational modification of amino-acid residues due to exposure to UV and heat. Therefore, to identity potent SMDs, experimental conditions were developed under which hAAC, when exposed to UV-C radiation or heated to 50° C., formed HMW aggregates (FIGS. 2A-2D). Consistent with published reports, hAAC HMW aggregates formed under UV-C radiation remain insoluble compared to the heat induced HMW (FIGS. 2C & 2D). The system described herein recapitulates the factors that contribute to formation of presbyopia.

Example 2: Identification of Small Molecule Disaggregases (SMD) of hAAC

Figures 3A, 3B:
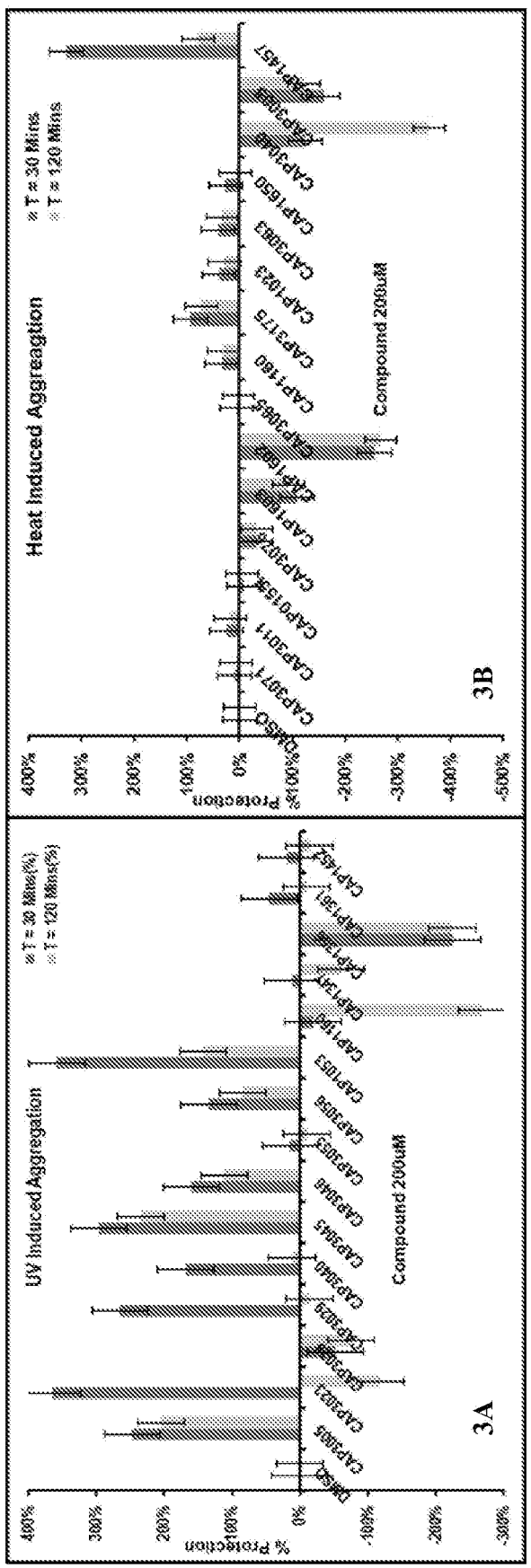
FIGS. 3A and 3B show representative data for extent to which hAAC is protected by compounds (or DMSO control) from becoming aggregated. Aggregation was monitored for 120 minutes by absorbance at 360 nm for UV induced aggregation (3A) or at 400 nm for heat induced aggregation (3B). Mean±SEM of the measurements are shown.

A large number of small molecule compounds were screened for their ability to protect hAAC from forming HMW aggregates. In the screen based on UV-induced aggregation, 310 compounds were tested, whereas in that based on $Ca^{2+}$/heat-induced aggregation, 206 compounds were tested. Each compound was used at 200 uM concentration. In view of the fact that nearly 40% of eye lens consists of AC, a high concentration of recombinant hAAC (500 ug/ml for UV and 400 μg/ml for heat) was used in the screens. The screening resulted in the identification of a number of compounds that showed efficacy in protecting hAAC from forming HWM aggregates (Table 1). These compounds are referred to as SMDs. A representative set of data is presented in FIGS. 3A-3B. Details of the procedure for the identification of SMDs is described in the following.

For identifying compounds that are effective in preventing the aggregation of human AAC in eye lens and can function as or developed into pharmacological agents for the treatment of presbyopia, it is important that the biochemical screening method (i) be based on non-enzymatic conditions that contribute to the loss of function of AAC and formation of HMW aggregates, and (ii) uses relevant species of AAC, particularly since human AAC contains a unique cysteine residue (Cys142). Accordingly, the screening method employed here has taken these factors into consideration.

Library design: Since the SMDs of the present disclosure are meant for ophthalmic application, factors that are key are those that play a role trans-cellular drug permeation. These factors are log P, pKa, and MW. Log P is the most important feature of the drug since it determines whether the SMD can cross the epithelium layer. A Log P of 2-3 provides optimal chemical composition for absorption across the corneal layer. The SMDs must also possess adequate aqueous solubility since it must diffuse across the water-filled stroma, and it is the initial drug concentration in the tear film that determines the driving force for corneal penetration. Accordingly, the library of compounds used for screening for SMDs was assembled such that the compounds included possessed physicochemical properties of drugs known to have high tissue penetration. See Table 1 below for details.

TABLE 1

Physicochemical property criteria for library design

| Property | Criteria |
|---|---|
| Mol. Wt. (Da) | ≤650 |
| cLogP | 1-4 |
| H-bond acceptor | ≤6 |
| H-bond donor | ≤5 |
| No. of rotatable bonds | ≤6 |
| Polar surface area (PSA) (Å$^2$) | ≤70 |
| Aqueous Solubility (ug/ml) | 500 |

To perform screening, each compound at 200 μM concentration (0.5% DMSO) was incubated with hAAC (500 ug/ml for UV and 400 ug/ml for heat induced aggregation) for 30 mins at room temperature and absorbance measured at multiple time points (0, 30, 60, 90 and 120 minutes). Compounds showing greater than 50% protection relative to untreated were retested and rank ordered to provide dose dependent EC$_{50}$ value measurements. Table 2 below shows distribution of compounds and the extent to which they protect hAAC from aggregating.

Structural analysis of the SMDs identified revealed that compounds that protect against aggregation of hAAC under UV exposure can be grouped into two classes, namely macrocyclics and "covalent", and those that protect against heat induced aggregation as catechols. The molecular structures of the hits for each series, along with their percent protection, are shown in FIGS. 4A-4F. Dose-dependent potency curve and EC$_{50}$ value for one compound from each series are also shown. The fact that the SMDs identified prevent the aggregation of hAAC when exposed to UV, demonstrate their ability to directly engage hAAC.

TABLE 2

Distribution of compounds showing the protection of aggregation of hAAC

| | No. of compounds | |
|---|---|---|
| % protection | UV | Heat (50° C.) |
| ≤0 | 225 | 170 |
| ≤20 | 32 | 20 |
| ≤40 | 9 | 9 |

TABLE 2-continued

Distribution of compounds showing the protection of aggregation of hAAC

| | No. of compounds | |
|---|---|---|
| % protection | UV | Heat (50° C.) |
| ≤60 | 5 | 2 |
| ≤80 | 7 | 2 |
| ≤100 | 4 | 1 |
| >100 | 28 | 2 |

Example 3: SMDs Forming Covalent Bond with ACC Prevent HMW hAAC Aggregate Formation AAC contains two cysteine residues which are known to undergo post translational modification to form intra/intermolecular disulfide bonds resulting in HMW aggregates. As such, it was hypothesized that the formation of disulfide bonds could be prevented using a structure-guided design employing covalent bond forming cysteine-reactive drug-like compounds targeting the two cysteines in order to develop potent and selective SMDs of hAAC. Accordingly, irreversible electrophile cysteine-reactive compounds comprising acrylamides and chloro-acetamides functional groups were included in screening assays for SMDs. These compounds were made using the synthesis route shown below in Scheme 1.

Scheme 1

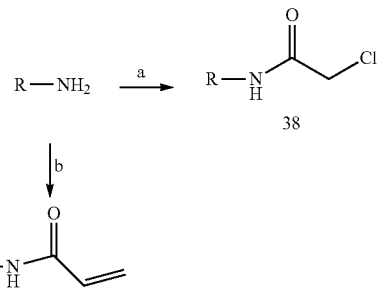

R = aliphatic or aromatic group
Reagents and conditions:
(a) chloroacetyl chloride, DIEA, CH$_2$Cl$_2$, r.t.;
(b) Acryloyl chloride, DIEA, CH$_2$Cl$_2$, r.t.

Figures 4A, 4B, 4C, 4D, 4E, 4F:
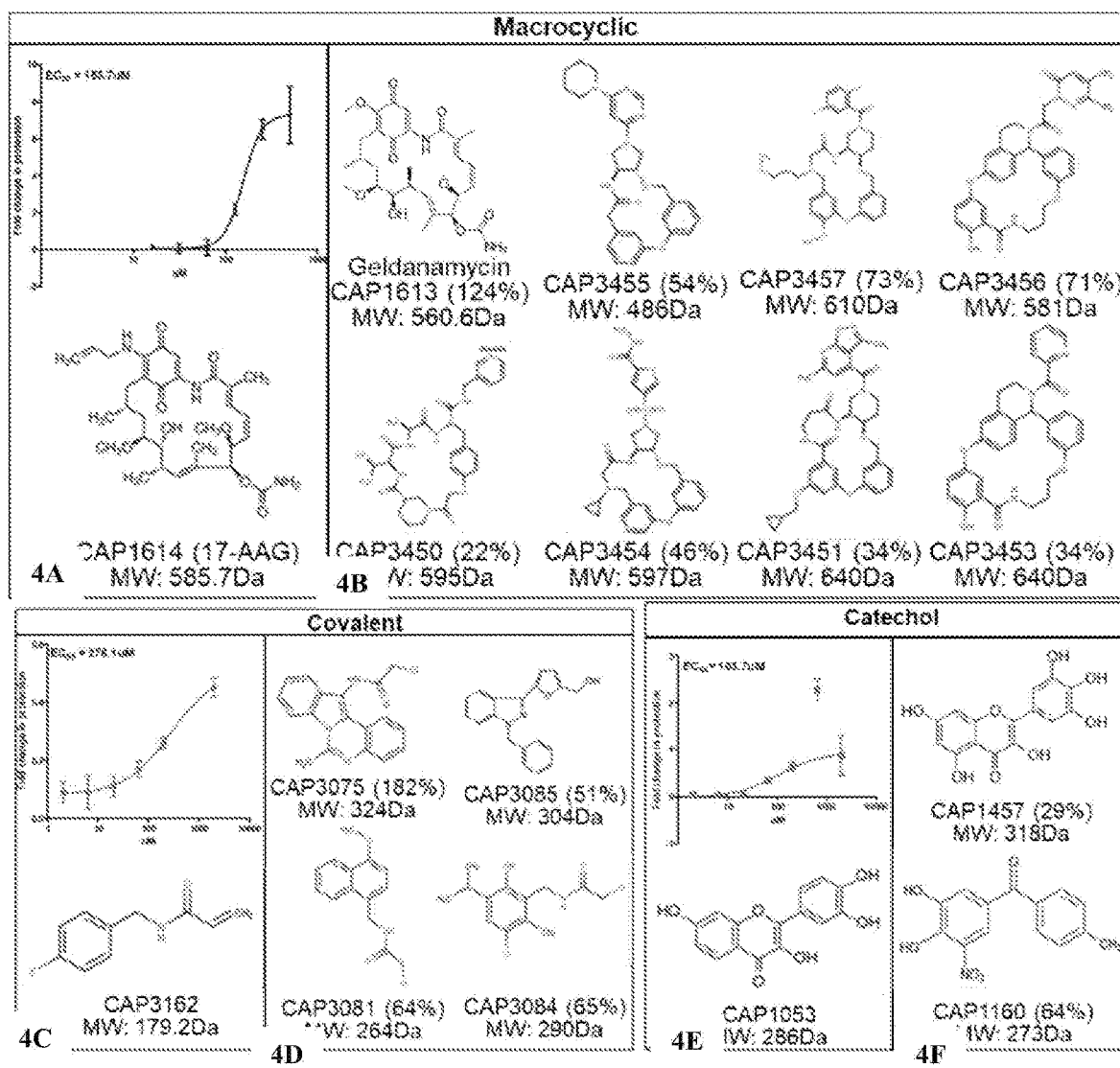
FIGS. 4A-4F show structure activity relationship (SAR) based classification of compounds discovered from UV and heat induced hAAC aggregation assays. Compounds are grouped into three series, Series-1: Macrocyclics; Series-2: "Covalent," and Series-3: Catechols.
Figure 5:
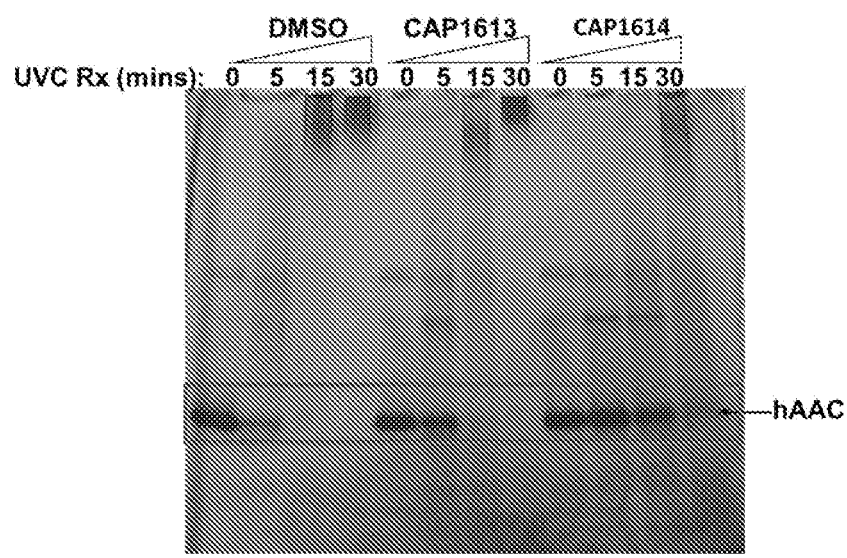
FIG. 5 shows results of a biochemical test for target (i.e., hACC) engagement by SMD. hACC (500 ug/ml) was treated overnight with 200 µM CAP1613 and CAP1614 and exposed to UV for 0, 5, 15 or 30. Samples from each time point were run on a SDS-PAGE under non-reducing condition. Insoluble and soluble HMW aggregates are shown by boxes at the top and bottom of the gel, respectively.
Figure 6A:
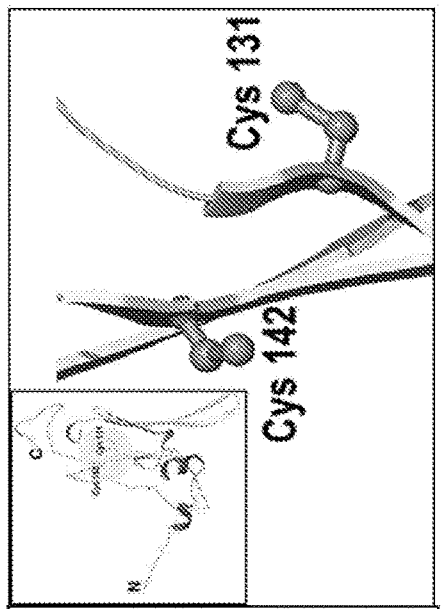
FIG. 6A shows sequence alignment of mammalian AACs. The conserved Cys (Cys131) is highlighted. Cys (Cys142), present only inhuman and chimpanzee, is also highlighted. A 3D model structure of hAAC (inset), showing the location of the residues Cys131 and Cys142, is shown to the right.
Figure 6B:
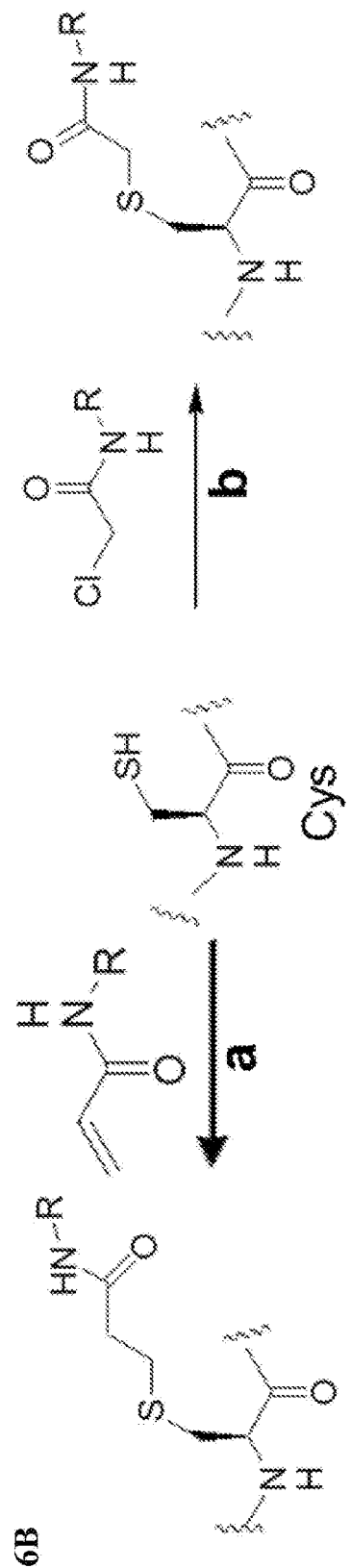
FIG. 6B shows reaction scheme for modification of cysteine with cysteine-reactive acrylamides (a) and chloro-acetamides (b).

The screening resulted in the identification of multiple compounds (FIGS. 4C-4D). These compounds are referred to as "covalent" given their potential to from covalent bond with the cysteine residue (FIGS. 6A and 6B).

Example 4: Cell Based Assays Using Human Lens Epithelial (HLE) Cells

Figure 7A:
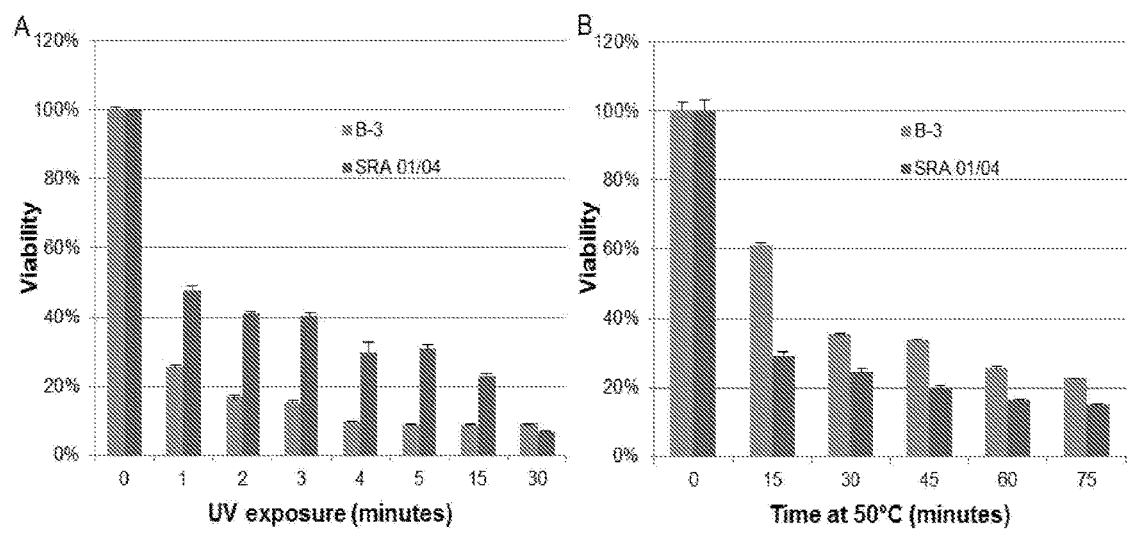
FIG. 7A shows results for viability of HLE cells (B3 and SRA 01/04) exposed to UV (left) or heat (right), assessed 24 hours post-exposure by. Alamar blue was used for assessing viability. Mean±SEM of the measurements are shown.
Figure 7B:
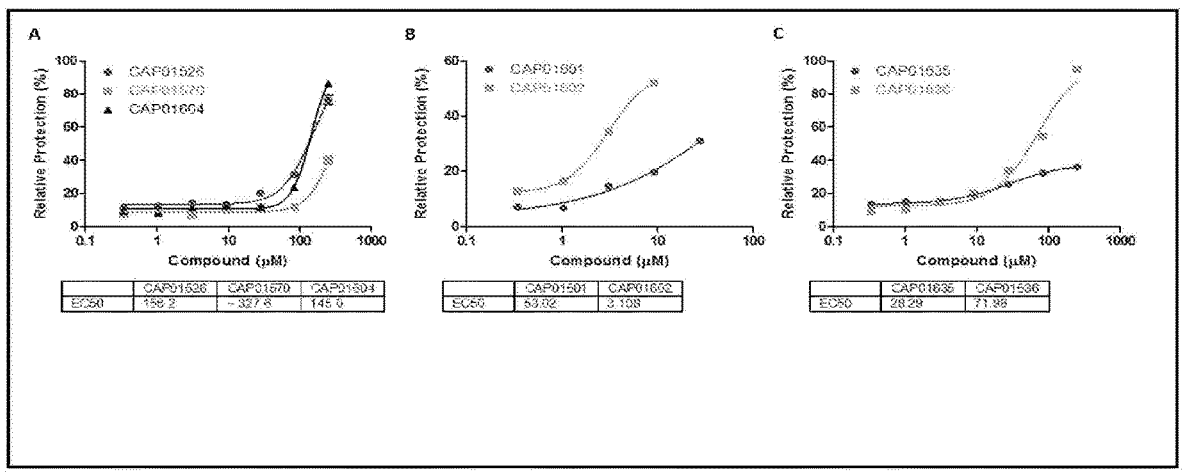
FIG. 7B shows protection of SRA 01/04 cells (human lens epithelial cell line), pre-incubated with varying concentrations of compounds two hours prior to UV exposure. Relative protection was measured as percent viability compared to vehicle control 24 hours following UV exposure. Effect of compounds from each of three distinct chemical series (macrocyclics, covalent, and catechol) are shown. Mean±SEM of the measurements are shown.

Cell-based using assays using human lens epithelial cell lines SRA 01/04 and B3 were also performed. The cells were exposed to UV or heat and cell viability assessed 24 hours post-exposure by Alamar blue staining. The results are shown in FIGS. 7A and 7B. In another experiment, SRA 01/04 cells were pre-incubated with varying concentrations of compounds two hours prior to UV exposure. Relative protection was measured as percent viability compared to vehicle control 24 hours following UV exposure. Effect of compounds from each of three distinct chemical series (macrocyclics, covalent, and catechol) are shown in FIG. 7B. Mean±SEM of the measurements are shown.

Figures 8A, 8B:
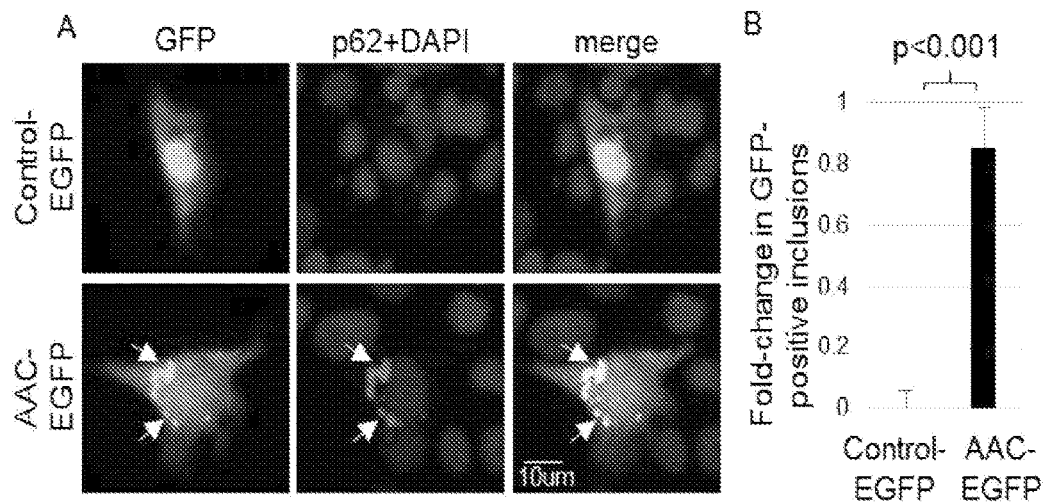
FIG. 8A shows ectopic expression of AAC-EGFP in B-3 cells forms inclusions that co-localize with p62 (arrows).
FIG. 8B shows results of automated image analysis of >2500 cells. A statistically significant increase in GFP-positive inclusions due to AAC overexpression was observed. Mean±SEM of the measurements and p value (t test) are shown.
Figures 9A, 9B, 9C, 9D:
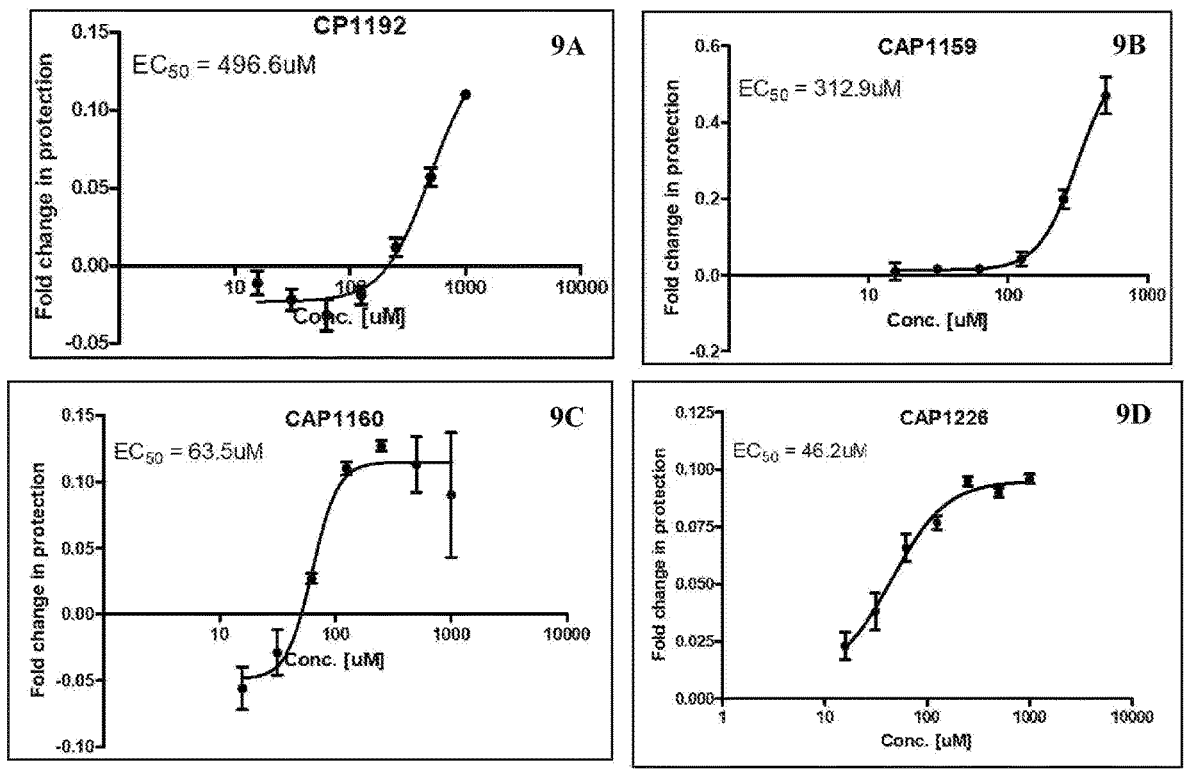
Figure 10C:
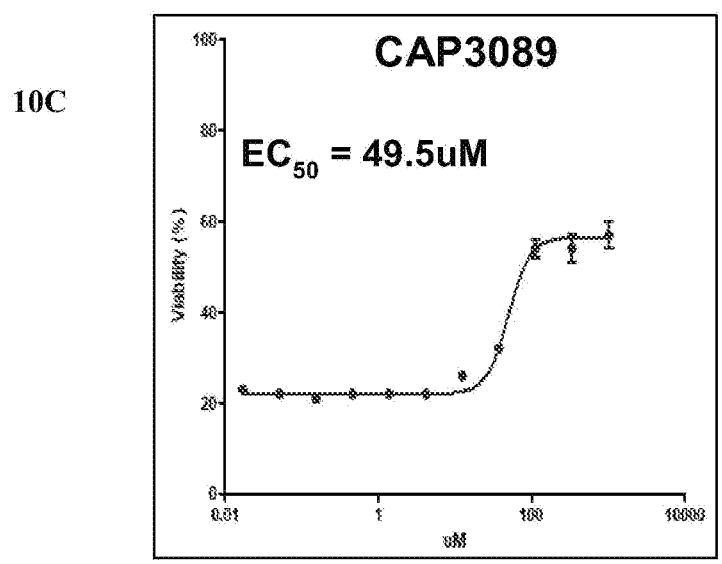
Figures 12A, 12B, 12C, 12D:
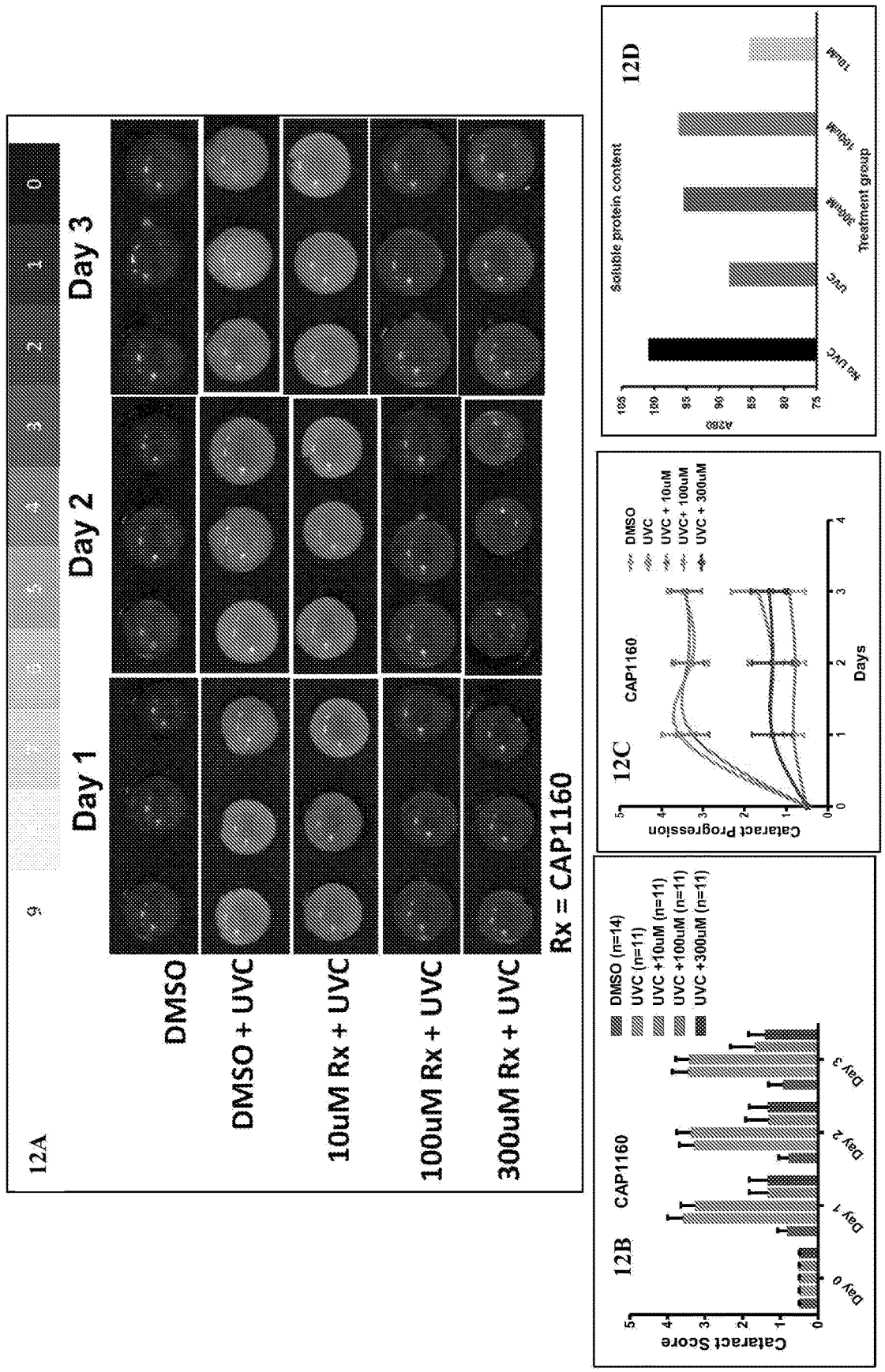
FIGS. 12A-12D show the effect of CAP1160 on exposure of eye lens to UVC radiation.

Ectopic expression of AAC-EGFP in B-3 cells shows that AAC forms inclusions that co-localize with p62 (arrows) (FIG. 8A). Automated image analysis of >2500 cells is shown in FIG. 8B. A statistically significant increase in GFP-positive inclusions due to AAC overexpression was observed. Mean±SEM of the measurements and p value (t test) are shown. The results show that high-content screening could be used to evaluate the cellular pharmacodynamic effects of SMDs for measuring cellular aggregates of AAC.

Example 5. Synthesis of Catechol Derivatives

Catechol derivatives described herein can be synthesized using the reaction schemes shown below. Specific examples of the derivatives synthesized are described following the reaction schemes.

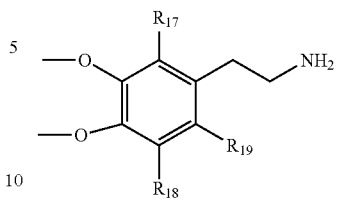

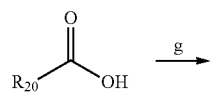

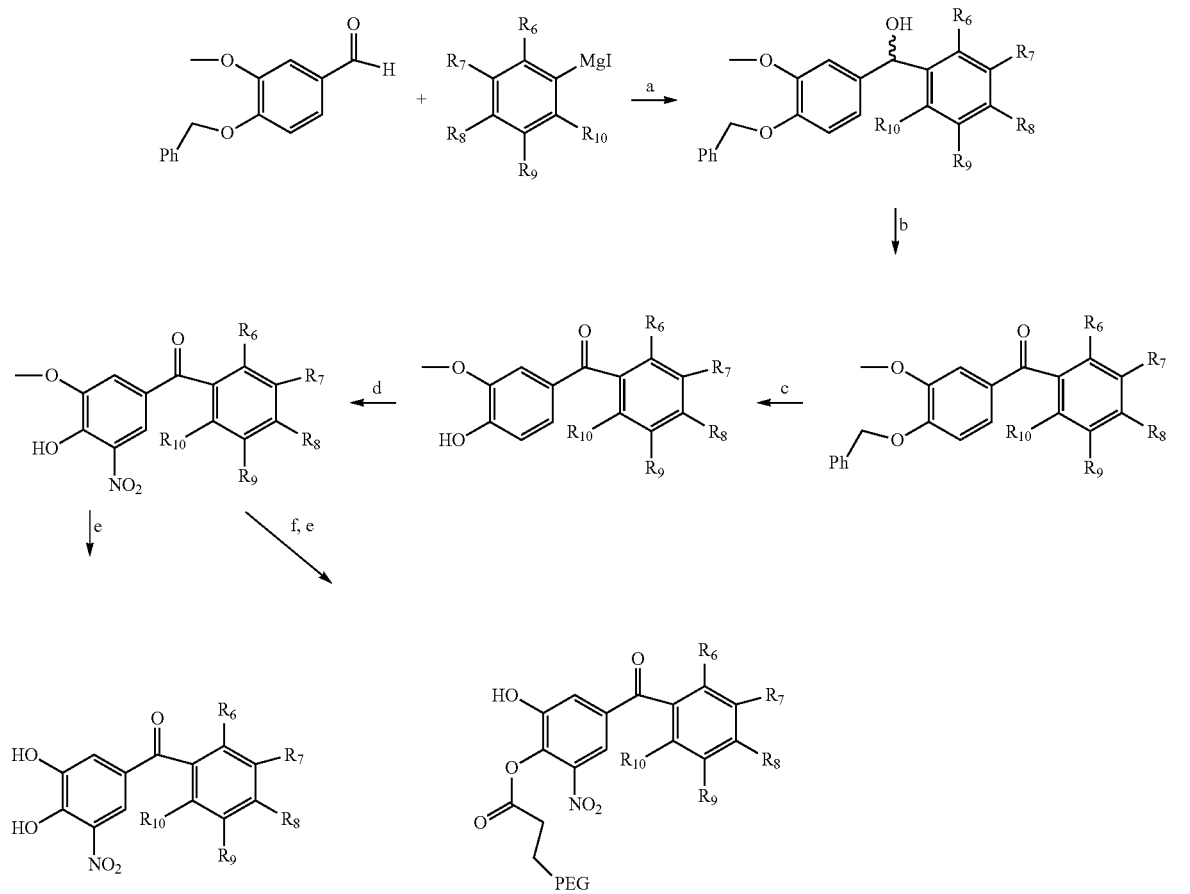

Reagents and conditions for scheme 1: (a) Grignard Reaction conditions, Diethylether, 0° C. to r.t.; (b) oxidation, PCC, $CH_2Cl_2$, r.t., (c) Pd/C, $H_2$, methanol, r.t.; (d) 70% $HNO_3$, r.t.; (e) $BBr_3$, $CH_2Cl_2$, r.t.; (f) PEG-acid, EDC, DMAP, r.t. In this reaction scheme, many different substituents can be used as the different R groups. $R_6$, $R_7$, $R_8$, $R_9$, and $R_{10}$ can independently be, for example, H, alkyl, aryl, halogen, nitro, amino, trifluoromethyl, and trifluoromethoxy.

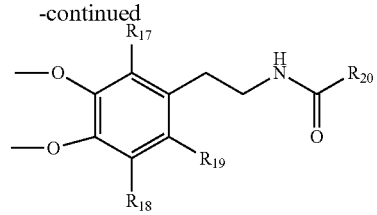

Reagents and conditions for scheme 2: (g), EDC, HOBt, DIEA, DMF, rt, 16 h. In this reaction scheme, many different substituents can be used as the different R groups. $R_{17}$, $R_{18}$, and $R_{19}$ can independently be, for example, H, alkyl, aryl, halogen, nitro, amino, methoxy, trifluoromethyl and trifluoromethoxy. $R_{20}$ can be an alkyl or an aryl group.

SCHEME 3

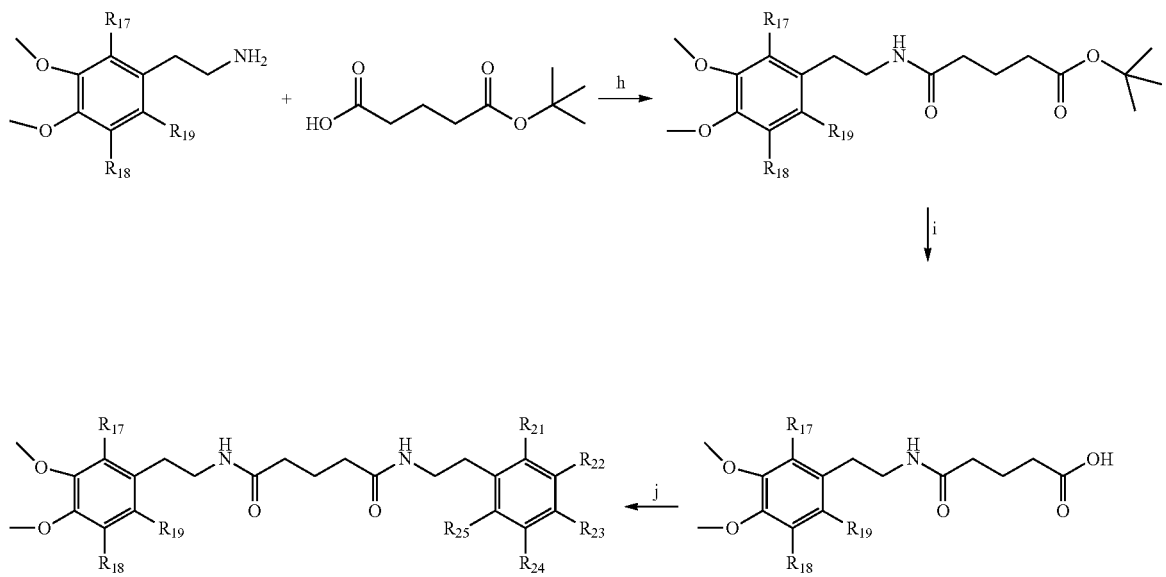

Reagents and conditions for scheme 3: (h) EDC, HOBt, DIEA, DMF, rt, 16 h; (i) TFA, $CH_2Cl_2$, rt, 6 h; (j), Aryl amines, EDC, HOBt, DIEA, DMF, rt, 20 h. In this reaction scheme, many different substituents can be used as the different R groups. $R_{17}$, $R_{18}$, $R_{19}$, $R_{21}$, $R_{22}$, $R_{23}$, $R_{24}$, and $R_{25}$ can, for example, independently be hydrogen, methyl, ethyl, n-propyl, isopropyl, n-butyl, and trifluoromethyl.

SCHEME 4

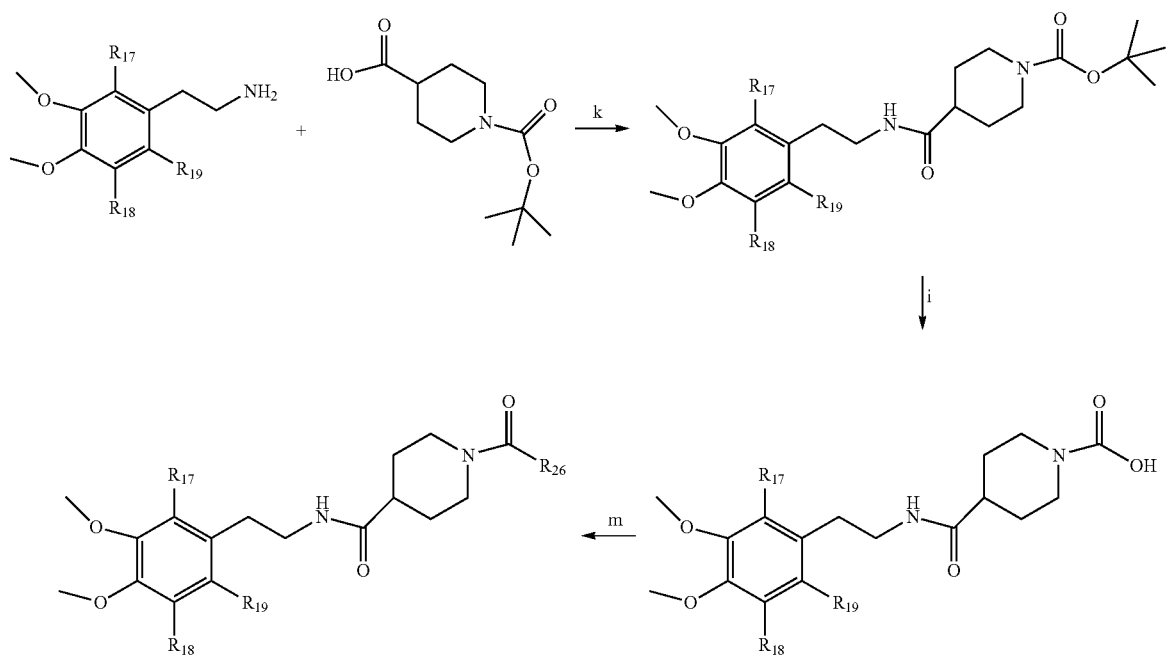

Scheme 4: Reagents and conditions for scheme 4: (k) EDC, HOBt, DIEA, DMF, rt, 15 h; (l) TFA, CH$_2$Cl$_2$, rt, 6 h; (m) R$_{26}$—CO$_2$H, EDC, HOBt, DIEA, DMF, rt, 22 h. In this reaction scheme, many different substituents can be used as the different R groups. R$_{17}$, R$_{18}$, and R$_{19}$ can, for example, independently be hydrogen, methyl, ethyl, n-propyl, isopropyl, n-butyl, and trifluoromethyl. R$_{26}$ can be an alkyl or an aryl group.

Synthesis of N-[2-(3,4-dimethoxyphenyl)ethyl]cyclobutanecarboxamide (CAP1226)

CAP1226 was synthesized using the appropriate reagents and starting materials as shown in Scheme 2 above. Briefly, a mixture of 3,4-dimethoxyphenethylamine (1 mmol), cyclobutanecarboxylic acid (1 mmol), EDC (1.2 mmol), HOBt (1.2 mmol), and DIEA (1.5 mmol) in DMF (3 mL) were stirred for 16 h at room temperature. The reaction mixture was partitioned between ethyl acetate and water. The organic layer was washed with saturated sodium bicarbonate solution, water, and brine respectively. The organic layer was dried over magnesium sulfate and concentrated in vacuo. The residue was chromatographed over silica gel using ethyl acetate hexane solvent system to afford the pure product CAP1226 as a solid (82%). The compound was characterized by NMR and Mass spectroscopy. $^1$H NMR (500 MHz, DMSO-d$_6$) δ 1.92-2.05 (m, 4H), 2.44-2.46 (m, 2H), 2.91-3.15 (m, 3H), 6.68 (dd, J=8 and 2 Hz, 1H), 6.73 (d, J=1.7 Hz, 1H), 6.82 (d, J=7.8 Hz, 1H), 7.56 (t, J=5.4 Hz, 1H, NH); ESI-MS m/z 264 (M+H)$^+$. Other compounds were selected using schemes 2, 3, or 4.

N,N-bis[2-(3,4-dimethoxyphenyl)ethyl]hexanediamine (CAP1225)

CAP1225 was prepared using scheme 2 shown above. The compound was characterized by NMR and Mass spectroscopy.

$^1$H NMR (500 MHz, DMSO-d$_6$) δ 1.45-1.48 (m, 4H), 1.98-2.01 (m, 4H), 2.56-2.57 (m, 4H), 3.01-3.09 (m, 4H), 3.76 (s, 6H), 3.79 (s, 6H), 6.67 (d, J=7.2 Hz, 1H), 6.69 (d, J=7.2 Hz, 2H), 6.75 (d, J=7.5 Hz, 2H), 6.79 (d, J=1.2 Hz, 2H), 6.81 (d, J=1.2 Hz, 2H), 7.72 (t, J=5.4 Hz, 2H, NH); ESI-MS m/z 474 (M+H)$^+$.

N-[2-(3,4-dimethoxyphenyl)ethyl]-1(phenylacetyl)-4-piperidinecarboxamide (CAP1227)

CAP1227 was prepared using scheme 2 shown above. The compound was characterized by NMR and Mass spectroscopy.

$^1$H NMR (500 MHz, DMSO-d$_6$) δ 1.41-1.52 (m, 4H), 2.32-2.38 (m, 1H), 2.61-2.68 (m, 3H), 2.88-2.92 (m, 1H), 3.21-3.29 (m, 2H), 3.62 (s, 2H), 3.72 (s, 3H), 3.75 (s, 3H), 3.92-3.95 (m, 1H), 4.41-4.45 (m, 1H), 6.61 (dd, J=7.8 and 1.7 Hz, 1H), 6.72 (d, J=1.7 Hz, 1H), 6.81 (d, J=8 Hz, 1H), 7.19-7.25 (m, 3H), 7.28-7.32 (m, 2H), 7.68 (t, J=5.2 Hz, 1H, NH); ESI-MS m/z 412 (M+H)$^+$.

N,N'-bis[2-(3,4-dimethoxyphenyl)ethyl]pentanediamide (CAP1228)

CAP1228 was prepared using scheme 3 shown above. The compound was characterized by NMR and Mass spectroscopy.

$^1$H NMR (500 MHz, DMSO-d$_6$) δ 1.61-162 (m, 2H), 1.98-2.10 (m, 4H), 2.65-2.70 (m, 4H), 3.30-3.39 (m, 4H), 3.78 (s, 6H), 3.79 (s, 6H), 6.67 (dd, J=8 and 1.6 Hz, 2H), 6.77 (d, J=1.6 Hz, 2H), 6.82 (d, J=8 Hz, 2H), 7.71 (t, J=5.4 Hz, 2H, NH); ESI-MS m/z 460 (M+H)$^+$.

N-[2-(3,4-dimethoxyphenyl)ethyl]cyclopropanecarboxamide (CAP1230)

CAP1230 was prepared using scheme 2 shown above. The compound was characterized by NMR and Mass spectroscopy.

$^1$H NMR (500 MHz, DMSO-d$_6$) δ 0.58-0.67 (m, 4H), 1.46-1.53 (m, 1H), 2.62-2.68 (m, 2H), 3.21-3.27 (m, 2H), 3.76 (s, 3H), 3.77 (s, 3H), 6.67 (d, J=8 and 1.6 Hz, 1H), 6.75 (d, J=1.6 Hz, 1H), 6.81 (d, J=8 Hz, 1H), 7.98 (t, J=5.6 Hz. 1H, NH); ESI-MS m/z 250 (M+H)$^+$.

N-[2-(3,4-dimethoxyphenyl)ethyl]cyclopentanecarboxamide (CAP1231)

CAP1231 was prepared using scheme 2 shown above. The compound was characterized by NMR and Mass spectroscopy.

$^1$H NMR (500 MHz, DMSO-d$_6$) δ 1.48-1.78 (m, 5H), 2.58-2.61 (m, 4H), 3.27-3.35 (m, 4H), 3.75 (s, 3H), 3.76 (s, 3H), 6.72 (dd, J=7.8 and 1.6 Hz, 1H), 6.79 (d, J=1.6 Hz, 1H), 6.84 (d, J=8 Hz, 1H), 7.77 (t, J=5.4 Hz, 1H, NH); ESI-MS m/z 278 (M+H)$^+$.

N-[2-(3,4-dimethoxyphenyl)ethyl]-1-(4-fluorophenyl)-4-piperidinecarboxamide (CAP1232)

CAP1232 was prepared using scheme 2 shown above. The compound was characterized by NMR and Mass spectroscopy.

$^1$H NMR (500 MHz, DMSO-d$_6$) δ 1.47-1.71 (m, 4H), 2.37-2.41 (m, 1H), 2.62-2.71 (m, 3H), 2.80-2.88 (m, 2H), 3.23-3.32 (m, 3H), 3.75 (s, 3H), 3.76 (s, 3H), 6.65 (dd, J=8 and 1.6 Hz, 1H), 6.72 (d, J=1.6 Hz, 1H), 6.78 (d, J=7.8 Hz, 1H), 7.16-7.22 (2H), 7.41-7.46 (m, 2H), 7.72 (t, J=5.2 Hz, 1H, NH); ESI-MS m/z 415 (M+H)$^+$.

Example 6. Effectiveness of Select Catechol Derivatives in Preventing Ca$^{+2}$ and UVC Induced Aggregation of Alpha-A Crystalline Table 3 below lists select catechol derivatives and their effectiveness in preventing Ca$^{+2}$ and UVC induced aggregation of alpha-A crystalline.

TABLE 3
| Compound ID | Molecular Structure | Percent protection (at 200 μM) |
| --- | --- | --- |
| CAP1176 | 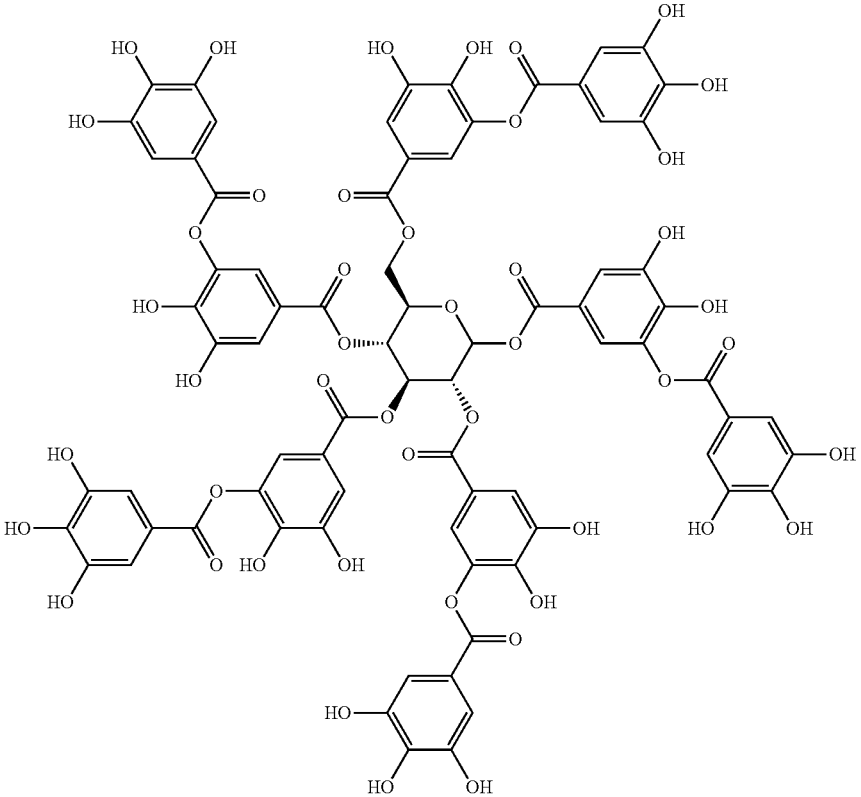 [SMILES: O=C(OC[C@H]1OC(OC(=O)c2cc(O)c(O)c(OC(=O)c3cc(O)c(O)c(O)c3)c2)[C@H](OC(=O)c2cc(O)c(O)c(OC(=O)c3cc(O)c(O)c(O)c3)c2)[C@@H](OC(=O)c2cc(O)c(O)c(OC(=O)c3cc(O)c(O)c(O)c3)c2)[C@@H]1OC(=O)c1cc(O)c(O)c(OC(=O)c2cc(O)c(O)c(O)c2)c1)c1cc(O)c(O)c(OC(=O)c2cc(O)c(O)c(O)c2)c1] | 76 |
| CP1192 | 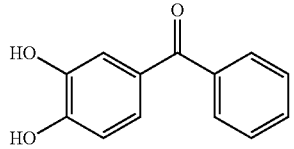 [SMILES: O=C(c1ccccc1)c1ccc(O)c(O)c1] | |
| CP1194 | 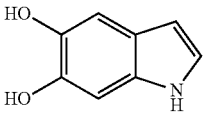 [SMILES: Oc1cc2cc[nH]c2cc1O] | 25 |
| CAP1042 | 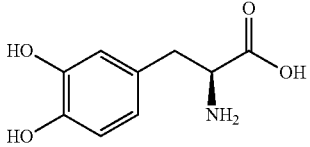 [SMILES: N[C@@H](Cc1ccc(O)c(O)c1)C(=O)O] | 6 |
| CAP1043 | 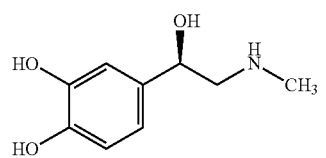 | −5 |

TABLE 3-continued

| Compound ID | Molecular Structure | Percent protection (at 200 μM) |
|---|---|---|
| CAP1044 | 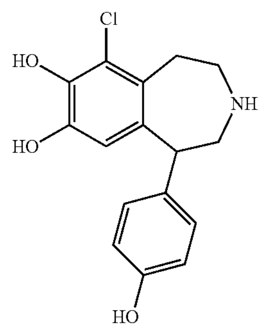 [SMILES: Oc1ccc(C2CNCCc3c2cc(O)c(O)c3Cl)cc1] | −16 |
| CAP1045 | 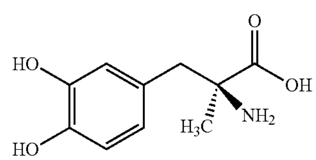 | |
| CAP1046 | 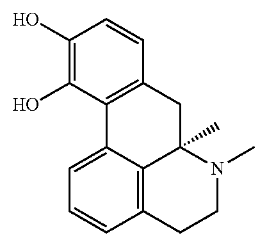 [SMILES: CN1CCc2cccc3c2[C@@]1(C)Cc1ccc(O)c(O)c1-3] | |
| CAP1047 | 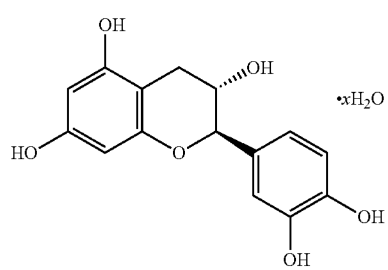 [SMILES: Oc1cc(O)c2c(c1)O[C@H](c1ccc(O)c(O)c1)[C@@H](O)C2 ; "·xH2O"] | −17 |
| CAP1048 | 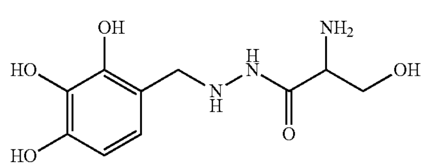 [SMILES: NC(CO)C(=O)NNCc1ccc(O)c(O)c1O] | |
| CAP1049 | 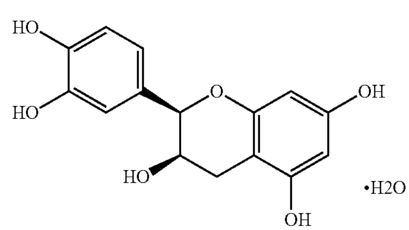 | −5 |

TABLE 3-continued

| Compound ID | Molecular Structure | Percent protection (at 200 μM) |
|---|---|---|
| CAP1050 | 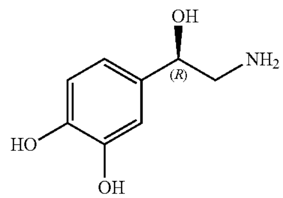 | |
| CAP1051 | 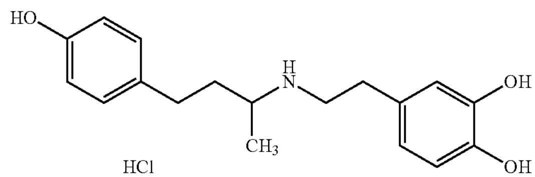 [SMILES: CC(CCc1ccc(O)cc1)NCCc1ccc(O)c(O)c1 ; Cl] | −28 |
| CAP1052 | 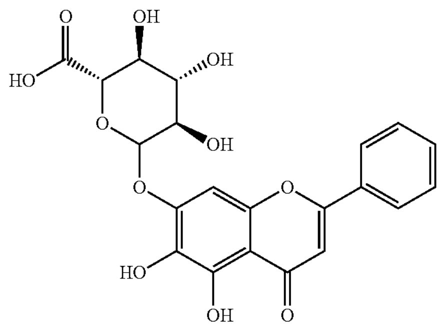 [SMILES: O=C(O)[C@H]1OC(Oc2cc3oc(-c4ccccc4)cc(=O)c3c(O)c2O)[C@H](O)[C@@H](O)[C@@H]1O] | 3 |
| CAP1053 | 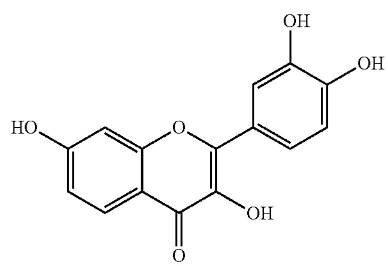 [SMILES: O=c1c(O)c(-c2ccc(O)c(O)c2)oc2cc(O)ccc12] | 52 |
| CAP1054 | 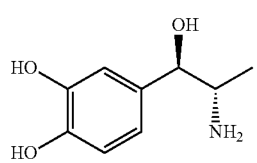 | |
| CAP1055 | 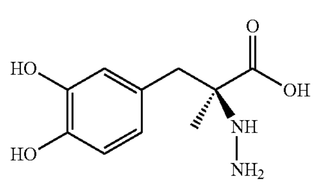 | 1 |
| CAP1056 | 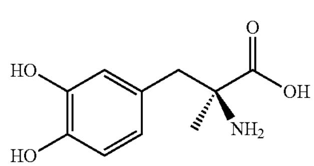 | −5 |

TABLE 3-continued

| Compound ID | Molecular Structure | Percent protection (at 200 μM) |
|---|---|---|
| CAP1057 | 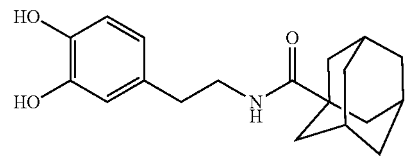 [SMILES: O=C(NCCc1ccc(O)c(O)c1)C12CC3CC(CC(C3)C1)C2] | −8 |
| CAP1058 | 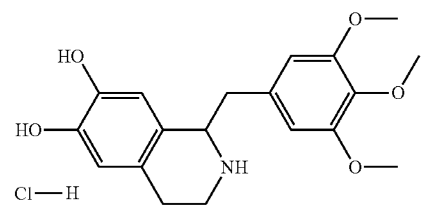 | −27 |
| CAP1072 | 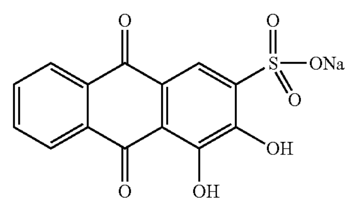 | 53 |
| CAP1110 | 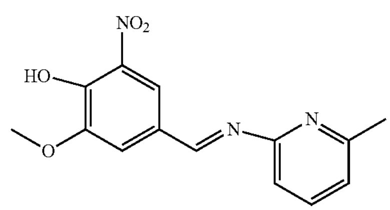 | 19 |
| CAP1112 | 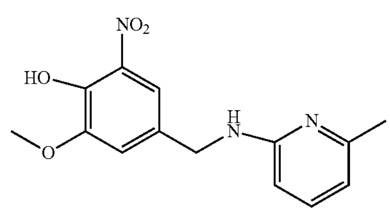 | 12 |
| CAP1113 | 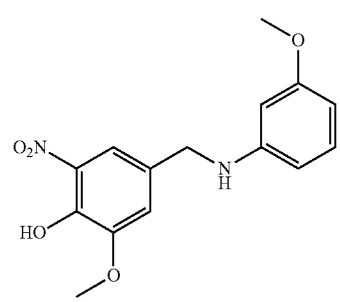 [SMILES: COc1cccc(NCc2cc(OC)c(O)c([N+](=O)[O-])c2)c1] | |
| CAP1159 | 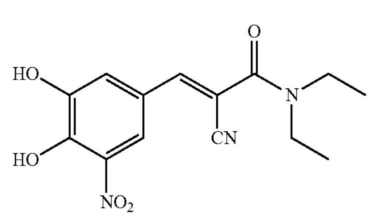 [SMILES: CCN(CC)C(=O)/C(C#N)=C/c1cc(O)c(O)c([N+](=O)[O-])c1] | 27 |

TABLE 3-continued

| Compound ID | Molecular Structure | Percent protection (at 200 μM) |
|---|---|---|
| CAP1160 | 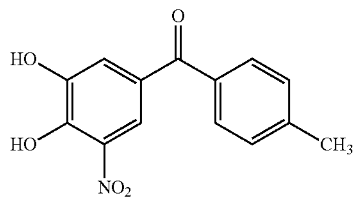 [SMILES: Cc1ccc(C(=O)c2cc(O)c(O)c([N+](=O)[O-])c2)cc1] | 65 |
| CAP1215 | ·2HCl | −47 |
| CAP1219 | 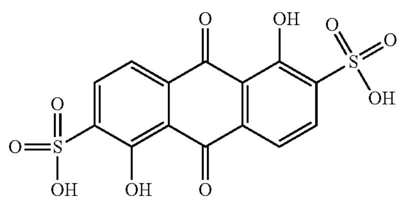 [SMILES: O=C1c2ccc(S(=O)(=O)O)c(O)c2C(=O)c2ccc(S(=O)(=O)O)c(O)c21] | −5 |
| CAP1220 | 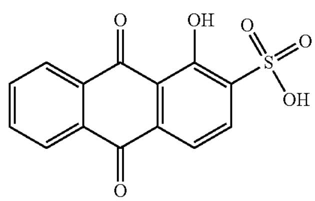 [SMILES: O=C1c2ccccc2C(=O)c2c1ccc(S(=O)(=O)O)c2O] | 20 |
| CAP1221 | 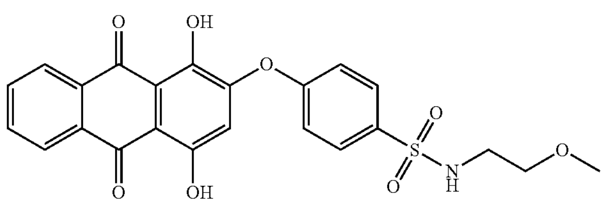 [SMILES: COCCNS(=O)(=O)c1ccc(Oc2cc(O)c3c(c2O)C(=O)c2ccccc2C3=O)cc1] | |
| CAP1222 | 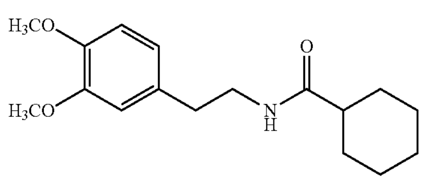 [SMILES: COc1ccc(CCNC(=O)C2CCCCC2)cc1OC] | 38 |
| CAP1223 | 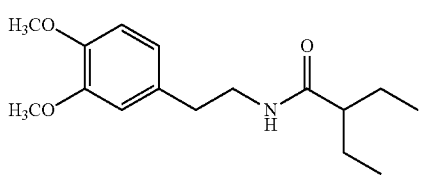 [SMILES: CCC(CC)C(=O)NCCc1ccc(OC)c(OC)c1] | 29 |

TABLE 3-continued
| Compound ID | Molecular Structure | Percent protection (at 200 μM) |
|---|---|---|
| CAP1224 | 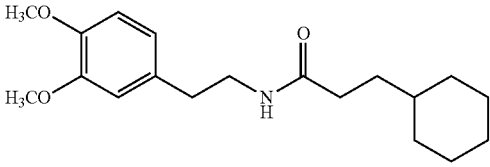 | 46 |
| CAP1225 | 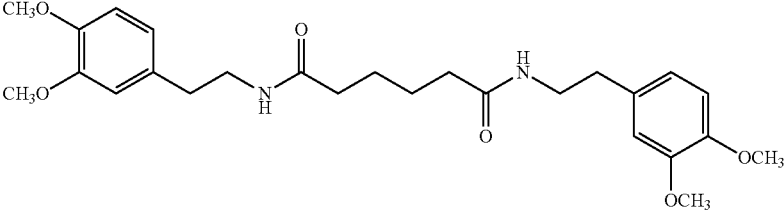 | 50 |
| CAP1226 | 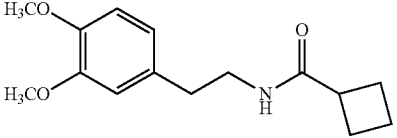 [SMILES: COc1ccc(CCNC(=O)C2CCC2)cc1OC] | 72 |
| CAP1227 | 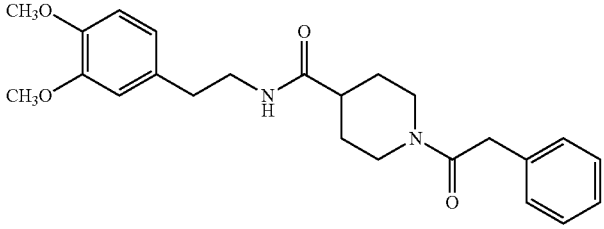 | 46 |
| CAP1228 | 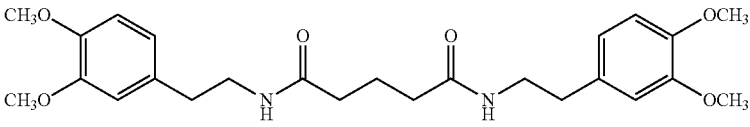 | 60 |
| CAP1229 | 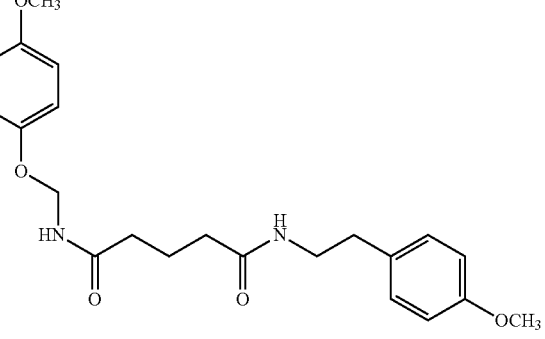 | 22 |
| CAP1230 | 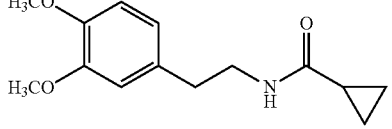 | 18 |

TABLE 3-continued

| Compound ID | Molecular Structure | Percent protection (at 200 μM) |
|---|---|---|
| CAP1231 | 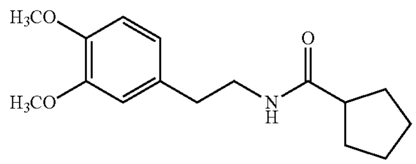 [SMILES: COc1ccc(CCNC(=O)C2CCCC2)cc1OC] | 51 |
| CAP1232 | 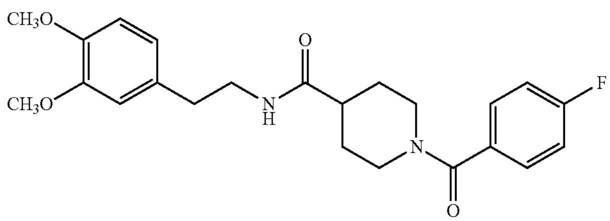 | 41 |
| CAP1236 | 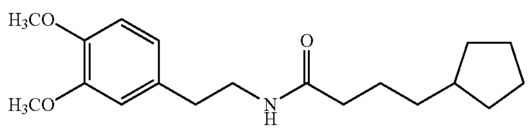 [SMILES: COc1ccc(CCNC(=O)CCCC2CCCC2)cc1OC] | −2 |
| CAP1237 | 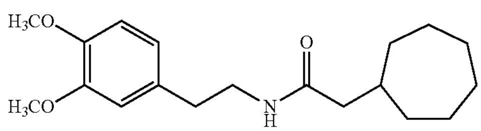 [SMILES: COc1ccc(CCNC(=O)CC2CCCCCC2)cc1OC] | |
| CAP1238 | 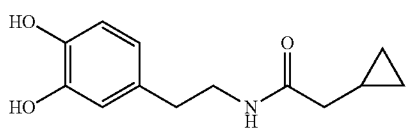 [SMILES: O=C(CC1CC1)NCCc1ccc(O)c(O)c1] | |
| CAP1239 | 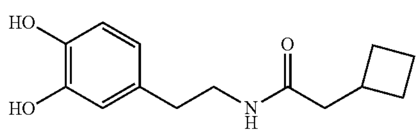 [SMILES: O=C(CC1CCC1)NCCc1ccc(O)c(O)c1] | 23 |
| CAP1240 | 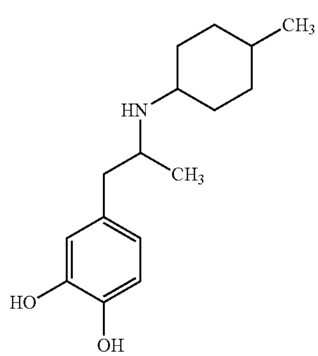 [SMILES: CC1CCC(NC(C)Cc2ccc(O)c(O)c2)CC1] | −13 |
| CAP1241 | 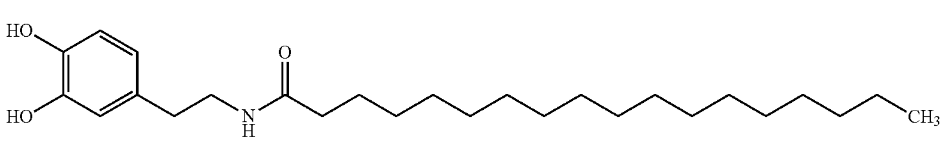 [SMILES: CCCCCCCCCCCCCCCCCC(=O)NCCc1ccc(O)c(O)c1] | 135 |

TABLE 3-continued

| Compound ID | Molecular Structure | Percent protection (at 200 μM) |
|---|---|---|
| CAP1242 | 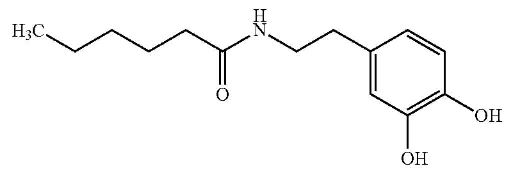 [SMILES: CCCCCC(=O)NCCc1ccc(O)c(O)c1] | |
| CAP1264 | 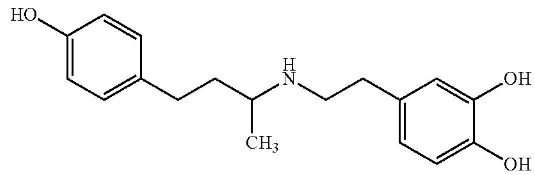 [SMILES: CC(CCc1ccc(O)cc1)NCCc1ccc(O)c(O)c1] | 3 |
| CAP1265 | 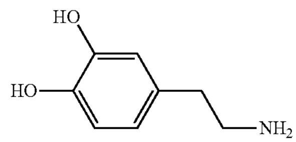 [SMILES: NCCc1ccc(O)c(O)c1] | −6 |
| CAP1266 | 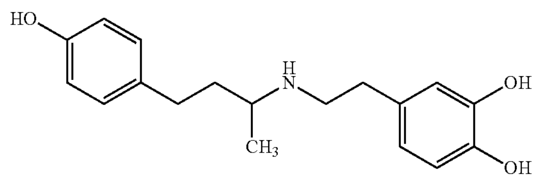 [SMILES: CC(CCc1ccc(O)cc1)NCCc1ccc(O)c(O)c1] | −14 |
| CAP1274 | 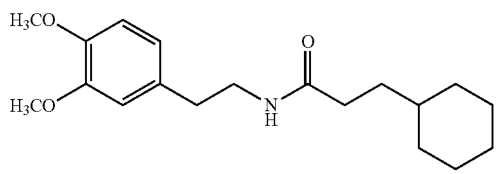 | 55 |
| CAP1276 | 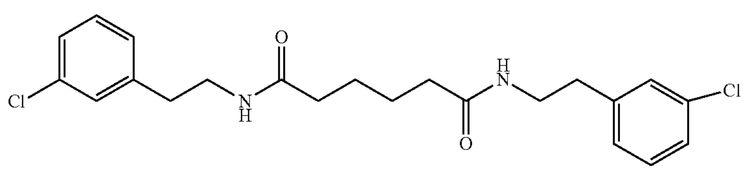 [SMILES: O=C(CCCCC(=O)NCCc1cccc(Cl)c1)NCCc1cccc(Cl)c1] | |
| CAP1277 | 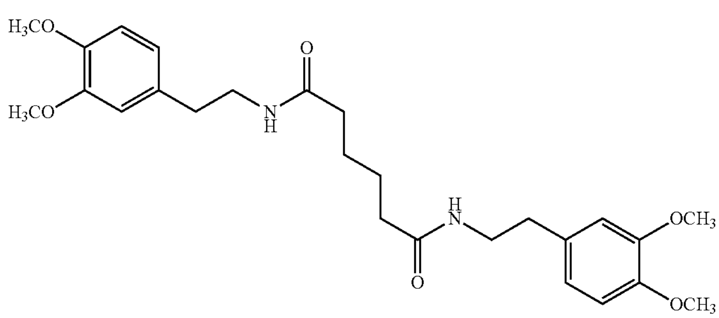 [SMILES: COc1ccc(CCNC(=O)CCCCC(=O)NCCc2ccc(OC)c(OC)c2)cc1OC] | |
| CAP1278 | 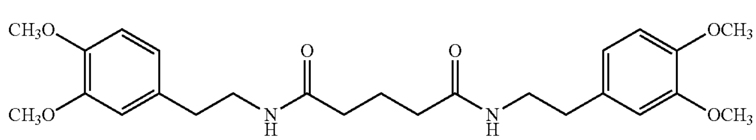 | 38 |

TABLE 3-continued
| Compound ID | Molecular Structure | Percent protection (at 200 μM) |
|---|---|---|
| CAP1279 | 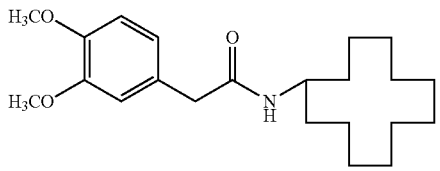 [SMILES: COc1ccc(CC(=O)NC2CCCCCCCCCCC2)cc1OC] | 5 |
| CAP1280 | 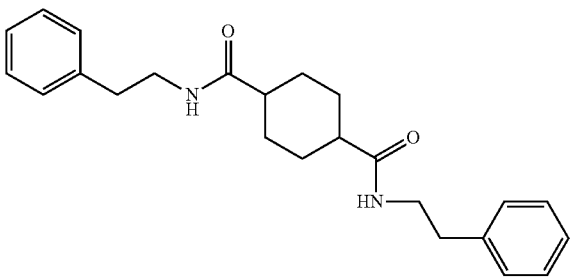 [SMILES: O=C(NCCc1ccccc1)C1CCC(C(=O)NCCc2ccccc2)CC1] | 44 |
| CAP1281 | 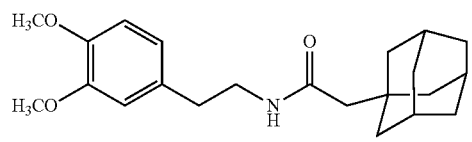 [SMILES: COc1ccc(CCNC(=O)CC23CC4CC(CC(C4)C2)C3)cc1OC] | 64 |
| CAP1347 | 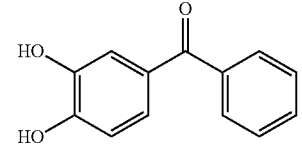 [SMILES: O=C(c1ccccc1)c1ccc(O)c(O)c1] | 13 |
| CAP1356 | 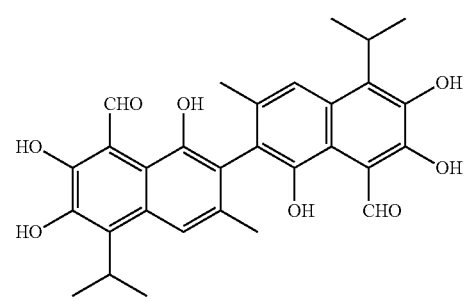 [SMILES: Cc1cc2c(C(C)C)c(O)c(O)c(C=O)c2c(O)c1-c1c(C)cc2c(C(C)C)c(O)c(O)c(C=O)c2c1O] | −46 |
| CAP1380 | 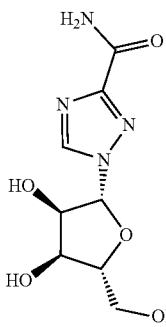 | 16 |
| CAP1447 | 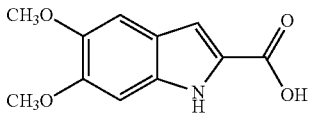 | 22 |

TABLE 3-continued

| Compound ID | Molecular Structure | Percent protection (at 200 μM) |
|---|---|---|
| CAP1450 | 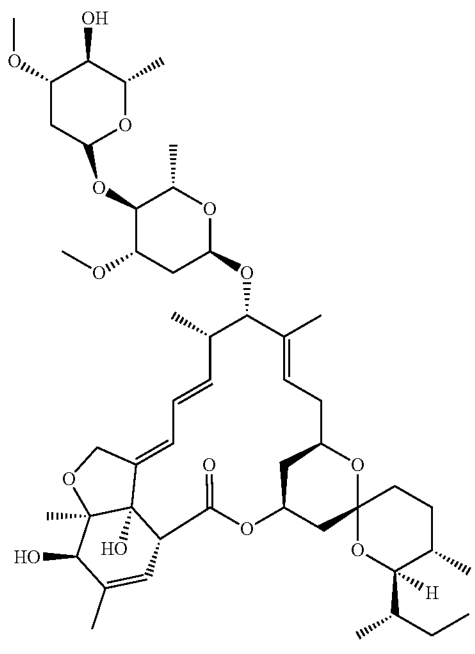 | |
| CAP1451 | 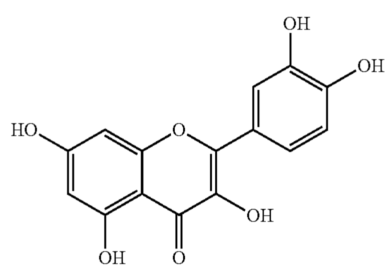 [SMILES: O=c1c(O)c(-c2ccc(O)c(O)c2)oc2cc(O)cc(O)c12] | 35 |
| CAP1457 | 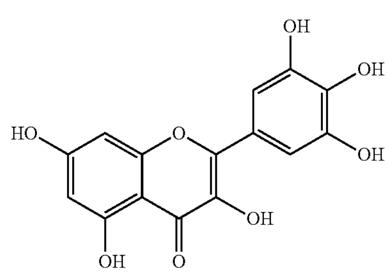 [SMILES: O=c1c(O)c(-c2cc(O)c(O)c(O)c2)oc2cc(O)cc(O)c12] | |
| CAP1458 | 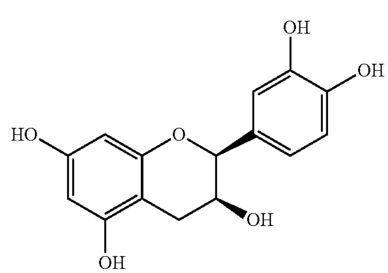 [SMILES: Oc1cc(O)c2c(c1)O[C@@H](c1ccc(O)c(O)c1)[C@@H](O)C2] | −17 |

TABLE 3-continued

| Compound ID | Molecular Structure | Percent protection (at 200 µM) |
|---|---|---|
| CAP1459 | (structure) | −95 |
| CAP1460 | (structure) | 1 |
| CAP1517 | (structure) | 40 |
| CAP1518 | (structure) | −4 |
| CAP1519 | (structure) | 9 |
| CAP3032 | (structure) ·H2O | −16 |

TABLE 3-continued
| Compound ID | Molecular Structure | Percent protection (at 200 μM) |
|---|---|---|
| CAP3035 | 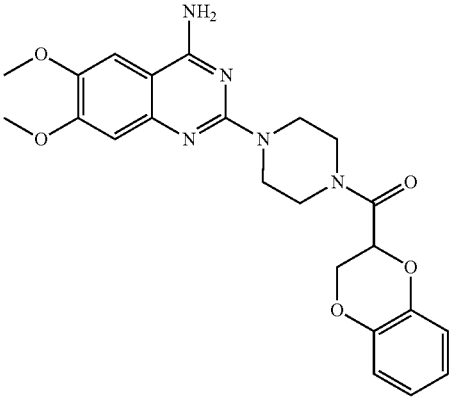 [SMILES: COc1cc2nc(N3CCN(C(=O)C4COc5ccccc5O4)CC3)nc(N)c2cc1OC] | 114 |
| CAP3037 | 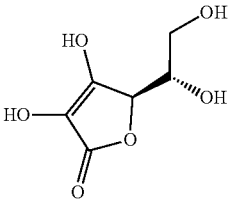 [SMILES: O=C1O[C@H]([C@@H](O)CO)C(O)=C1O] | −2 |
| CAP3040 | 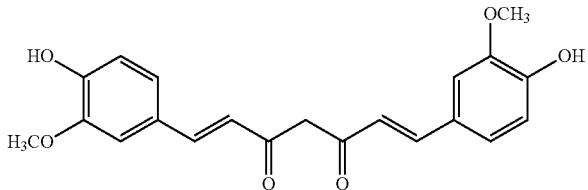 [SMILES: COc1cc(/C=C/C(=O)CC(=O)/C=C/c2ccc(O)c(OC)c2)ccc1O] | 4 |
| CAP3042 | 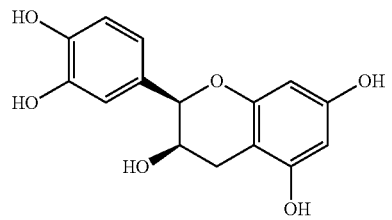 [SMILES: Oc1cc(O)c2c(c1)O[C@H](c1ccc(O)c(O)c1)[C@H](O)C2] | −17 |
| CAP3062 | 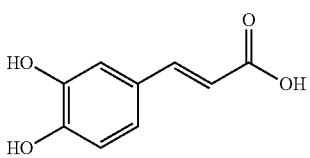 [SMILES: O=C(O)/C=C/c1ccc(O)c(O)c1] | 16 |
| CAP3064 | 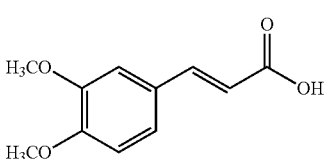 | 12 |
| CAP3065 | 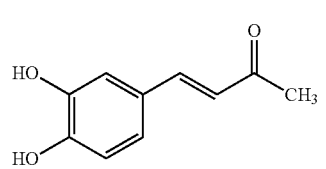 | −32 |

TABLE 3-continued

| Compound ID | Molecular Structure | Percent protection (at 200 µM) |
| --- | --- | --- |
| CAP3066 | 3,4-dimethoxyphenyl vinyl methyl ketone | 21 |
| CAP3067 | 3,4-dimethoxychalcone | −235 |
| CAP3071 | 1-(2-hydroxy-3-nitro-5-methylphenyl)ethanone | 30 |
| CAP3089 | (2-fluorophenyl)(3,4-dihydroxy-5-nitrophenyl)methanone | 56 |
| CAP3107 | 4-hydroxy-3,5-dimethoxybenzoic acid | 7 |

Table 4 below provides $EC_{50}$ values of select catechol derivatives in preventing $Ca^{+2}$ and UVC induced aggregation of alpha-A crystalline.

TABLE 4

| Compound ID | Molecular Structure | $EC_{50}$ (µM) |
| --- | --- | --- |
| CP1194 | 5,6-dihydroxyindole | 1096 |
| CAP1042 | L-DOPA | 860.3 |

TABLE 4-continued
| Compound ID | Molecular Structure | EC$_{50}$ (μM) |
|---|---|---|
| CAP1053 | 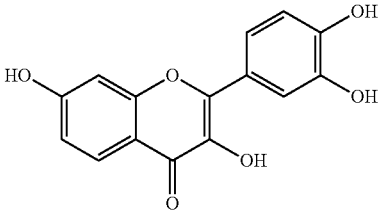 [SMILES: O=c1c(O)c(-c2ccc(O)c(O)c2)oc2cc(O)ccc12] | 461.1 |
| CAP1159 | 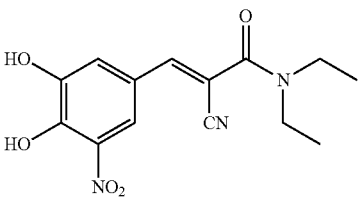 | 312.9 |
| CAP1160 | 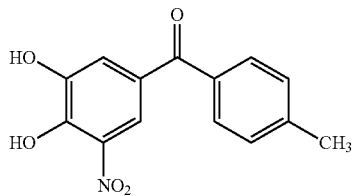 | 63.5 |
| CAP1224 | 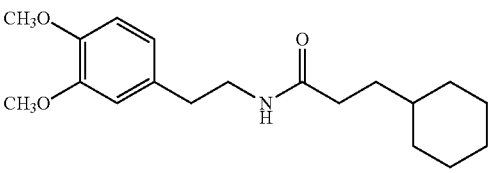 | 879.9 |
| CAP1226 | 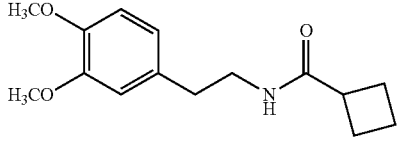 [SMILES: COc1ccc(CCNC(=O)C2CCC2)cc1OC] | 46.2 |
| CAP1227 | 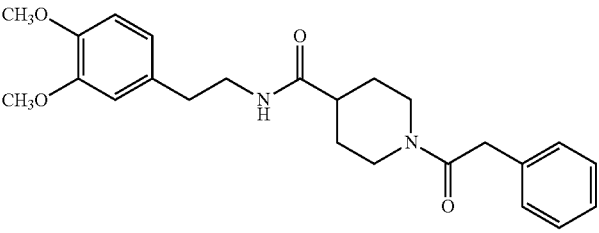 | 288.1 |
| CAP1280 | 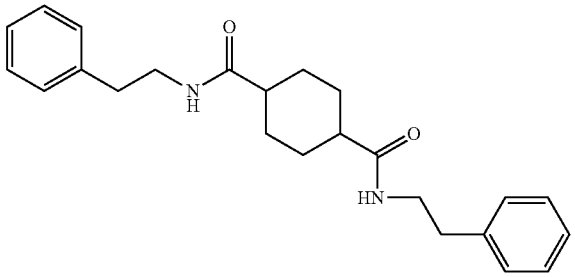 [SMILES: O=C(NCCc1ccccc1)C1CCC(C(=O)NCCc2ccccc2)CC1] | 193.3 |

TABLE 4-continued

| Compound ID | Molecular Structure | EC$_{50}$ (µM) |
|---|---|---|
| CAP1347 | 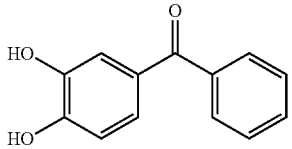 | 115.1 |
| CAP3089 | 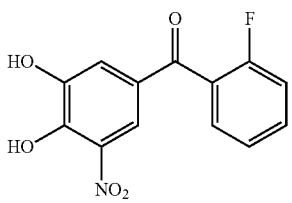 [SMILES: O=C(c1cc(O)c(O)c([N+](=O)[O-])c1)c1ccccc1F] | 361.9 |

Example 7. Effectiveness of Select Tolcapone Derivatives in Preventing UV- and Heat-Induced Aggregation of Alpha-A Crystalline Table 5 below lists select tolcapone derivatives and their effectiveness in preventing UV- and heat induced aggregation of alpha-A crystalline.

TABLE 5

| CAP ID | Structure | Biochemical (UVC) Assay (Absorbance) | Biochemical Assay (GEL) | Ex Vivo | Cell-based [UV] (max % net protection) | Cell-based [Heat] (max % net protection) |
|---|---|---|---|---|---|---|
| 1160 | 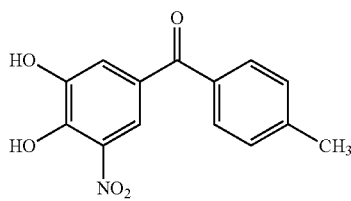 | + | + | + | 68 | 23 |
| 3089 | 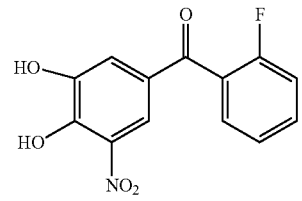 [SMILES: O=C(c1cc(O)c(O)c([N+](=O)[O-])c1)c1ccccc1F] | | | | 31 | 0 |
| 1347 | 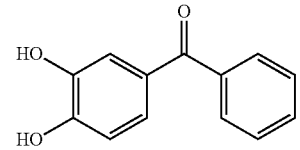 | | | | 28 | 8 |
| 4126 | 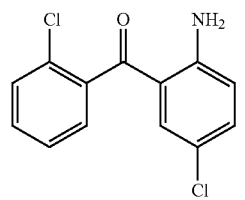 [SMILES: Nc1ccc(Cl)cc1C(=O)c1ccccc1Cl] | ± | ± | ND | 0 | |

TABLE 5-continued

| CAP ID | Structure | Biochemical (UVC) Assay (Absorbance) | Biochemical Assay (GEL) | Ex Vivo | Cell-based [UV] (max % net protection) | Cell-based [Heat] (max % net protection) |
|---|---|---|---|---|---|---|
| 4127 | benzophenone | + | − | ND | 55 | 9 |
| 4128 | 4-aminobenzophenone | + | ± | − | 23 | |
| 4129 | 3,4-diaminobenzophenone | + | + | ± | 37 | 0 |
| 4130 | 4-methoxybenzophenone | + | − | ND | 55 | 42 |
| 4131 | 4-nitrobenzophenone | ± | − | ND | 0 | ND |
| 4132 | 3,4-dimethoxybenzophenone | + | − | ND | 39 | 0 |
| 4133 | 2,3,4-trihydroxybenzophenone | + | + | ± | 22 | 18 |
| 4135 | 2-hydroxy-4-methoxy-5-sulfobenzophenone sodium salt | + | ± | ± | 75 | 4 |

TABLE 5-continued

| CAP ID | Structure | Biochemical (UVC) Assay (Absorbance) | Biochemical Assay (GEL) | Ex Vivo | Cell-based [UV] (max % net protection) | Cell-based [Heat] (max % net protection) |
|---|---|---|---|---|---|---|
| 4136 | (structure) | + | + | ± | 70 | 5 |
| 4140 | (structure) | | | | ND | ND |
| 4151 | (structure) | | | | ND | ND |
| 4152 | (structure) | | | | 17 | 0 |
| 4153 | (structure) | | | | ND | ND |
| 4160 | (structure) | + | − | ND | 82 | 0 |
| 4161 | (structure) | ± | − | ND | 38 | 8 |

TABLE 5-continued

| CAP ID | Structure | Biochemical (UVC) Assay (Absorbance) | Biochemical Assay (GEL) | Ex Vivo | Cell-based [UV] (max % net protection) | Cell-based [Heat] (max % net protection) |
|---|---|---|---|---|---|---|
| 4162 | 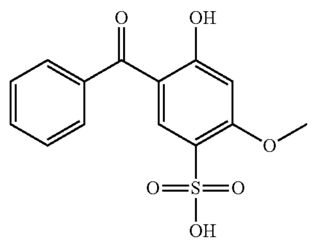 [SMILES: COc1cc(O)c(C(=O)c2ccccc2)cc1S(=O)(=O)O] | | | | 60 | 3 |
| 4172 | 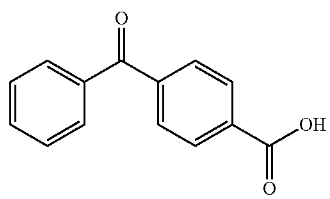 [SMILES: O=C(O)c1ccc(C(=O)c2ccccc2)cc1] | + | − | ND | 67 | 9 |
| 4173 | 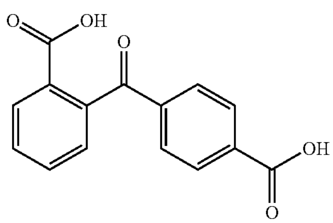 [SMILES: O=C(O)c1ccc(C(=O)c2ccccc2C(=O)O)cc1] | + | − | ND | 61 | 0 |
| 4196 | 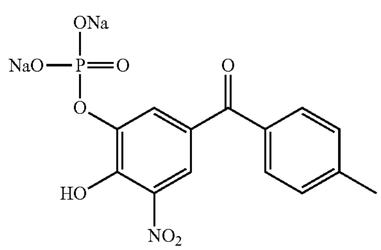 | | | | 63 | 38 |
| 4255 | 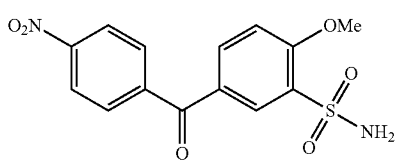 [SMILES: COc1ccc(C(=O)c2ccc([N+](=O)[O-])cc2)cc1S(N)(=O)=O] | | | | ND | ND |
| 4256 | 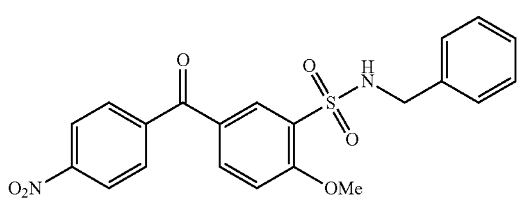 [SMILES: COc1ccc(C(=O)c2ccc([N+](=O)[O-])cc2)cc1S(=O)(=O)NCc1ccccc1] | ND | + | − | 7 | ND |
| 4257 | 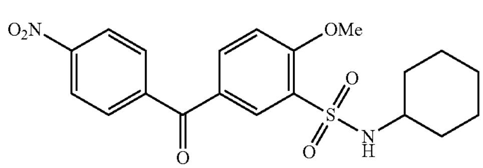 [SMILES: COc1ccc(C(=O)c2ccc([N+](=O)[O-])cc2)cc1S(=O)(=O)NC1CCCCC1] | ND | + | − | 19 | ND |

TABLE 5-continued

| CAP ID | Structure | Biochemical (UVC) Assay (Absorbance) | Biochemical Assay (GEL) | Ex Vivo | Cell-based [UV] (max % net protection) | Cell-based [Heat] (max % net protection) |
|---|---|---|---|---|---|---|
| 4258 | 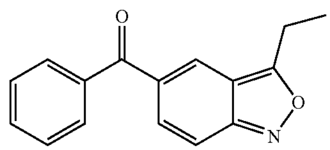 [SMILES: CCc1onc2ccc(C(=O)c3ccccc3)cc12] | ND | + | – | 36 | ND |
| 4265 | 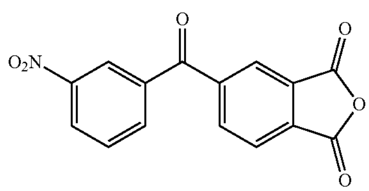 [SMILES: O=C(c1cccc([N+](=O)[O-])c1)c1ccc2c(c1)C(=O)OC2=O] | ND | ± | ND | 129 | 17 |
| 4269 | 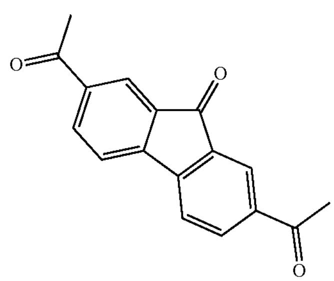 [SMILES: CC(=O)c1ccc2c(c1)C(=O)c1cc(C(C)=O)ccc1-2] | ND | ND | – | ND | ND |
| 4270 | 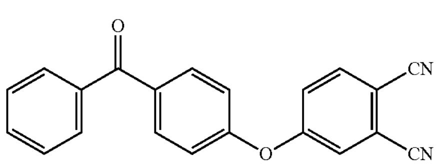 [SMILES: N#Cc1ccc(Oc2ccc(C(=O)c3ccccc3)cc2)cc1C#N] | ND | – | ND | ND | ND |
| 4271 | 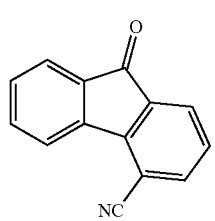 [SMILES: N#Cc1cccc2c1-c1ccccc1C2=O] | ND | – | ND | ND | ND |
| 4272 | 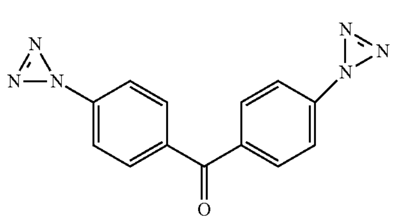 [SMILES: O=C(c1ccc(N2N=N2)cc1)c1ccc(N2N=N2)cc1] | ND | – | ND | ND | ND |

TABLE 5-continued

| CAP ID | Structure | Biochemical (UVC) Assay (Absorbance) | Biochemical Assay (GEL) | Ex Vivo | Cell-based [UV] (max % net protection) | Cell-based [Heat] (max % net protection) |
|---|---|---|---|---|---|---|
| 4279 | 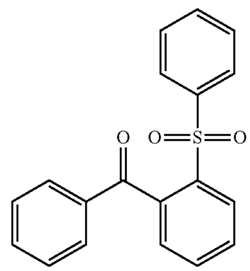 [SMILES: O=C(c1ccccc1)c1ccccc1S(=O)(=O)c1ccccc1] | ND | + | ± | 5 | 0 |
| 4281 | 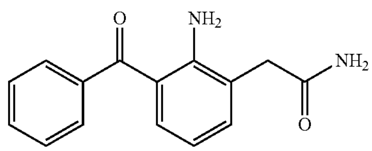 [SMILES: NC(=O)Cc1cccc(C(=O)c2ccccc2)c1N] | ND | + | − | 38 | 8 |
| 4318 | 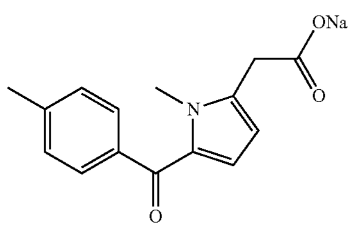 | | | | ND | ND |
| 4324 | 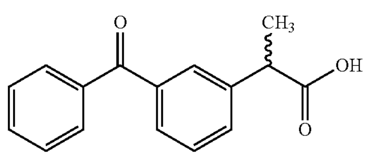 [SMILES: CC(C(=O)O)c1cccc(C(=O)c2ccccc2)c1] | | | | ND | ND |

Example 8. Prodrugs of Tolcapone

As described above, topical administration is the preferred route for ophthalmic drugs due to its localized drug action at anterior segment of the eye. However, poor penetration and rapid loss of therapeutics following its topical administration are the major restrictions of the topical route. The problem is further amplified and compounded if the given drug has poor aqueous solubility. Formulation approach has been extensively used to address and overcome the poor ocular bioavailability. Besides formulation, chemical approach such as prodrug has been utilized to optimize physicochemical and biochemical properties of a drug molecule for increasing its ocular bioavailability. An essential step in effective prodrug therapy is the activation of the prodrug and the release of the free active therapeutic agent. Important enzymes involved in the activation and bioconversion of prodrugs include phosphatase, paraoxonase, carboxylesterase, acetylcholinesterase, and cholinesterase.

Use of tolcapone is associated with side effects, particularly liver injury. Improving solubility of tolcapone, for example, by administering it as a prodrug can lead to the drug being effective at lower doses. To improve the aqueous solubility of tolcapone, a prodrug of tolcapone, CAP4196 was synthesized. It is believed that increased solubility of the prodrug would lead to a more effective treatment of and ocular diseases (presbyopia or cataract), Parkinson's disease, Amyloid diseases, and prevention and/or treatment of transthyretin (TTR)-associated amyloidosis.

Synthesis of CAP4196

SCHEME 5

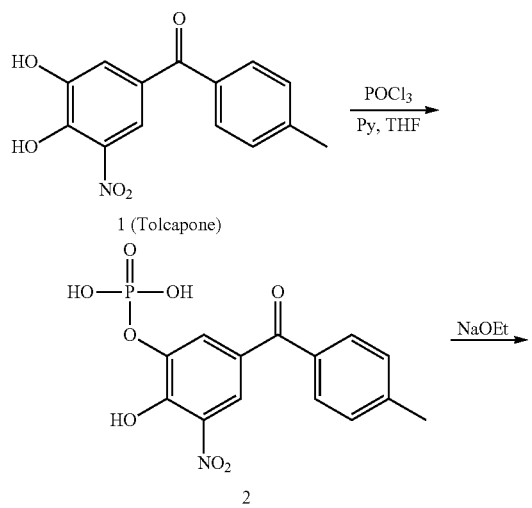

Sodium 2-hydroxy-5-(4-methylbenzoyl)-3-nitrophenyl phosphate, (CAP4196): To a cold solution of Tolcapone (1, 20 g) in THF (100 mL) and Pyridine (25 mL), POCl$_3$ (20 mL) was added drop wise via addition funnel over a period of 20 min. The reaction mixture was stirred at room temperature for overnight and cooled to below 10° C. The reaction was quenched by 50% aq. phosphoric acid solution and stirring was continued at RT for 10 hrs. The reaction mixture was further diluted with THF (100 mL) and water (100 mL), precipitated solid was filtered, washed with ethyl acetate (2×50 mL) and dried to afford intermediate 2, Tolcapone monophosphate (8.0 g), as an off-white solid.

To a stirred suspension of Tolcapone monophosphate (2, 15 g) in EtOH (300 ml), NaOEt in EtOH (2.5 eq) was added and the suspension stirred for 1 hr. The orange red solid obtained was filtered, washed with EtOH (2×100 ml) and dried to afford Tolcapone monophosphate disodium salt (14 g), CAP4196 as orange red solid.

Solubility: The solubility of CAP1160 and CAP4196 was tested with different FDA approved excipients such as cyclodextrin, PEG-b-PCL, Kolliphor-EL, Kolliphor-40, sorbitol, propelyne glycol, sodium phosphate, etc. Only a 10-fold improvement (1.5 mg/ml) in the solubility of CAP1160 was observed with (2-hydroxypropyl)-beta-cyclodextrin. On the other hand, CAP4196, the phosphate prodrug demonstrated greater than 660-fold improvement (100 mg/ml) in solubility D with only water as solvent and the pH of the formulation was 6.65, which is within the pH range of the tears (6.5-7.6). This makes the formulation safe for topical use (see Table 6).

TABLE 6

Solubility of CAP1160 and CAP4196

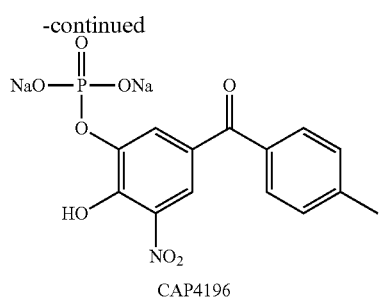

| FDA approved excipients | CAP1160 | CAP4196 |
|---|---|---|
| Solubility in water mg/ml | 0.1 | 100 |
| Solubility in water with (2-hydroxypropyl)-beta cyclodextrin mg/ml (1:1) | 2 | 100 |
| With PEG-b-PCL (1:1) mg/ml in water | 1 | ND |
| With Kolliphor 40 (1:1) In water | 1 | ND |

Example 9: Ocular Safety in New Zealand White Rabbits (NZWR) with Repeated Dose of Prodrug CAP4196 for 7 Days Prodrug CAP4196 is well-tolerated up to 10% concentration in New Zealand white rabbits. Initial maximum tolerated dose studies (MTD) help identify observable signs of toxicity and provide a rationale for setting dose levels in later definitive studies. Therefore, the MTD of CAP4196 was evaluated in New Zealand white rabbits. Four animals per group were dosed with increasing concentrations (0.25, 2.5, 8 and 10%) of CAP4196 at 50 µl volume q.i.d. dosing at 2 hrs interval. Following the dosing, the animals were evaluated for mortality and morbidity, ophthalmological examination, body weight, and clinical pathology before start of dosing then on dosing days 2, 4, and 6 prior to first dose instillation and on day 7, one hour after last dose instillation.

Based on the results, it was concluded that administration of CAP4196 (50 μL, 4 times a day with an interval of 2 hours in between each dosing) at dose concentration of 10% w/v produced only few temporary local reactions like excessive rubbing of eyes and redness and did not produced any systemic toxicity in New Zealand white rabbits followed in this MTD study. Hence, the highest dose concentration of 10% was considered as the MTD. See Table 7.

TABLE 7

Toxicity results of CAP4196

| Group No. | Group Details | Dose Level | Sex | Total No. of Animals | Mortality and Morbidity |
|---|---|---|---|---|---|
| G1 | CAP4196 ophthalmic formulation (0.25% w/v) | 50 μL × 4 times a day in each eye | Male | 3 | 0 |
| G2 | CAP4196 ophthalmic formulation (4% w/v) | 50 μL × 4 times a day in each eye | Male | 3 | 0 |
| G3 | CAP4196 ophthalmic formulation (8% w/v) | 50 μL × 4 times a day in each eye | Male | 3 | 0 |
| G4 | CAP4196 ophthalmic formulation (10% w/v) | 50 μL × 4 times a day in each eye | Male | 3 | 0 |

Example 9. Tolcapone Derivatives in Prevention or Treatment of Thransthyretin and Parkinson's Disease Transthyretin (TTR) is a plasma homotetrameric protein with a role in fatal systemic Amyloidosis (Sant'Anna, R. et al. (2016) *Nat. Commun.* 7:10787 doi: 10.1038/ncomms10787). TTR tetramer dissociation precedes pathological TTR aggregation. Native state stabilizers of the TTR tetramer are promising drugs to treat TTR amyloidoses. Tolcapone, an FDA-approved molecule for Parkinson's disease, is a potent TTR aggregation inhibitor (Sant'Anna, R. et al. (2016)). Tolcapone binds specifically to TTR in human plasma, stabilizes the native tetramer in vivo in mice and humans and inhibits TTR cytotoxicity ((Sant'Anna, R. et al. (2016). As such, tolcapone believed to be a strong candidate for treating TTR amyloidosis. Since tolcapone use is associated with side effects, particularly liver injury, and improving solubility of tolcapone, for example, by administering it as a prodrug can lead to the drug being effective at lower dose, it is contemplated that prodrugs of tolcapone described herein would be better as therapeutics against TTR amyloidosis and Parkinson's disease.

Example 10: Structure Activity Relationship of Naphthalene Analogs

Structure activity relationship of Naphthalene analogs are summarized in Table 8 below.

TABLE 8

| ID | Structure | Biochemical | Gel | Ex-vivo | Cell UV % protection | Cell Heat % protection |
|---|---|---|---|---|---|---|
| CAP4179 | 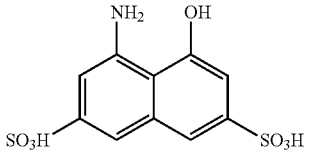 [SMILES: Nc1cc(S(=O)(=O)O)cc2cc(S(=O)(=O)O)cc(O)c12] | + | + | ND | 61 | 29 |
| CAP4180 | 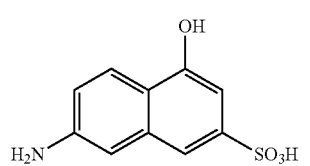 [SMILES: Nc1ccc2c(O)cc(S(=O)(=O)O)cc2c1] | + | + | + | 53 | 22 |

TABLE 8-continued

| ID | Structure | Biochemical | Gel | Ex-vivo | Cell UV % protection | Cell Heat % protection |
|---|---|---|---|---|---|---|
| CAP4183 | 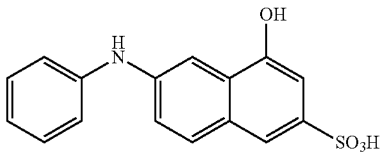 [SMILES: O=S(=O)(O)c1cc(O)c2cc(Nc3ccccc3)ccc2c1] | + | + | + | 82 | 17 |
| CAP4184 | 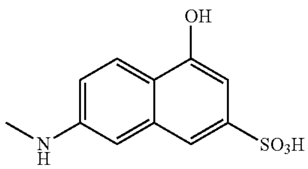 [SMILES: CNc1ccc2c(O)cc(S(=O)(=O)O)cc2c1] | + | + | 15% | 49 | 4 |
| CAP4186 | 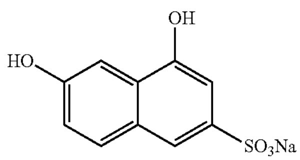 | + | + | ND | 54 | 17 |
| CAP4187 | 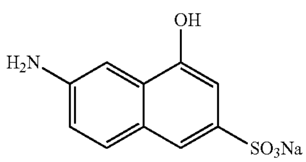 | + | + | + | 62 | 19 |
| CAP4188 | 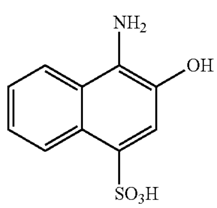 [SMILES: Nc1c(O)cc(S(=O)(=O)O)c2ccccc12] | + | + | ND | 0 | 2 |
| CAP4190 | 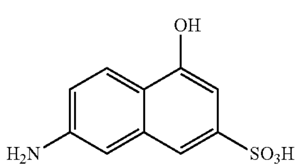 | | | | 65 | 15 |
| CAP4209 | 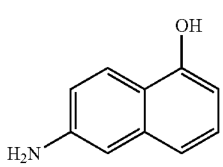 [SMILES: Nc1ccc2c(O)cccc2c1] | | | | 0 | |
| CAP4210 | 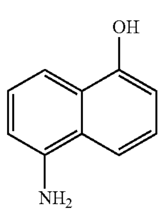 [SMILES: Nc1cccc2c(O)cccc12] | | | | 1 | |

TABLE 8-continued
| ID | Structure | Biochemical | Gel | Ex-vivo | Cell UV % protection | Cell Heat % protection |
|---|---|---|---|---|---|---|
| CAP4211 | 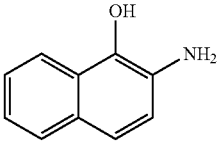 [SMILES: Nc1ccc2ccccc2c1O] | | | | 0 | |
| CAP4212 | 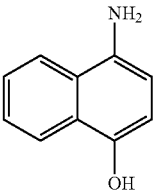 [SMILES: Nc1ccc(O)c2ccccc12] | | | | 0 | |
| CAP4213 | 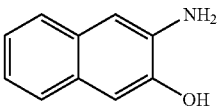 [SMILES: Nc1cc2ccccc2cc1O] | | | | 14 | |
| CAP4214 | 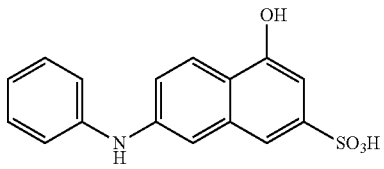 [SMILES: O=S(=O)(O)c1cc(O)c2ccc(Nc3ccccc3)cc2c1] | | | – | 86 | |
| CAP4215 | 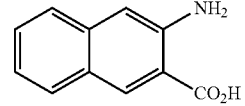 | | | – | 46 | |
| CAP4216 | 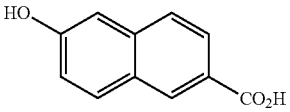 | | | – | 49 | |
| CAP4217 | 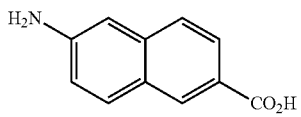 | | | – | 41 | |
| CAP4218 | 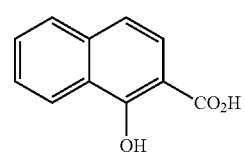 [SMILES: O=C(O)c1ccc2ccccc2c1O] | | | – | 38 | |
| CAP4221 | 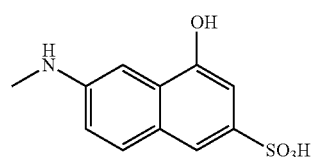 | | | | 50 | |
| CAP4222 | 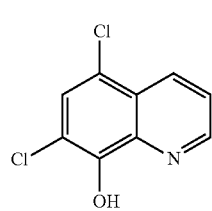 [SMILES: Oc1c(Cl)cc(Cl)c2cccnc12] | | | – | 27 | |

TABLE 8-continued

| ID | Structure | Biochemical | Gel | Ex-vivo | Cell UV % protection | Cell Heat % protection |
|---|---|---|---|---|---|---|
| CP01191 | 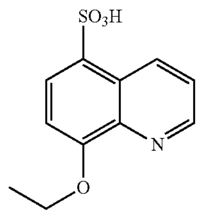 [SMILES: CCOc1ccc(S(=O)(=O)O)c2cccnc12] | | | − | 23 | |
| CAP4223 | 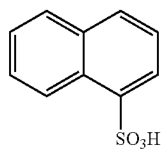 [SMILES: O=S(=O)(O)c1cccc2ccccc12] | | | | 16 | |
| CAP4224 | 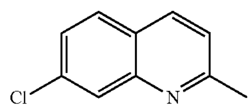 | | | | 0 | |
| CP01181 | 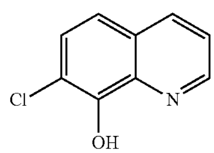 [SMILES: Oc1c(Cl)ccc2cccnc12] | | | | 11 | |
| CP0098 | 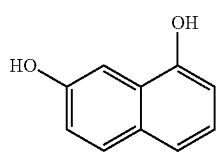 [SMILES: Oc1ccc2cccc(O)c2c1] | | | | 1 | |
| CAP4225 | 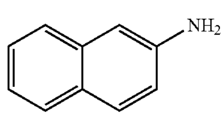 [SMILES: Nc1ccc2ccccc2c1] | | + | + | 3 | |
| CP01185 | 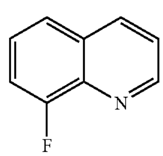 [SMILES: Fc1cccc2cccnc12] | | | | 13 | |
| CAP4226 | 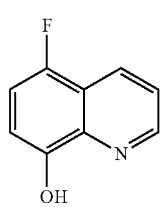 [SMILES: Oc1ccc(F)c2cccnc12] | | | | 18 | |
| CP0080 | 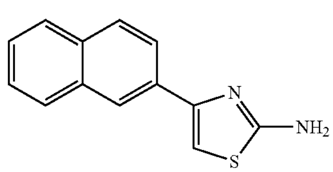 [SMILES: Nc1nc(-c2ccc3ccccc3c2)cs1] | | + | − | 47 | |

TABLE 8-continued

| ID | Structure | Biochemical | Gel | Ex-vivo | Cell UV % protection | Cell Heat % protection |
|---|---|---|---|---|---|---|
| CP0103 | 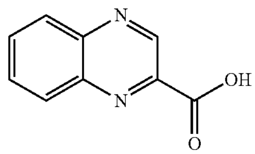 [SMILES: O=C(O)c1cnc2ccccc2n1] | | | | | 66 |
| CAP4227 | 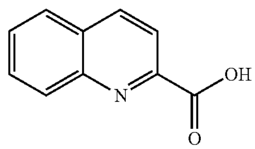 [SMILES: O=C(O)c1ccc2ccccc2n1] | | | | | 38 |
| CP01189 | 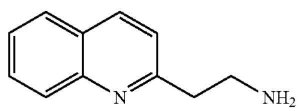 [SMILES: NCCc1ccc2ccccc2n1] | | | | | 13 |
| CAP4228 | 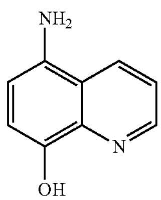 [SMILES: Nc1ccc(O)c2ncccc12] | | | | | 4 |
| CAP4230 | 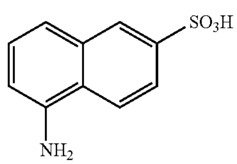 [SMILES: Nc1cccc2cc(S(=O)(=O)O)ccc12] | | + | − | | 51 |
| CP0094 | 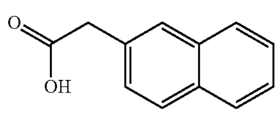 [SMILES: O=C(O)Cc1ccc2ccccc2c1] | | | | | 55 |
| CP0098 | 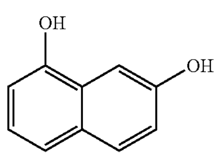 [SMILES: Oc1ccc2cccc(O)c2c1] | | | + | | 1 |
| CP0110 | 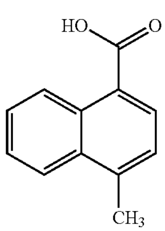 | | | − | | 3 |
| CP1101 | 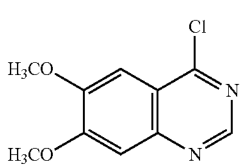 [SMILES: COc1cc2ncnc(Cl)c2cc1OC] | | | − | | 0 |

EQUIVALENTS

All the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for treating presbyopia or cataract in a subject in need thereof, the method comprising administering to the subject an effective amount of a composition comprising, as a sole active agent, a compound having formula (VII):

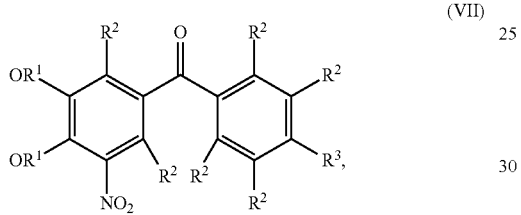

or a solvate or a pharmaceutically acceptable salt thereof, wherein $R^1$ is independently selected from the group consisting of hydrogen; $(C_1-C_3)$alkyl; halo$(C_1-C_3)$alkyl; $(C_3-C_6)$cycloalkyl; halo$(C_3-C_6)$cycloalkyl; $(C_1-C_3)$alkyloxy; and $R^4C$=O; wherein $R^4$ is selected from the $(C_1-C_6)$alkyl; halo$(C_1-C_6)$alkyl; $(C_3-C_6)$cycloalkyl; halo$(C_3-C_6)$cycloalkyl; aryl; haloaryl; and

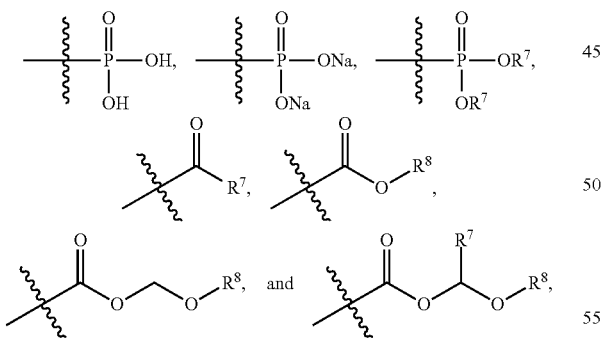

wherein $R^7$ is $(C_1-C_6)$alkyl and $R^8$ is $(C_1-C_6)$alkyl, aryl, or a polyethylene glycol group;

$R^2$ is independently selected from the group consisting of hydrogen, $R^5$, $OR^5$, $N(R^5)(R^6)$, halide, CN, $NO_2$, C(O)$OR^5$, CON$(R^5)(R^6)$, S(O)N$R^5{}_2$, $SO_3H$, $SO_2CH_3$, phenyl, biphenyl, phenoxy-phenyl, and polyethyleneglycol groups, wherein $R^5$ and $R^6$ are independently selected from hydrogen atom, $(C_1-C_6)$alkyl, halo$(C_1-C_6)$alkyl, $(C_3-C_6)$cycloalkyl, halo$(C_3-C_6)$cycloalkyl, $(C_3-C_6)$cycloalkyl$(C_1-C_6)$alkyl, halo$(C_3-C_6)$cycloalkyl$(C_1-C_6)$alkyl, and $(C_3-C_6)$cycloalkylhalo$(C_1-C_6)$alkyl groups; wherein $R^2$ can occupy 0-2 positions in the ring of its occurrence; and wherein, in the event any two adjacent groups selected are $OR^5$ groups, the two $OR^5$ groups may optionally be cross-linked via their $R^5$ functionalities to form an additional ring; and $R^3$ is selected from the group consisting of hydrogen, $(C_1-C_6)$alkyl, halo$(C_1-C_6)$alkyl, $(C_3-C_6)$cycloalkyl, halo$(C_3-C_6)$cycloalkyl, $(C_2-C_6)$alkenyl, halo$(C_2-C_6)$alkenyl, and hydroxy$(C_2-C_6)$alkenyl, and wherein the method is free of a step of administering a second active agent.

2. The method of claim 1, wherein the compound is

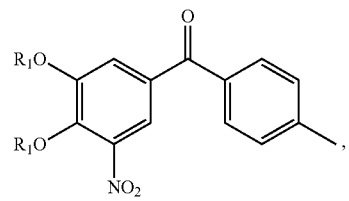

wherein $R^1$ is independently selected form the group consisting of

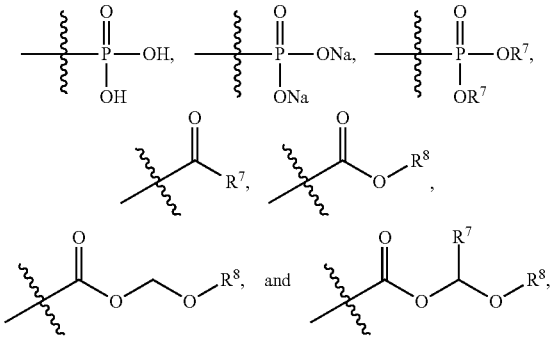

wherein $R^7$ is $(C_1-C_6)$alkyl and $R^8$ is $(C_1-C_6)$alkyl, aryl, or a polyethylene glycol group.

3. The method of claim 1, wherein each $R^1$ is a hydrogen atom.

4. The method of claim 1, wherein each $R^1$ is an $(C_1-C_3)$ alkyl.

5. The method of claim 1, wherein one $R^1$ is a hydrogen or an $(C_1-C_3)$alkyl, and the other $R^1$ is $R^4C$=O, wherein $R^4$ is $CH_3$ or $C_6H_5$.

6. The method of claim 1, wherein the compound is

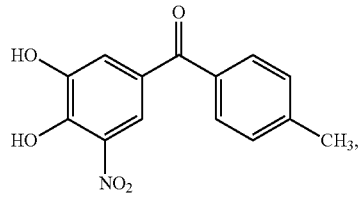

-continued

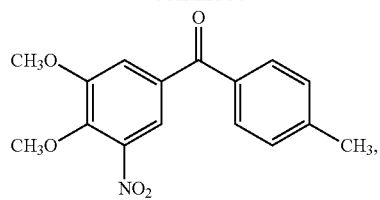

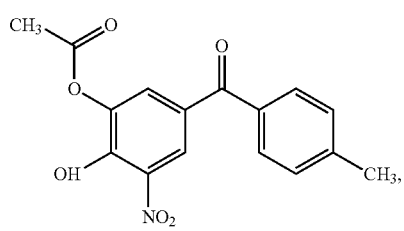

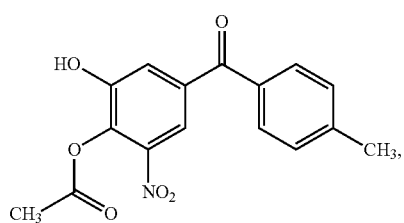

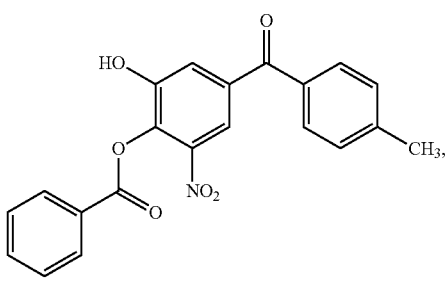

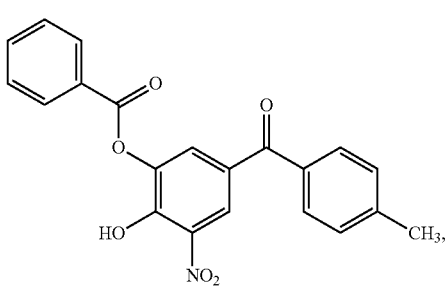

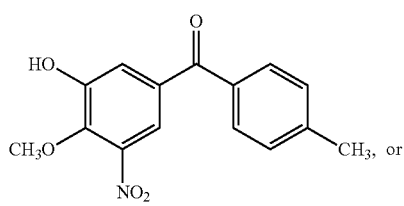

-continued

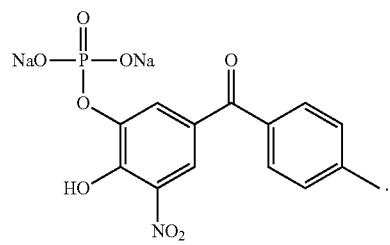

7. The method of claim 1, wherein one of the two $R^1$ is

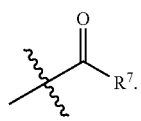

8. The method of claim 1, wherein $R^2$ is hydrogen and one of the two $R^1$ is

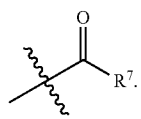

9. The method of claim 1, wherein $R^2$ is hydrogen and one of the two $R^1$ is $R^4C=O$, wherein is $R^4$ is $(C_1-C_6)$alkyl or an aryl.

10. The method of claim 1, wherein both $R^1$ and $R^2$ are hydrogen.

11. The method of claim 1, wherein $R^2$ is hydrogen and one of the two $R^1$ is

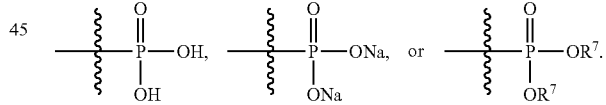

12. The method of claim 11, wherein $R^7$ is a methyl, ethyl, or a propyl group.

13. The method of claim 1, wherein $R^2$ is hydrogen and both $R^1$ are

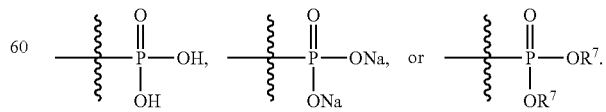

14. The method of claim 13, wherein $R^7$ is a methyl, ethyl, or a propyl group.

15. The method of claim 1, wherein $R^2$ is hydrogen and one of the two $R^1$ is
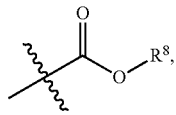
wherein $R^8$ is a $(C_1-C_6)$alkyl or an aryl.
16. The method of claim 1, wherein $R^2$ is hydrogen and one of the two $R^1$ is
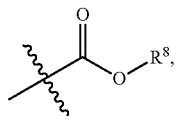
wherein $R^8$ is a polyethylene glycol.
17. The method of claim 1, wherein the compound is
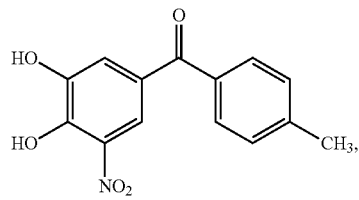
18. The method of claim 1, wherein the compound is
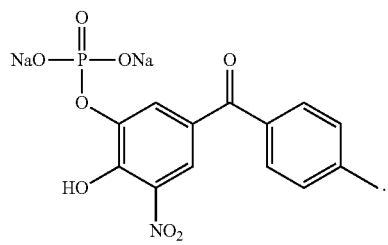
19. The method of claim 1, wherein the compound is
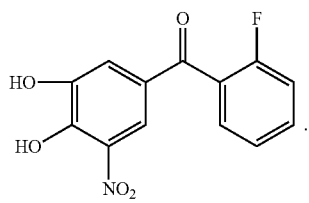 [SMILES: O=C(c1cc(O)c(O)c([N+](=O)[O-])c1)c1ccccc1F]
* * * * *